(12) United States Patent
Imamura et al.

(10) Patent No.: US 10,973,406 B2
(45) Date of Patent: Apr. 13, 2021

(54) IMAGE PROCESSING APPARATUS, IMAGE PROCESSING METHOD, AND NON-TRANSITORY COMPUTER READABLE MEDIUM

(71) Applicant: CANON KABUSHIKI KAISHA, Tokyo (JP)

(72) Inventors: Hiroshi Imamura, Kawasaki (JP); Yoshihiko Iwase, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 135 days.

(21) Appl. No.: 16/286,945

(22) Filed: Feb. 27, 2019

(65) Prior Publication Data
US 2019/0274542 A1 Sep. 12, 2019

(30) Foreign Application Priority Data
Mar. 6, 2018 (JP) .............................. JP2018-040031
Mar. 6, 2018 (JP) .............................. JP2018-040032

(51) Int. Cl.
| G06K 9/00 | (2006.01) |
| A61B 3/14 | (2006.01) |
| A61B 3/10 | (2006.01) |
| G06T 11/00 | (2006.01) |
| A61B 3/12 | (2006.01) |
| G06T 7/00 | (2017.01) |

(52) U.S. Cl.
CPC ............ *A61B 3/102* (2013.01); *A61B 3/1225* (2013.01); *G06K 9/00604* (2013.01); *G06T 7/0012* (2013.01); *G06T 11/008* (2013.01); *G06T 2207/10101* (2013.01); *G06T 2207/30041* (2013.01)

(58) Field of Classification Search
USPC ........ 382/100, 103, 128–134, 154, 162, 168, 382/173, 181, 199, 203, 220, 224, 254, 382/274, 276, 285–291, 305, 153; 351/206; 600/425; 378/4, 21
See application file for complete search history.

(56) References Cited

U.S. PATENT DOCUMENTS

| 8,556,424 B2 | 10/2013 | Iwase et al. |
| 8,634,081 B2 | 1/2014 | Suehira et al. |
| 8,657,440 B2 | 2/2014 | Iwase et al. |
| 8,840,248 B2 | 9/2014 | Imamura |
| 8,861,817 B2 | 10/2014 | Imamura et al. |
| 9,004,685 B2 | 4/2015 | Iwase et al. |
| 9,025,844 B2 | 5/2015 | Iwase et al. |

(Continued)

FOREIGN PATENT DOCUMENTS

| JP | 2016-028666 A | 3/2016 |
| JP | 2017-006179 A | 1/2017 |

*Primary Examiner* — Seyed H Azarian
(74) *Attorney, Agent, or Firm* — Venable LLP

(57) ABSTRACT

An image processing apparatus including an identification unit configured to identify a lamina cribrosa region by analyzing tomographic image data on an eye to be inspected, a generation unit configured to generate a luminance en face image and a motion contrast en face image of the eye to be inspected by using information on the identified lamina cribrosa region, and a display control unit configured to cause a display unit to display at least one of the luminance en face image and the motion contrast en face image with the information on the identified lamina cribrosa region superimposed on the displayed image.

18 Claims, 38 Drawing Sheets

(56) References Cited

U.S. PATENT DOCUMENTS

| | | |
|---|---|---|
| 9,098,742 B2 | 8/2015 | Yonezawa et al. |
| 9,307,903 B2 | 4/2016 | Imamura |
| 9,320,424 B2 | 4/2016 | Imamura |
| 9,351,650 B2 | 5/2016 | Uji et al. |
| 9,355,446 B2 | 5/2016 | Imamura et al. |
| 9,820,650 B2 | 11/2017 | Uji et al. |
| 9,848,769 B2 | 12/2017 | Miyasa et al. |
| 9,934,435 B2 | 4/2018 | Imamura |
| 9,943,224 B2 | 4/2018 | Imamura et al. |
| 10,152,807 B2 | 12/2018 | Kuno et al. |
| 2011/0137157 A1 | 6/2011 | Imamura et al. |
| 2012/0150029 A1* | 6/2012 | Debuc .................. G06T 7/12 600/425 |
| 2013/0194546 A1* | 8/2013 | Iwase .................. G06T 7/0012 351/206 |
| 2013/0258285 A1* | 10/2013 | Iwase .................. G06T 7/0012 351/206 |
| 2014/0016096 A1 | 1/2014 | Iwase et al. |
| 2014/0333749 A1 | 11/2014 | Imamura |
| 2014/0362344 A1* | 12/2014 | Imamura ............ A61B 3/102 351/206 |
| 2016/0019691 A1* | 1/2016 | Imamura .............. G06T 5/50 382/128 |
| 2016/0371836 A1 | 12/2016 | Kuno et al. |
| 2017/0273557 A1 | 9/2017 | Nakazawa et al. |
| 2018/0000338 A1 | 1/2018 | Imamura |
| 2018/0000341 A1 | 1/2018 | Tomatsu et al. |
| 2018/0012353 A1 | 1/2018 | Imamura |
| 2018/0070815 A1 | 3/2018 | Miyasa et al. |
| 2018/0173950 A1 | 6/2018 | Imamura |

* cited by examiner

Reference

Target1

FIG. 31

IMAGE PROCESSING APPARATUS, IMAGE PROCESSING METHOD, AND NON-TRANSITORY COMPUTER READABLE MEDIUM

BACKGROUND OF THE INVENTION

Field of the Invention

The disclosed technology relates to an image processing apparatus, an image processing method, and a non-transitory computer readable medium.

Description of the Related Art

Use of a tomographic image capturing apparatus that captures a tomographic image of an eye portion, such as optical coherence tomography (OCT), allows three-dimensional observation of the state of the interior of the retina layer. The tomographic image capturing apparatus is useful for more accurate disease diagnosis and therefore widely used for ophthalmic treatment. One form of OCT is, for example, time domain OCT (TD-OCT), which is the combination of a wideband light source and a Michelson interferometer. TD-OCT is adapted to measure light that interferes with backscattered light acquired with a signal arm by moving the position of a reference mirror at a fixed speed and produce a reflected light intensity distribution in the depth direction. It is, however, difficult to acquire images at high speed because TD-OCT requires mechanical scanning. To overcome the difficulty, spectral domain OCT (SD-OCT) and swept source OCT (SS-OCT) have been developed as higher-speed image acquisition methods. In SD-OCT, a wideband light source is used and an interference signal is acquired with a spectrometer, and in SS-OCT, a high-speed wavelength sweeping light source is used for temporal spectrometry. SD-OCT and SS-OCT allow acquisition of wider-angle, large-invasion-depth tomographic images.

On the other hand, in ophthalmic treatment, to grasp the state of a disease of fundus blood vessels, invasive fluorescence contrast fundus examination has been performed. In recent years, an OCT angiography (hereinafter referred to as OCTA), in which OCT is used to three-dimensionally extract fundus blood vessels in a noninvasive manner, has been used. In OCTA, a same position is scanned with measurement light multiple times, and motion contrast produced by interaction between displacement of red-blood cells and the measurement light is captured in the form of an image. FIG. 4A illustrates an example of OCTA imaging in which B-scan, which is formed of primary scan in the horizontal direction (x-axis direction) and secondary scan (in y-axis direction), is performed for successive r times in each position (yi: $1 \leq i \leq n$) in the secondary scan direction. Scanning a same position multiple times in the OCTA imaging is called cluster scan, and a plurality of tomographic images generated in the same position is called a cluster. Motion contrast images are generated on a cluster basis, and it is known that the lager the number of tomographic images per cluster, the higher the contrast of a generated OCTA image.

FIG. 4B illustrates an example of captured tomographic images of the fundus optic papilla. Porous collagen tissue called a lamina cribrosa portion L is present below excavatio papillae C, and each pore is a called lamina pore. It is known that deformation of the lamina cribrosa causes failure of the axon of a ganglion cell passing through a lamina pore, resulting in the glaucoma. One method for capturing an image of the lamina cribrosa portion at high contrast is enhanced depth imaging (EDI), and a coherence gate is set in the choroid or the lamina cribrosa for tomographic image capturing.

Japanese Patent Application Laid-Open No. 2016-28666 discloses a technology for setting a front surface region and a rear surface region of the lamina cribrosa based on OCT tomographic images of an eye portion and producing shape information on the lamina cribrosa, such as the thickness of the lamina cribrosa, based on the front surface region and the rear surface region.

One factor that causes deformation of the lamina cribrosa is, for example, retraction of blood-perfusion blood vessels in the lamina cribrosa. To grasp retraction of the blood vessels, it is conceivable to identify a perfusion area (blood vessel area) from an OCTA image by using image processing and quantify the perfusion area by calculating the blood vessel density. That is, it is desired not only to grasp the shape of the lamina cribrosa portion but grasp the relation between the shape of the lamina cribrosa portion and the distribution of the blood-perfusion blood vessels in the lamina cribrosa portion.

SUMMARY OF THE INVENTION

The disclosed technology has an object that is to readily grasp the relationship between the shape of a predetermined site, such as a lamina cribrosa portion, and the distribution of blood-perfusion blood vessels in the predetermined site.

In addition to the object described above, providing an advantageous effect that is derived from each configuration illustrated in forms described later for implementing the present invention and is not provided by related art can be regarded as another object of the present specification.

A disclosed image processing apparatus for achieving the object described above includes an identification unit configured to identify a lamina cribrosa region by analyzing tomographic image data on an eye to be inspected, a generation unit configured to generate a luminance en face image and a motion contrast en face image of the eye to be inspected by using information on the identified lamina cribrosa region, and a display control unit configured to cause a display unit to display at least one of the luminance en face image and the motion contrast en face image with the information on the identified lamina cribrosa region superimposed on the displayed image.

Further features of the present invention will become apparent from the following description of exemplary embodiments with reference to the attached drawings.

BRIEF DESCRIPTION OF THE DRAWINGS

FIG. 31 describes an image display screen.

DESCRIPTION OF THE EMBODIMENTS

Preferred embodiments of the present invention will now be described in detail in accordance with the accompanying drawings.

First Embodiment

An image processing apparatus according to the present embodiment displays a superimposed luminance front image formed of OCT tomographic images containing a lamina cribrosa portion acquired in EDI imaging and a motion contrast front image of the lamina cribrosa portion generated from the OCTA superimposed image with the two images displayed side by side or superimposed on each other. The description will then be made of how to readily grasp the relationship between the shape of the lamina cribrosa portion and the distribution of blood-perfusion blood vessels in the lamina cribrosa portion. In the present invention, the EDI imaging, image superimposition, and the like are not essential.

An image processing system including the image processing apparatus according to the first embodiment of the present invention will be described below with reference to the drawings.

Figure 2A:
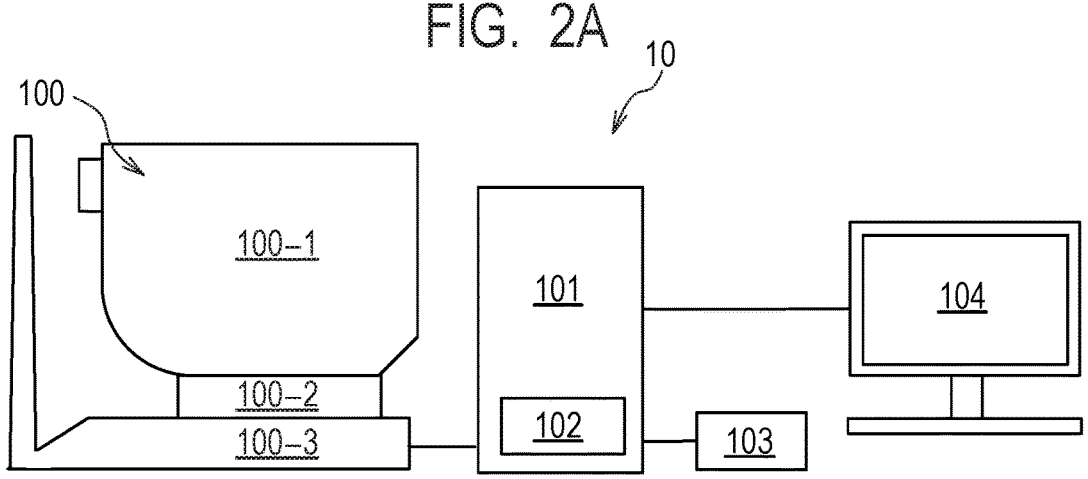
FIG. 2A describes an image processing system according to the first embodiment.

FIG. 2A illustrates the configuration of an image processing system 10 including an image processing apparatus 101 according to the present embodiment. The image processing system 10 is so adapted that the image processing apparatus 101 is connected to a tomographic image capturing apparatus 100 (also called OCT), an external storage unit 102, an input unit 103, and a display unit 104 via interfaces, as illustrated in FIG. 2A.

The tomographic image capturing apparatus 100 is an apparatus that captures tomographic images of an eye portion. In the present embodiment, it is assumed that SD-OCT is used as the tomographic image capturing apparatus 100, but not necessarily. For example, the tomographic image capturing apparatus 100 may instead be adapted by using SS-OCT.

In FIG. 2A, a measurement optical system 100-1 is an optical system for acquiring an anterior eye portion image, an SLO fundus image of an eye to be inspected, and tomographic images. A stage unit 100-2 allows the measurement optical system 100-1 to move frontward, rearward, rightward, and leftward. A base unit 100-3 has a built-in spectrometer that will be described later.

The image processing apparatus 101 is a computer that controls the stage unit 100-2, controls alignment, and reconstructs tomographic images. The external storage unit 102 stores a program for tomographic imaging, patient information, imaging data, image data and measurement data on past examinations, and other pieces of information.

The input unit 103 issues an instruction to the computer and is specifically formed of a keyboard and a mouse. The display unit 104 is formed, for example, of a monitor.

(Configuration of Tomographic Image Capturing Apparatus)

Figure 2B:
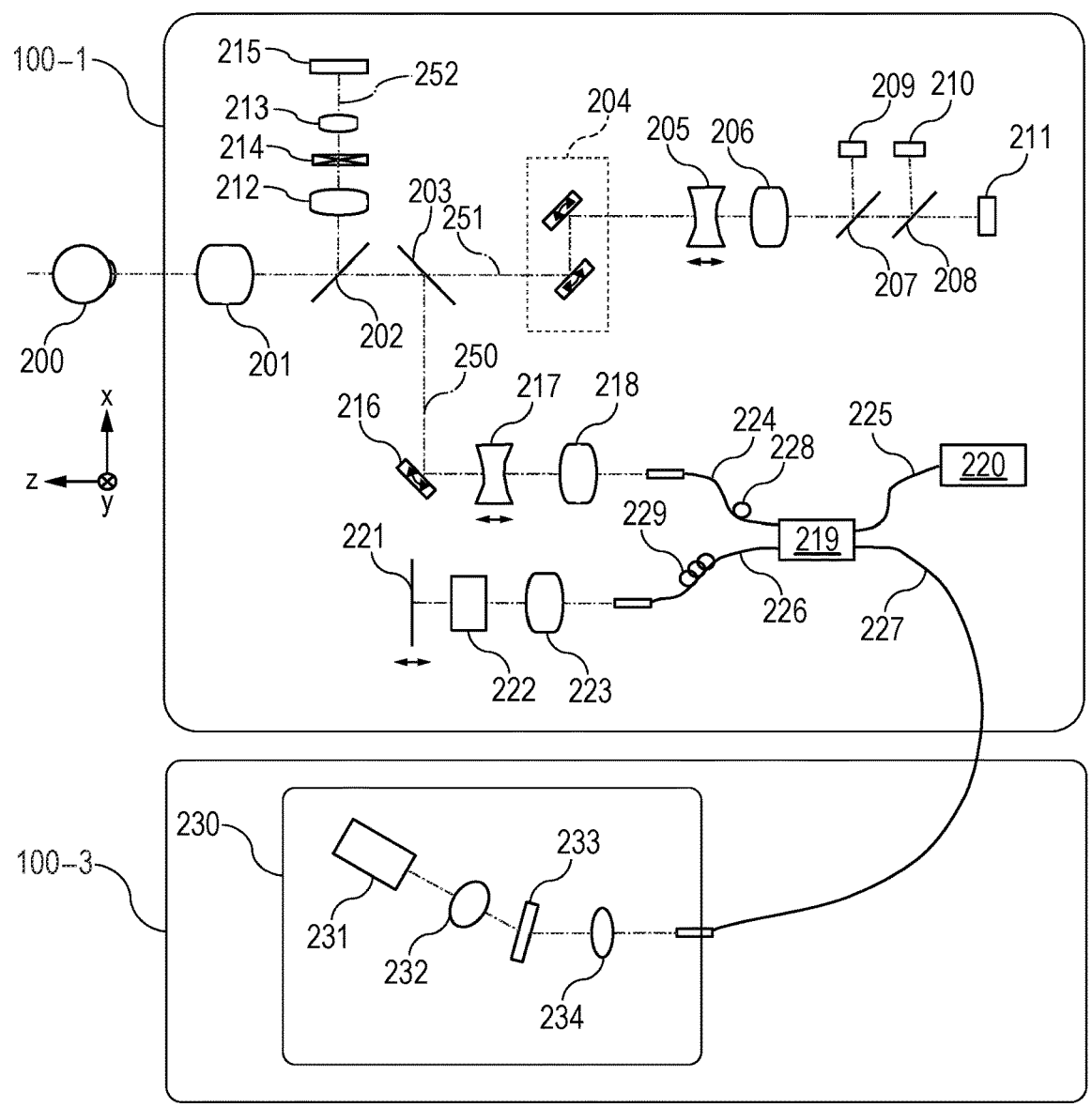
FIG. 2B describes a measurement optical system provided in a tomographic image capturing apparatus that forms the image processing system according to the first embodiment.

The configurations of the measurement optical system and the spectrometer in the tomographic image capturing apparatus 100 according to the present embodiment will be described with reference to FIG. 2B.

The interior of the measurement optical system 100-1 will first be described. An objective lens 201 is so disposed as to face an eye to be inspected 200, and a first dichroic mirror 202 and a second dichroic mirror 203 are disposed along the optical axis of the objective lens 201. The dichroic mirrors divide on a wavelength band basis the optical path extending from the objective lens 201 into an optical path 250 of an OCT optical system, an optical path 251 of an SLO optical system and a fixation, and an optical path 252 for anterior eye observation.

The optical path 251 of the SLO optical system and the fixation includes an SLO scan unit 204, lenses 205 and 206, a mirror 207, a third dichroic mirror 208, an avalanche photodiode (APD) 209, an SLO light source 210, and a fixation 211.

The mirror 207 is a prism on which a holed mirror or a hollow mirror is deposited and separates illumination light from the SLO light source from light that returns from the eye to be inspected. The third dichroic mirror 208 separates the optical path of the SLO light source 210 and the optical path of the fixation 211 from each other on a wavelength band basis.

The SLO scan unit 204 scans the eye to be inspected 200 with the light emitted from the SLO light source 210 and is formed of a scanner X that performs X-diction scan and a scanner Y that performs Y-diction scan. In the present embodiment, the scanner X, which needs to perform high-speed scan, is a polygonal mirror, and the scanner Y is a galvanometric mirror.

The lens 205 is driven with a motor that is not illustrated to perform focusing of the light from each of the SLO light source and the fixation 211. The SLO light source 210 emits light having a wavelength of about 780 nm. The APD 209 detects light that returns from the eye to be inspected. The fixation 211 emits visible light to facilitate fixation of the vision of a subject.

The light emitted from the SLO light source 210 is reflected off the third dichroic mirror 208, passes through the mirror 207, passes through the lenses 206 and 205, and enters the SLO scan unit 204, which scan the eye to be inspected 200 with the light. The light that returns from the eye to be inspected 200 traces back the same path along which the illumination light travels, is then reflected off the mirror 207, and is guided to the APD 209, and a SLO fundus image can be acquired.

The light emitted from the fixation 211 passes through the third dichroic mirror 208 and the mirror 207, passes through the lenses 206 and 205, and enters the SLO scan unit 204, which forms a light spot having a predetermined shape in an arbitrary position on the eye to be inspected 200 to facilitate fixation of the vision of the subject.

Lenses 212 and 213, a splitting prism 214, and a CCD 215 for observation of an anterior eye portion, which senses infrared light, are disposed along the optical path 252 for anterior eye observation. The CCD 215 is sensitive to the wavelength of light that is not illustrated but is radiated for anterior eye portion observation, specifically, a wavelength of about 970 nm. The splitting prism 214 is disposed in a position conjugate to the pupil of the eye to be inspected 200, and the distance from the measurement optical system 100-1 to the eye to be inspected 200 in the Z-axis direction (optical axis direction) can be detected in the form of a split image of the anterior eye portion.

The optical path 250 for the OCT optical system forms the OCT optical system as described above and is intended to capture tomographic images of the eye to be inspected 200. More specifically, the optical path 250 for the OCT optical system is intended to produce an interference signal for forming tomographic images. An XY scanner 216 is intended to scan the eye to be inspected 200 with light and is drawn in the form of one mirror in FIG. 2B but is actually a galvanometric mirror that performs scanning in two axial directions or the directions XY.

Out of lenses 217 and 218, the lens 217 is driven with a motor that is not illustrated to bring the light that is emitted from an OCT light source 220 and exits out of a fiber 224 connected to an optical coupler 219 into focus on the eye to be inspected 200. The focusing described above also allows the light having returned from the eye to be inspected 200 to be focused at the front end of the fiber 224 in the form of a spot and enter the optical fiber 224. The optical path extending from the OCT light source 220 and the configurations of a reference optical system and the spectrometer will next be described. The OCT optical system is provided with the OCT light source 220, a reference mirror 221, a dispersion compensation glass plate 222, a lens 223, the optical coupler 219, single-mode optical fibers 224 to 227 connected to and integrated with the optical coupler, and a spectrometer 230.

The configuration described above forms a Michelson interferometer. The light emitted from the OCT light source 220 passes through the optical fiber 225 and is divided via the optical coupler 219 into the measurement-light traveling optical fiber 224 and the reference-light traveling optical fiber 226. The measurement light travels along the optical path of the OCT optical system described above, is radiated to the eye to be inspected 200, which is an observation target, is reflected off and scattered by the eye to be inspected 200, traces back the same optical path, and reaches the optical coupler 219.

On the other hand, the reference light reaches the reference mirror 221 via the optical fiber 226, the lens 223, and the dispersion compensation glass plate 222, which is inserted to match the measurement light and the reference light in terms of wavelength dispersion, and is reflected off the reference mirror 221. The reference light then traces back the same optical path and reaches the optical coupler 219.

The optical coupler 219 combines the measurement light and the reference light with each other into interference light.

The interference occurs when the optical path lengths of the measurement light and the reference light become substantially equal to each other. The reference mirror 221 is so held by a motor and a drive mechanism that are not illustrated as to be adjustable in the optical axis direction, whereby the optical path length of the reference light can match with the optical path length of the measurement light. The interference light is guided to the spectrometer 230 via the optical fiber 227.

Polarization adjustment units 228 and 229 are provided in the optical fibers 224 and 226, respectively, and adjust polarization. The polarization adjustment units each have several portions where the optical fiber is looped. Rotating the loop portions around the longitudinal direction of each of the optical fibers to twist the fiber allows adjustment of the polarization states of the measurement light and the reference light.

The spectrometer 230 is formed of lenses 232 and 234, a grating 233, and a linear sensor 231. The interference light having exited out of the optical fiber 227 is parallelized by the lens 234, then spectrally dispersed by the grating 233, and focused by the lens 232 onto the linear sensor 231.

The OCT light source 220 and portions therearound will next be described. The OCT light source 220 is a super luminescent diode (SLD), which is a representative low-coherence light source. The OCT light source 220 has a central wavelength of 855 nm and a wavelength bandwidth of about 100 nm. The bandwidth affects the optical-axial resolution of generated tomographic images and is therefore an important parameter.

Although an SLD is selected as the light source, the light source only needs to be capable of emitting low-coherence light, and amplified spontaneous emission (ASE) can, for example, instead be used. In view of the purpose of eye measurement, the central wavelength can fall within the near-infrared range. The central wavelength, which affects the lateral resolution of generated tomographic images, can be as short as possible. The central wavelength is set at 855 nm from the two reasons described above.

A Michelson interferometer is used as the interferometer in the present embodiment, and a Mach-Zehnder interferometer may instead be used. In accordance with the difference in the amount of light between the measurement light and the reference light, a Mach-Zehnder interferometer can be used in a case where the difference in the amount of light is large, whereas a Michelson interferometer can be used in a case where the difference in the amount of light is relatively small.

(Configuration of Image Processing Apparatus)

Figure 1:
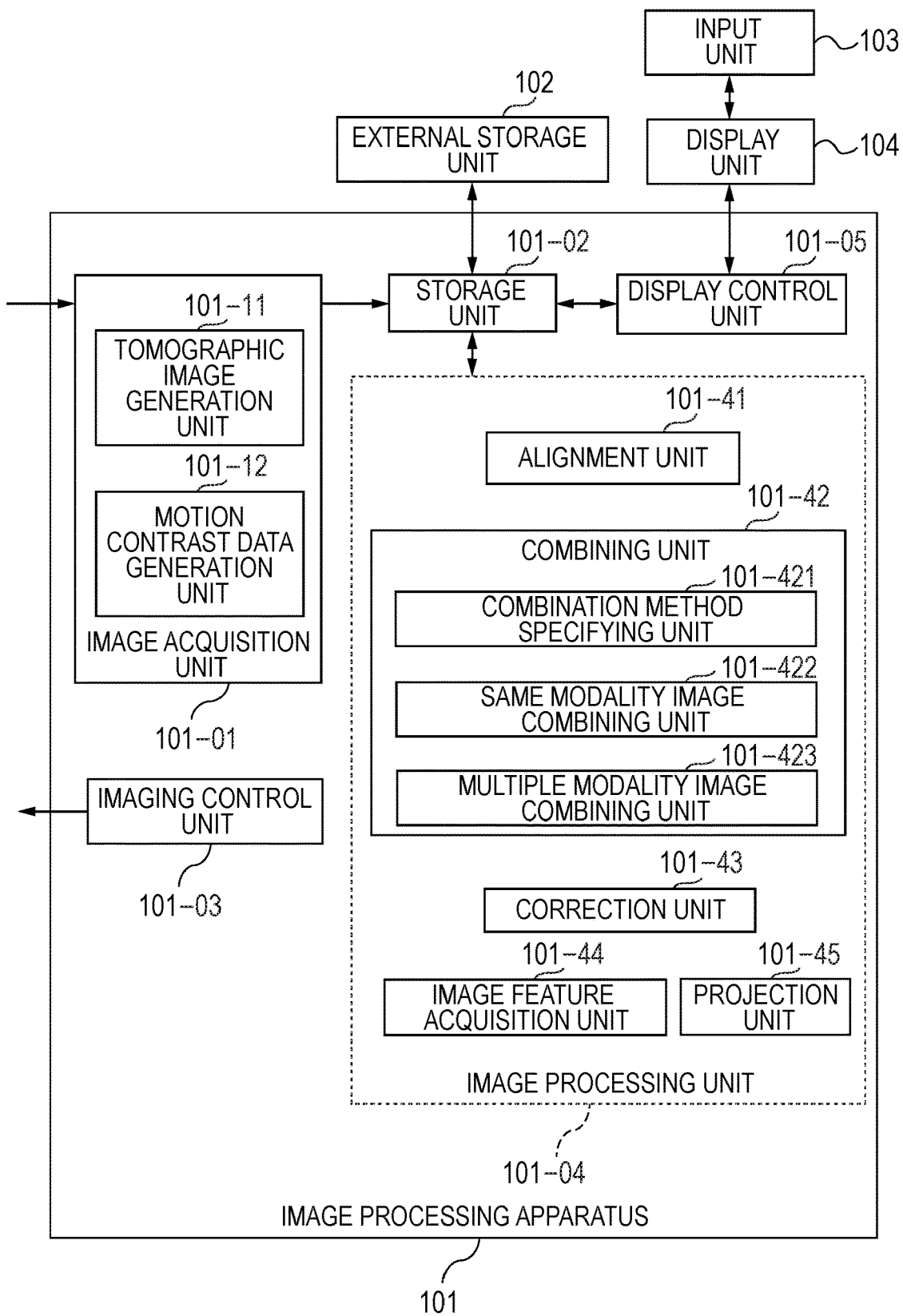
FIG. 1 is a block diagram illustrating the configuration of an image processing apparatus according to a first embodiment.

The configuration of the image processing apparatus 101 according to the present embodiment will be described with reference to FIG. 1.

The image processing apparatus 101 is a personal computer (PC) connected to the tomographic image capturing apparatus 100 and includes an image acquisition unit 101-01, a storage unit 101-02, an imaging control unit 101-03, an image processing unit 101-04, and a display control unit 101-05. In the image processing apparatus 101, a computation processor such as a CPU executes a software module that achieves the image acquisition unit 101-01, the imaging control unit 101-03, the image processing unit 101-04, and the display control unit 101-05 to achieve the functions thereof, but not necessarily in the present invention. For example, the image processing unit 101-04 may be achieved by dedicated hardware, such as an ASIC, and the display control unit 101-05 may be achieved by a dedicated processor, such as a GPU different from the CPU. Further, the tomographic image capturing apparatus 100 and the image processing apparatus 101 may instead be connected to each other via a network.

The image acquisition unit 101-01 acquires signal data on an SLO fundus image or tomographic images captured by the tomographic image capturing apparatus 100. The image acquisition unit 101-01 includes a tomographic image generation unit 101-11 and a motion contrast data generation unit 101-12. The tomographic image generation unit 101-11 acquires signal data (interference signal) on tomographic images captured by the tomographic image capturing apparatus 100 to generate tomographic images by performing signal processing thereon and stores the generated tomographic images in the storage unit 101-02.

The imaging control unit 101-03 controls the imaging performed by the tomographic image capturing apparatus 100. The imaging control also includes issuing an instruction on imaging parameter setting to the tomographic image capturing apparatus 100 and issuing an instruction on start and stop of the imaging.

The image processing unit 101-04 includes an alignment unit 101-41, a combining unit 101-42, a correction unit 101-43, an image feature acquisition unit 101-44, and a projection unit 101-45. The image acquisition unit 101-01 and the combining unit 101-42 described above are an example of an acquisition unit according to the present embodiment. The combining unit 101-42 includes a combination method specifying unit 101-421, a same modality image combining unit 101-422, and a multiple modality image combining unit 101-423. The combining unit 101-42 combines same modality images or tomographic images-motion contrast images with each other based on an alignment parameter produced by the alignment unit 101-41. Specifically, the combination method specifying unit 101-421 specifies the type of combination target images (tomographic images/motion contrast images/tomographic image and motion contrast image) and a combining method (superimposition/stacking/side-by-side display). The same modality image combining unit 101-422 combines tomographic images or motion contrast images with each other. The multiple modality image combining unit 101-423 combines a tomographic image and a motion contrast image with each other. The correction unit 101-43 two-dimensionally or three-dimensionally removes a projection artifact that occurs in a motion contrast image (projection artifact with be described in step S304). The image feature acquisition unit 101-44 acquires the layer boundary of the retina or the choroid, the boundaries of the front and rear surfaces of the lamina cribrosa, and the positions of the fovea centralis and optic papilla center from tomographic images. The image feature acquisition unit 101-44 is an example of an identification unit that identifies a lamina cribrosa region by analyzing tomographic image data on the eye to be inspected. The lamina cribrosa region used herein may, for example, be a region containing a region defined by the front and rear surfaces of the lamina cribrosa. The projection unit 101-45 projects tomographic images or motion contrast images over a depth range based on a boundary position acquired by the image feature acquisition unit 101-44 to generate a luminance front image or a motion contrast front image. The projection unit 101-45 is an example of a generation unit that generates a luminance front image or a motion contrast front image of the eye to be inspected by using information (coordinates, for example) on the identified lamina cribrosa region. The information on the identified lamina cribrosa region can contain at least one of information on the position of the lamina cribrosa region in the depth direction of the eye to be inspected (coordinates in direction Z, for example) and information on the position of the identified lamina cribrosa region in a direction that intersects the depth direction (coordinates in directions X and Y, for example). At least one of the pieces of information described above can be changed in accordance with an operator's instruction performed, for example, on a displayed image. Since the operator's operability can thus be improved, whereby the relationship between the shape of a predetermined site, such as the lamina cribrosa portion, and the distribution of blood-perfusion blood vessels in the predetermined site can be readily grasped.

The display control unit 101-05 is an example of a display control unit that causes the display unit 104 to display at least one of the luminance front image and the motion contrast front image with the information on the identified lamina cribrosa region superimposed on the displayed image. For example, the display control unit 101-05 allows the display unit 104 to display the front image on which information representing the position of the lamina cribrosa region in the in-plane direction of the front image (line representing outer edge of lamina cribrosa region or color representing interior of lamina cribrosa region, for example) is superimposed. The relationship between the shape of a predetermined site, such as the lamina cribrosa portion, and the distribution of blood-perfusion blood vessels in the predetermined site can therefore be readily grasped. The information on the identified lamina cribrosa region can contain information representing the result of analysis of the lamina cribrosa region performed by using at least one of a plurality of tomographic image data sets. As a result, for example, at least one of the position of a perfusion area, the position of a non-perfusion area (non-blood vessel area), the shape of the non-perfusion area, the area of the perfusion area, the area of the non-perfusion area, the length of each blood vessel, the curvature of each blood vessel, and the density of the blood vessels obtained by using the plurality of tomographic image data sets for generating the motion contrast front image can be readily grasped. Further, for example, at least one of the position of the lamina cribrosa region, the position of a lamina pore region, the thickness of the lamina cribrosa region, and the area of the lamina pore region obtained by using the plurality of tomographic image data sets for generating the luminance front image can be readily grasped.

The external storage unit 102 holds information on the eye to be inspected (patient's name, age, gender, and the like), captured images (tomographic images and SLO image/OCTA image) and a combined image, imaging parameters, and parameters set by the operator with those pieces of information related to one another. The input unit 103 is, for example, a mouse, a keyboard, or a touch operation screen, and the operator issues an instruction to the image processing apparatus 101 and the tomographic image capturing apparatus 100 via the input unit 103.

Figure 3:
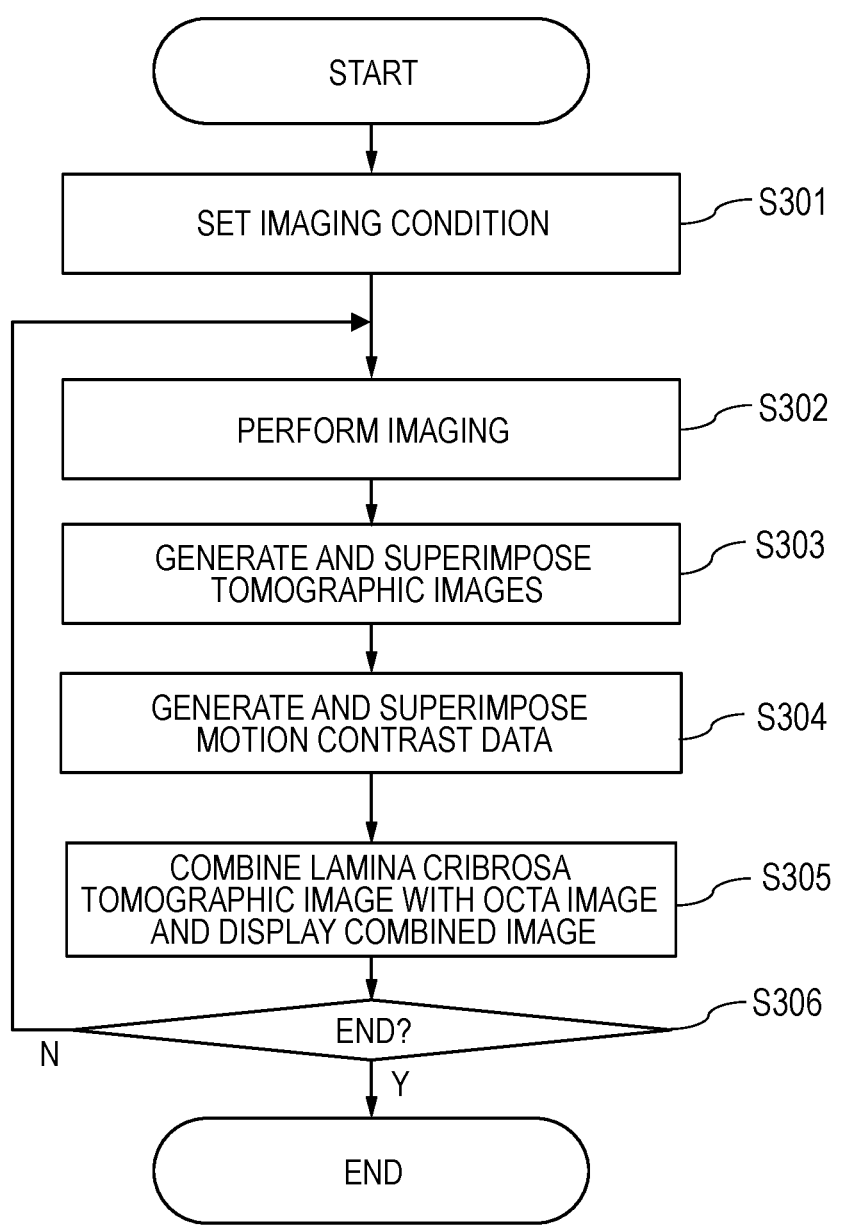
FIG. 3 is a flowchart of processes executable by the image processing system according to the first embodiment.

The procedure of processes carried out by the image processing apparatus 101 according to the present embodiment will next be described with reference to FIG. 3. FIG. 3 is a flowchart illustrating the flow of action processes carried out by the overall present system in the present embodiment.

<Step S301>

The operator operates the input unit 103 to set OCTA image capturing conditions to be issued as an instruction to the tomographic image capturing apparatus 100.

Specifically, setting the OCTA image capturing conditions are formed of:
 1) selecting or registering an examination set;
 2) selecting or adding a scan mode in the selected examination set; and
 3) setting imaging parameters corresponding to the scan mode.

In the present embodiment, the OCTA image capturing conditions are set as follows, and OCTA imaging is repeatedly performed by a predetermined number (under the same imaging conditions) in step S302 with an interval interposed between the imaging actions as appropriate:
 1) Register Disc examination set
 2) Select OCTA scan mode
 3) Set the following imaging parameters:
 3-1) Scan pattern: Medium square
 3-2) Scan size: 4×4 mm
 3-3) Scanning direction: Horizontal direction
 3-4) Distance between scans: 0.01 mm
 3-5) Fixation position: Optic papilla
 3-7) B scans per cluster: 4
 3-6) C-gate orientation: In choroid
 3-7) Type of default display report: Single examination report The examination set refers to an imaging procedure (including scan mode) set on an examination purpose basis and a default method for displaying an OCT image or an OCTA image acquired in each scan mode.

An examination set containing the OCTA scan mode, which has a glaucoma eye setting, is thus registered in the name of "Disc." The registered examination set is stored in the external storage unit 102.

In the present embodiment, "Disc" is selected as the examination set, and "OCTA" is selected as the scan mode.

<Step S302>

The operator operates the input unit 103 and presses an imaging start button (not illustrated) in an imaging screen to start repetitive OCTA imaging under the imaging conditions specified in step S301.

The imaging control unit 101-03 instructs the tomographic image capturing apparatus 100 to perform the repetitive OCTA imaging based on the setting instructed by the operator in step S301, and the tomographic image capturing apparatus 100 acquires corresponding OCT tomographic images.

In the present embodiment, the number of repetitive imaging actions in the present step is set at 3, but not necessarily, and the number of repetitive imaging actions can be set at an arbitrary number including one-shot imaging (no repetition). Further, the present invention is not limited to a case where the imaging interval between the repetitive imaging actions is longer than the imaging interval between the imaging actions of a tomographic image in each of the repetitive imaging actions, and a case where the two imaging intervals are substantially equal to each other falls within the scope of the present invention.

The tomographic image capturing apparatus 100 also acquires SLO images and performs tracking based on the SLO motion images. In the present embodiment, a reference SLO image used to perform the tracking in the repetitive OCTA imaging is a reference SLO image set in the first repetitive OCTA imaging, and the same reference SLO image is used in all repetitive OCTA imaging actions.

During the repetitive OCTA imaging, in addition to the imaging conditions set in step S301,
 Selection of one of the right and left eyes, and
 Whether or not the tracking is performed
are each the same setting (are each unchanged).

<Step S303>

The image acquisition unit 101-01 and the image processing unit 101-04 reconstruct the tomographic images acquired in step S302 and perform superimposition and projection to generate a superimposed luminance front image.

The tomographic image generation unit 101-11 first performs wave number conversion, fast Fourier transformation (FFT), and absolute value conversion (acquisition of amplitude) on the interference signal acquired by the image acquisition unit 101-01 to generate tomographic images corresponding to one cluster.

The alignment unit 101-41 then aligns tomographic images that belong to the same cluster with each other and then aligns inter-cluster tomographic images with each other. The combination method specifying unit 101-421 specifies tomographic images as the type of combination target images and superimposition as the combination method. The same modality image combining unit 101-422 uses the alignment parameter calculated by the alignment unit 101-41 to perform arithmetic averaging on tomographic images that belong to a plurality of clusters to generate superimposed tomographic images.

Further, the image feature acquisition unit 101-44 acquires layer boundary data and a front surface region B6 and a rear region B7 of the lamina cribrosa portion from the superimposed tomographic images. In the present embodiment, the following portions are acquired as the layer boundaries: an inner limiting membrane B1; a nerve fiber layer-ganglion cell layer boundary B2; a ganglion cell layer-inner plexiform layer boundary B3; an inner plexiform layer-inner nuclear layer boundary (not illustrated); an inner nuclear layer-outer plexiform layer boundary (not illustrated); a photoreceptor cell inner segment-outer segment joint B4; and a retinal pigmented epithelium-Bruch's membrane boundary B5. The end of the detected retinal pigmented epithelium-Bruch's membrane boundary B5 (Bruch's membrane opening end BMO) is identified as the boundary of an optic papilla (Disc) region D. In the present embodiment, the region inside the optic papilla region D in the in-plane direction and surrounded by the front surface region B6 and the rear surface region B7 of the lamina cribrosa in the depth direction is identified as the lamina cribrosa region. In the present embodiment, a variable shape model is used as a method for acquiring the layer boundaries and the front surface region B6 and the rear surface region B7 of the lamina cribrosa portion, and an arbitrary known segmentation approach may instead be used. Still instead, the boundary of the optic papilla region D and the front surface region B6 and the rear surface region B7 of the lamina cribrosa portion may be manually set. For example, the front surface region B6 and the rear surface region B7 of the lamina cribrosa portion can be manually set by moving the position of a specific layer boundary (inner limiting membrane B1, for example) by a predetermined amount.

The projection unit 101-45 projects the superimposed tomographic images within a depth range based on the position acquired by the image feature acquisition unit 101-44 to generate a superimposed luminance front image.

In the present embodiment, the superimposed luminance front image is generated within the depth range surrounded by the nerve fiber layer (B1 to B2) in the portion outside the optic papilla region D and within the depth range surrounded by the front surface region B6 and the rear surface region B7 of the lamina cribrosa. In a case where there is a site where the front surface region B6 or the rear surface region B7 of the lamina cribrosa cannot be identified in the optic papilla D, the superimposed luminance front image may be generated, in the site, within a predetermined depth range defined by the distance from the inner limiting membrane B1. The projection depth range is not necessarily set as described above, and an arbitrary depth range may be set in accordance with a region of interest. As the projection method, one of maximum intensity projection (MIP) and average intensity projection (AIP) can be selected. In the present embodiment, the average intensity projection is used to perform the projection.

<Step S304>

The image acquisition unit 101-01 and the image processing unit 101-04 use the aligned OCT tomographic images generated in step S303 to generate a motion contrast image.

The motion contrast data generation unit 101-12 calculates motion contrast between adjacent tomographic images in the same cluster. In the present embodiment, a decorrelation value Mxz is determined as the motion contrast based on the following Expression (1):

$$Mxz = 1 - 2 \times \frac{Axz \times Bxz}{Axz^2 + Bxz^2} \qquad (1)$$

In Expression (1), Axz represents the amplitude (luminance) in the position (x, z) of tomographic image data A (complex number data having undergone FFT), and Bzx represents the amplitude (luminance) in the same position (x, z) of tomographic image data B. The relationship $0 \leq Mxz \leq 1$ is satisfied, and the greater the difference between the two amplitudes is, the closer to 1 Mxz is. The decorrelation computation indicated by Expression (1) is performed on arbitrary adjacent tomographic images (that belong to the same cluster), and an image having a pixel value equal to the average of the resultant (the number of tomographic images per cluster −1) motion contrast values is generated as a final motion contrast image.

In the description, the motion contrast is calculated based on the amplitude of complex number data having undergone the FFT, but the method for calculating the motion contrast is not limited to the method described above. For example, the motion contrast may be calculated based on information of the phase of the complex number data or based on information on both the amplitude and the phase. Still instead, the motion contrast may be calculated based on the real part or the imaginary part of the complex number data.

A decorrelation value is calculated as the motion contrast in the present embodiment, but the method for calculating the motion contrast is not limited to the method described above. For example, the motion contrast may be calculated based on the difference between two values or based on the ratio between two values.

Further, in the above description, a final motion contrast image is generated by determining the average of a plurality of acquired decorrelation values, but not necessarily in the present invention. For example, an image having a pixel value equal to the median or the maximum of a plurality of acquired decorrelation value may be generated as a final motion contrast image.

The image processing unit 101-04 three-dimensionally aligns the motion contrast image groups generated in the repetitive OCTA imaging and performs arithmetic averaging on the aligned motion contrast image groups to generate a high-contrast combined motion contrast image. Specifically, the combination method specifying unit 101-421 specifies motion contrast images as the type of combination target images and superimposition as the combination method, and the same modality image combining unit 101-422 performs arithmetic averaging on the motion contrast images. The combination is not limited to simple arithmetic averaging. For example, the luminance values of the motion contrast images may be arbitrarily weighted and then averaged, or an arbitrary statistic represented by a median may be calculated. Two-dimensional alignment also falls within the scope of the present invention.

The same modality image combining unit 101-422 may be adapted to determine whether or not a motion contrast image inappropriate for the combination is included and then perform the combination without the motion contrast image having been determined as inappropriate. For example, in a case where an evaluation value for each motion contrast image (average or median of decorrelation values, for example) does not fall within a predetermined range, the corresponding motion contrast image may be determined as inappropriate for the combination.

In the present embodiment, after the same modality image combining unit 101-422 three-dimensionally combines motion contrast images with one another, the correction unit 101-43 three-dimensionally removes a projection artifact that occurs in the motion contrast images.

The projection artifact used herein refers to a phenomenon in which motion contrast in blood vessels in the retina superficial layer contaminates a deeper layer and a high decorrelation value is detected in spite of no actual blood vessel in the deeper layer. The correction unit 101-43 removes a projection artifact having occurred in the three-dimensional combined motion contrast image. An arbitrary known projection artifact removal approach may be used. In the present embodiment, step-down exponential filtering is used. In the step-down exponential filtering, the process indicated by Expression (2) is performed on each A-scan data on the three-dimensional motion contrast image to remove a projection artifact.

$$D_E(x, y, z) = D(x, y, z) \cdot e^{\frac{\sum_{i=1}^{z-1} D_E(x,y,i)}{\gamma}} \quad (2)$$

In Expression (2), y represents an attenuation factor having a negative value, D(x, y, z) represents a decorrelation value before the projection artifact removal, and DE(x, y, z) represents a decorrelation value after the projection artifact removal.

The projection unit 101-45 projects the motion contrast images within the depth range equal to the depth range in step S303 based on the layer boundaries and the lamina cribrosa region (region surrounded by front surface B6 and rear surface B7 of lamina cribrosa and optic papilla boundary D) acquired in step S303 by the image feature acquisition unit 101-44 to generate a superimposed motion contrast front image. The projection method can be selected from the maximum intensity projection (MIP) and the average intensity projection (AIP). In the present embodiment, the maximum intensity projection is used to perform the projection.

Finally, the image processing apparatus 101 relates the acquired image groups (SLO images and tomographic images) and the data on the imaging conditions under which the images have been captured, the generated three-dimensional motion contrast images, the motion contrast front image, and the generation conditions associated therewith to the inspection time and date and information for identifying the eye to be inspected and save these pieces of information related to one another in the external storage unit 102.

<Step S305>

The display control unit 101-05 causes the display unit 104 to display the superimposed luminance front image and the superimposed tomographic images of the lamina cribrosa portion generated in step S303, the superimposed motion contrast front image of the lamina cribrosa portion generated in step S304, and information on the imaging conditions and combination conditions.

Figure 4A:
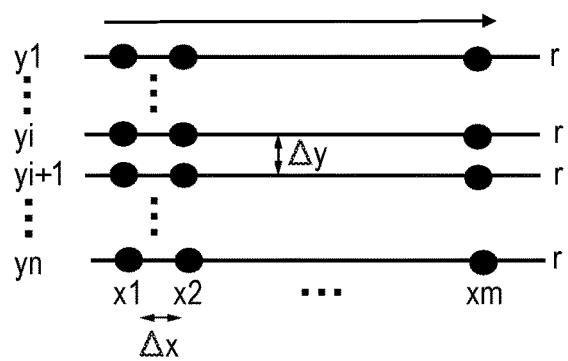
FIG. 4A describes a scan method for performing OCTA imaging performed in the first embodiment.
Figure 4B:
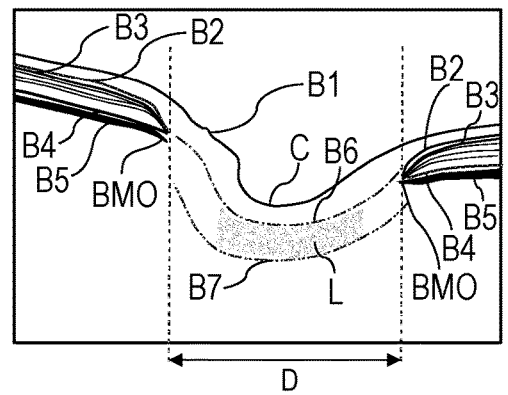
FIG. 4B describes an example of OCT tomographic images of the optic papilla.
Figure 4C:
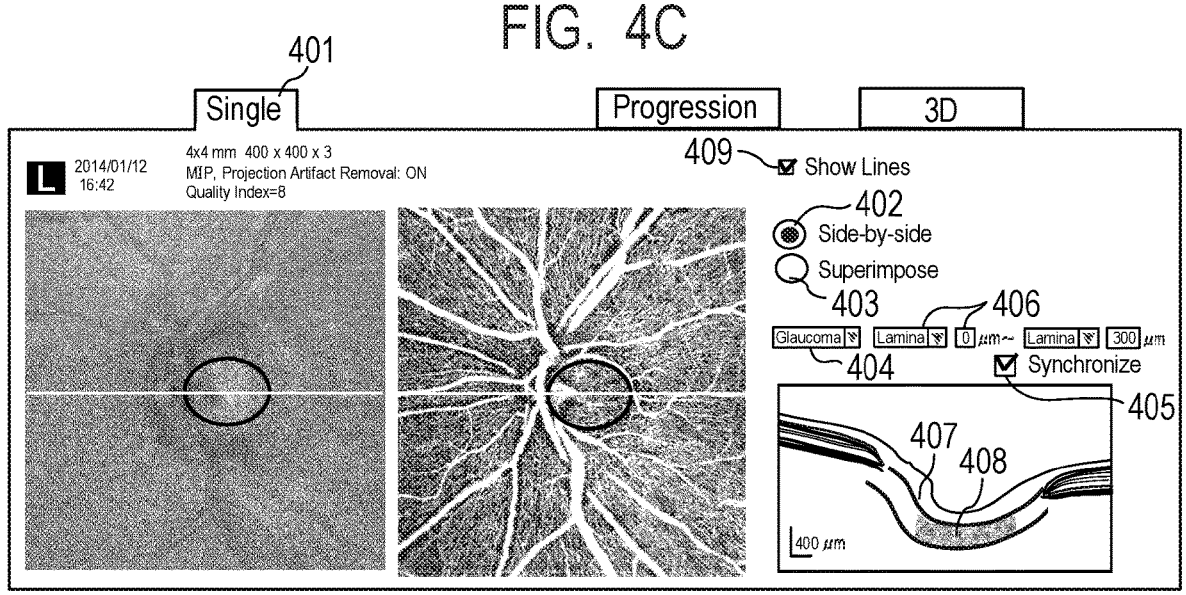
FIG. 4C and FIG. 4D describe an example of a report screen displayed on a display unit in step S305.

FIG. 4C illustrates an example of a report screen 401 in a single examination. In the present embodiment, the operator uses the input unit 103 to specify a side-by-side button 402 and thereby the combination method specifying unit 101-421 specifies "tomographic images and motion contrast images" as combination target images and side-by-side display as the combining method. The display control unit 101-05 displays the superimposed luminance front image in a left portion of the report screen and the superimposed motion contrast front image generated in step S304 in a right portion of the report screen based on the specified combination method.

In the superimposed luminance front image, the inside of the black circle shows the lamina cribrosa, and the outside the black circle shows the retinal inner layer (nerve fiber layer). In the superimposed motion contrast front image, the inside of the black circle shows blood-perfusion blood vessels in the lamina cribrosa portion, and the outside of the black circle shows retinal artery and vein and radial peripapillary capillaries (RPC) (distributed in nerve fiber layer). A B-scan image display region is provided in a lower right portion of the report screen, and a boundary 407, which represents the projection depth range of the tomographic images and the motion contrast images, and motion contrast data 408 are superimposed on B-scan tomographic images.

The side-by-side display described above allows detailed, clear observation of the lamina cribrosa and lamina pores in the left luminance front image and the distribution of the blood-perfusion blood vessels in the lamina cribrosa portion in the right motion contrast front image. Effects of the distribution of the blood-perfusion blood vessels in the lamina cribrosa portion on the shapes of the lamina cribrosa and the lamina pores (deformation) are therefore readily visually evaluated.

Outside the papilla, the nerve fiber layer can be observed in a detailed, clear manner in the left luminance front image, and the distribution of RPC in the right motion contrast front image, whereby the relation between the nerve fiber layer (aggregation of axons of ganglion cells) and the distribution of blood-perfusion capillaries in the nerve fiber layer is readily visually evaluated.

In the diagnosis of glaucoma, findings of an abnormal shape of the lamina cribrosa (factor that causes thinning of nerve fiber layer) and the thinning of the nerve fiber layer are important, and display of the abnormal shape in combination with the distribution of blood-perfusion blood vessels in each of the lamina cribrosa portion and the nerve fiber layer is useful as display setting for glaucoma diagnosis. The depth range outside the papilla and the blood vessels displayed in the portion outside the papilla are not limited to the nerve fiber layer and the RPC, respectively. For example, capillaries in the retinal superficial layer may be displayed within the projection depth range defined by the retinal superficial layer, or capillaries in the retinal deep layer may be displayed within the projection depth range defined by the retinal deep layer.

In a case where the operator desires to check the relative positional relationship between a partial region of the lamina cribrosa (or lamina pores) and the blood-perfusion capillaries in the lamina cribrosa portion, the operator may use the input unit 103 to specify the superimposition display (superimpose) button 403. The combination method specifying unit 101-421 specifies "tomographic images and motion contrast images" as combination target images and superimposition as the combining method. The multiple modality image combining unit 101-423 superimposes the luminance front image and the motion contrast front image on each other, and the display control unit 101-05 displays the superimposed image on the display unit 104. To display the luminance front image and the motion contrast front image superimposed on each other, the two images may be so displayed in the form of superimposition as to be distinguished from each other (in different colors or transparencies, for example). That is, one of the function of displaying the motion contrast front image or the result of analysis of the motion contrast front image and the luminance front image or the result of analysis of the luminance front image side by side and the function of displaying the images or the results superimposed on each other may be selectively performed in accordance with the operator's instruction. Therefore, since the operator's operability can be improved, whereby the relationship between the shape of a predetermined site, such as the lamina cribrosa portion, and the distribution of blood-perfusion blood vessels in the predetermined site can be readily grasped.

The projection depth ranges over which tomographic images and motion contrast images are projected can be changed by the operator as follows: That is, the operator selects any of the following modes from a default depth range setting 404 displayed in the form of a GUI, such as a list box:

Retinal superficial layer observation mode (depth range over predetermined distance from inner limiting membrane);

Retinal deep layer observation mode (depth range defined by retinal deep layer); and Glaucoma mode (lamina cribrosa portion: front surface and rear surface of lamina cribrosa, the other: retinal inner layer).

The projection range may instead be changed by selecting the type of boundary and the amount of offset used to specify the projection range, as illustrated by a projection range setting 406 in FIG. 4C, or operating the input unit 103 to move a layer superimposed on the B-scan tomographic images or the boundary 407 on the lamina cribrosa. In the present embodiment, one B-scan image display region is provided, and synchronizing the display slice numbers of a tomographic image and a motion contrast image with each other and synchronizing the projection depth range settings for the tomographic images and the motion contrast images are each a default action, but not necessarily in the present invention. For example, a B-scan image display region corresponding to the luminance front image and a B-scan image display region corresponding to the motion contrast front image may be separately provided, and the two images may each be displayed by using an arbitrary display slice number, and/or an arbitrary projection depth range may be set for each of the two images. Synchronization/asynchronization of the display slice number of the tomographic images with the display slice number of the motion contrast images and synchronization/asynchronization of the projection depth range setting for the tomographic images with the projection depth range setting for the motion contrast images may be configured to be selectable by providing the report screen with a GUI 405 for selection of synchronization or asynchronization. The projection depth range setting does not need to be fixed in an image. For example, a configuration in which separate settings inside and outside the region of interest (black frame) in FIG. 4C can be made may be employed, or a configuration in which separate settings inside and outside of the optic papilla boundary D can be made may be employed. As a method for making separate settings of the projection depth range on a region basis, for example, a position inside (or outside) the region of interest is specified via the input unit 103, and the type of the layer boundary used to specify the projection range and the amount of offset are then specified. Separate projection depth ranges can thus be set.

Figure 4D:
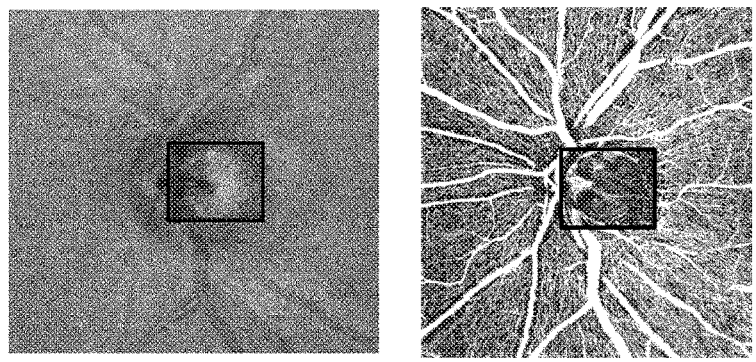

The method for generating a luminance front image and a motion contrast front image containing both a deep layer region such as the lamina cribrosa portion, and a superficial layer region, such as the nerve fiber layer, is not limited to the method based on switching the projection depth range on a region basis. For example, a luminance front image and a motion contrast front image may be generated by displaying a narrow viewing angle image containing the lamina cribrosa portion over the projection depth range defined by the front surface B6 and the rear surface B7 of the lamina cribrosa in such a way that the narrow viewing angle image is superimposed on a wide viewing angle image displayed over the projection depth range defined by the retinal superficial layer, as illustrated in FIG. 4D. Specifically, for example, the projection unit 101-45 generates a wide viewing angle image (tomographic images and motion contrast images) and a narrow viewing angle image containing the lamina cribrosa portion to be displayed over the entire projection depth range, and the alignment unit 101-41 calculates an alignment parameter for aligning the two images with each other. Further, the projection unit 101-45 generates wide viewing angle front images over the projection depth range defined by the retinal superficial layer and narrow viewing angle luminance front images containing the lamina cribrosa portion over the projection depth range defined by the front surface B6 and the rear surface B7 of the lamina cribrosa. The combination method specifying unit 101-421 specifies tomographic images (or motion contrast images) as combination target images and superimposition as the combining method. The multiple modality image combining unit 101-423 uses the alignment parameter to display the wide viewing angle front images over the projection depth range defined by the retinal superficial layer and the narrow viewing angle luminance front images containing the lamina cribrosa portion over the projection depth range defined by the front surface B6 and the rear surface B7 of the lamina cribrosa on the display unit 104 in the superimposition form.

The combination display region is not limited to the entire image. For example, the operator may use the input unit 103 to specify a combination target region, and only the image in the combination target region may be displayed on the display unit 104 in the superimposition or side-by-side form.

Tomographic images and motion contrast images displayed on the display unit 104 are not each limited to a front image and may instead each be displayed as a B-scan image in an arbitrary direction (two-dimensional luminance tomographic images) or three-dimensionally rendered three-dimensional images (three-dimensional luminance tomographic images or three-dimensional motion contrast images).

Further, the image projection method and whether or not the projection artifact removal is performed can be changed, for example, through selection from a user interface, such as a context menu. Motion contrast images having undergone the projection artifact removal may be displayed on the display 104 in the form of a front image, a B-scan image, or a three-dimensional image.

According to the configuration described above, the image processing apparatus 101 displays a superimposed front image formed of OCT tomographic images containing the lamina cribrosa portion acquired in EDI imaging and a motion contrast front image of the lamina cribrosa portion generated from an OCTA superimposed image in the side-by-side or superimposition form.

As a result, the relationship between the shape of the lamina cribrosa portion and the distribution of blood-perfusion blood vessels in the lamina cribrosa portion can be readily grasped.

Second Embodiment

An image processing apparatus according to the present embodiment generates a superimposed image formed of OCT tomographic images containing the lamina cribrosa portion acquired in EDI imaging, identifies the lamina cribrosa and the lamina pore region, and calculates the thickness of the lamina cribrosa and measurement values associated with lamina pores. Based on a motion contrast front image of the lamina cribrosa portion generated from the OCTA superimposed image, the perfusion area is identified, the blood vessel density is calculated, and the two image and the measured values acquired therefrom are displayed in the side-by-side or superimposition form. In the present invention, the EDI imaging, image superimposition, and the like are not essential. The description will then be made of how to readily grasp the relationship between the shape of the lamina cribrosa portion and the distribution of blood-perfusion blood vessels in the lamina cribrosa portion.

Figure 5:
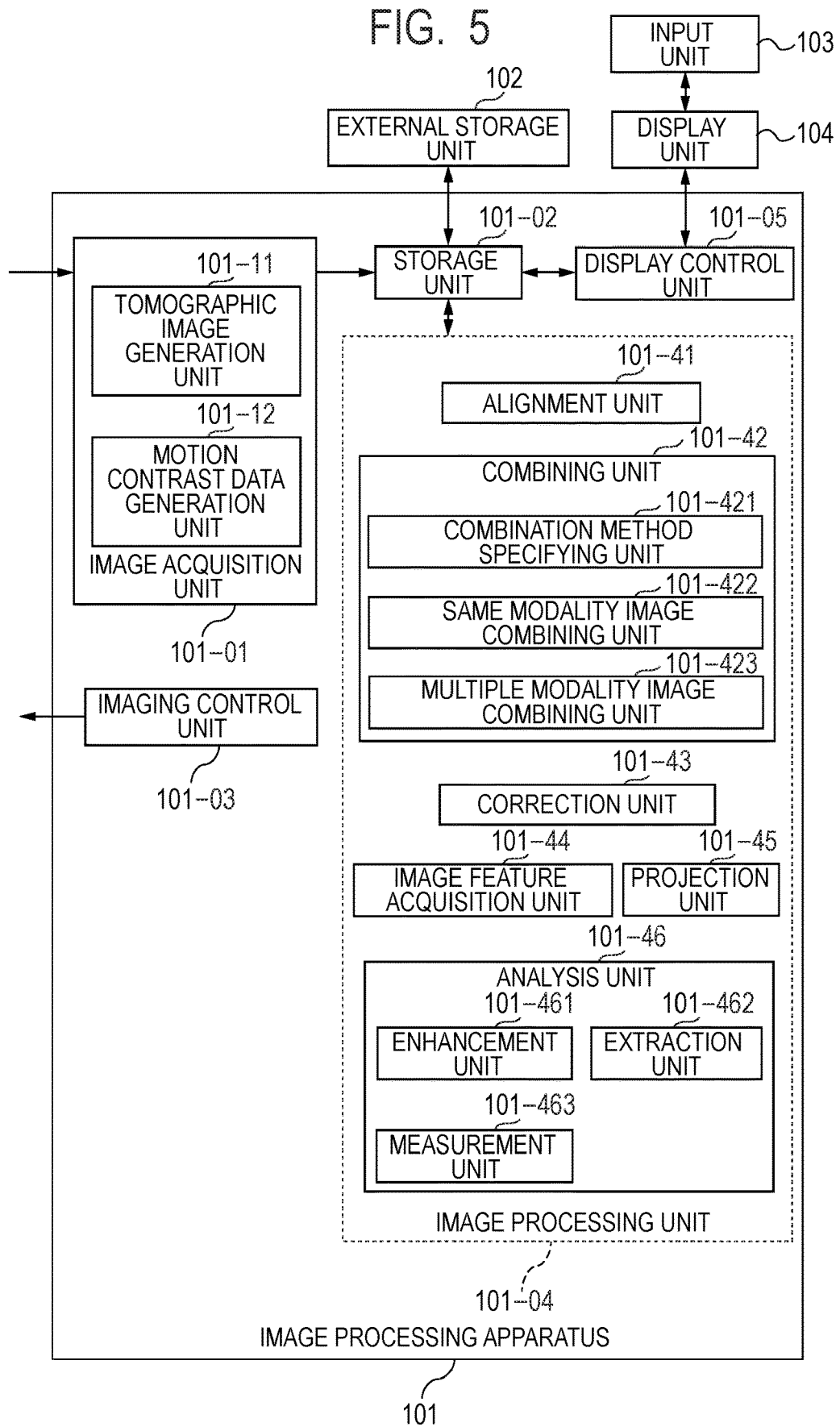
FIG. 5 is a block diagram illustrating the configuration of an image processing apparatus according to a second embodiment.

FIG. 5 illustrates the configuration of the image processing system 10 including the image processing apparatus 101 according to the present embodiment. The second embodiment differs from the first embodiment in that the image processing unit includes an analysis unit 101-46. The analysis unit 101-46 includes an enhancement unit 101-461, which performs image enhancement, an extraction unit 101-462, which performs segmentation, and a measurement unit 101-463, which calculates a measurement value associated with a segmented region.

In the present embodiment, the external storage unit 102 holds not only the information on the eye to be inspected, captured images and a combined image, the imaging parameters, and parameters set by the operator but data on the positions of the perfusion area, the lamina cribrosa, the lamina pore region, and the center line of each blood vessel and measurement values associated therewith with those pieces of information related to one another.

Figure 6:
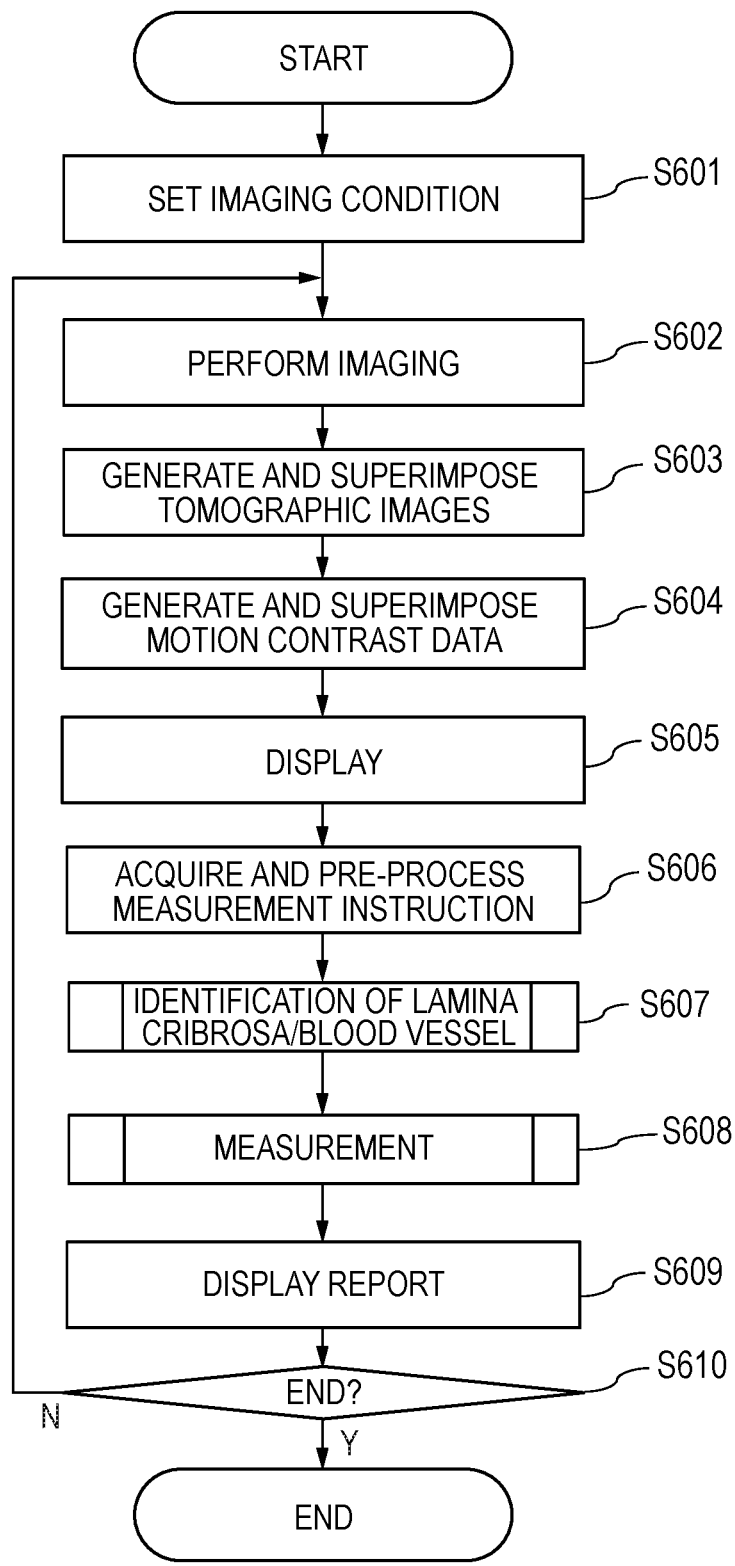
FIG. 6 is a flowchart of processes executable by an image processing system according to the second embodiment.

FIG. 6 illustrates the image processing flow in the present embodiment. In the image processing flow in the present embodiment, the steps in FIG. 6 excluding steps S606 to S609 are the same as those in the first embodiment and will not therefore be described.

<Step S606>

The operator uses the input unit 103 to instruct start of measurement.

Figures 8A, 8B, 8C, 8D, 8E, 8F, 8G, 8H, 8I, 8J:
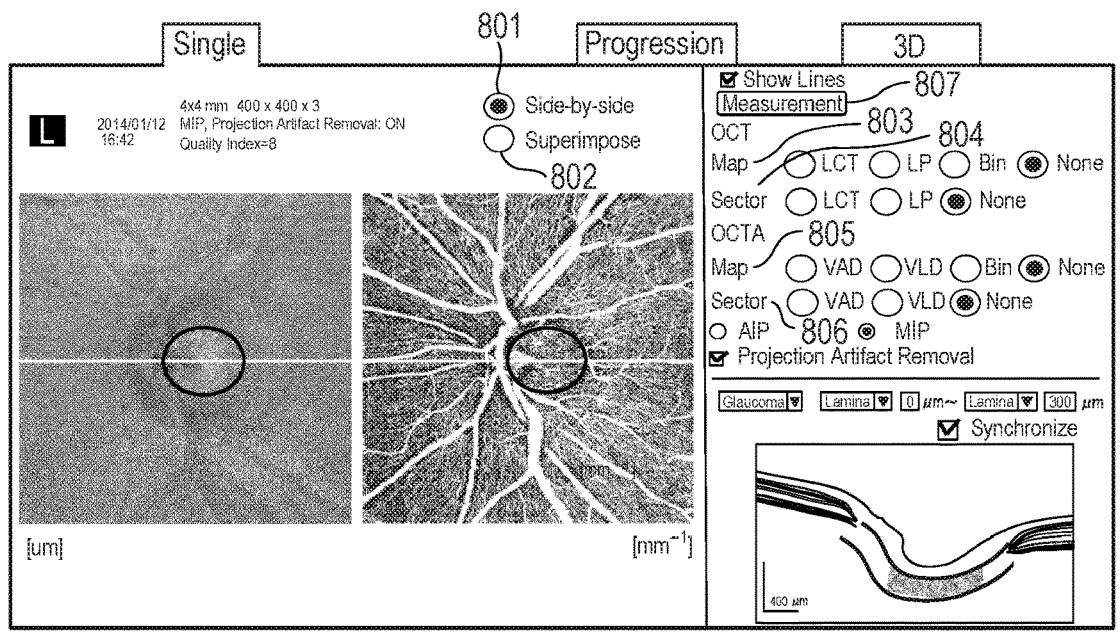
FIG. 8A describes measurement instruction operation in step S606 in the second embodiment.
FIG. 8B, FIG. 8C, FIG. 8D, and FIG. 8E describe image processing contents in step S607 in the second embodiment.
FIG. 8F, FIG. 8G, FIG. 8H, FIG. 8I, and FIG. 8J describe image processing contents in step S608 in the second embodiment.

In the present embodiment, the operator double clicks an image in the report screen in FIG. 4C to cause the current screen to transition to a measurement screen illustrated in FIG. 8A. An operation GUI associated with the tomographic images and motion contrast images is displayed when a side-by-side display button 801 is selected, and an operation GUI associated with the superimposed image is displayed when a superimposition display button 802 is selected. The operator then selects the type of image projection method, the projection depth range, and whether or not the projection artifact removal is performed as appropriate. The operator then selects an appropriate item from a selection screen (FIG. 9D) displayed via any of an OCT map button group 803, an OCT sector button group 804, an OCTA map button group 805, an OCTA sector button group 806, and a measurement button 807 in a right portion of FIG. 9A to select the type of measurement and a target region, and the analysis unit 101-46 starts the measurement.

It is assumed that "None" has been selected in the initial states of the OCT map button group 803, the OCT sector button group 804, the OCTA map button group 805, and the OCTA sector button group 806.

As the type of measurement, the measurement performed on the tomographic images in the present embodiment is selected from any of the following items in the OCT map button group 803:
  i) Measurement of lamina cribrosa thickness (LCT),
  ii) Measurement of lamina pore (LP) shape,
  iii) Lamina cribrosa region (Bin), and
  iv) None (no measurement),
and from any of the following items in the OCT sector button group 804:
  i) Measurement of lamina cribrosa thickness (LCT)
  ii) Measurement of lamina pore (LP) shape, and
  iii) None (no measurement).
For example, selection of None from the OCT map button group 803 or the OCT sector button group 804 means that no Map (entire image) or sector (sector region) is selected as a measurement target region where measurement is performed on the tomographic images.

As the measurement performed on the motion contrast images, any of the following items in the OCTA Map button group 805 is selected:
  i) blood vessel density (VAD),
  ii) blood vessel density (VLD),
  iii) perfusion area (Bin), and
  iv) None (no measurement),
and from any of the following items in the OCTA sector button group 806:
  i) blood vessel density (VAD),
  ii) blood vessel density (VLD), and
  iii) None (no measurement).
Selection of None from the OCTA map button group 805 or the OCTA sector button group 806 means that no Map (entire image) or sector (sector region) is selected as a measurement target region where measurement is performed on the motion contrast images, as in the measurement performed on the tomographic images.

The present embodiment will be described with reference to a case where "None" is selected as the OCT map, the lamina cribrosa thickness ("LCT") is selected as the OCT sector map, "None" is selected as the OCTA map, and "VLD" is selected as the OCTA sector map. The case described above corresponds to a case where measurement of the lamina cribrosa thickness is selected as the type of the measurement performed on the tomographic images, a sector region is selected as the tomographic image measurement target region, VLD is selected as the type of the measurement performed on the motion contrast images, and a sector region is selected as the motion contrast image measurement target region.

In the present embodiment, statistics on the areas of the pores (average and standard deviation/maximum/minimum) are calculated as the measurement of the lamina pores, but not necessarily. Arbitrary known measurement that provides values of measurement performed on the lamina pores, such as the diameter and the circularity of each of the lamina pores, may be performed.

The types of measurement performed on the tomographic images and motion contrast images are not limited to those described above. For example, calculation of the area and shape of the non-perfusion area (NPA) in the motion contrast images falls within the scope of the present invention.

VAD is an abbreviation of vessel area density and represents blood vessel density (unit: %) defined by the proportion of the perfusion area contained in a measurement target, and VLD is an abbreviation of vessel length density and represents blood vessel density defined by the sum of the lengths (unit: $mm^{-1}$) of blood vessels contained in a unit area.

The blood vessel densities are each an index for quantizing the range of vascular occlusion and the packing degree of the vascular network and VAD is most frequently used. In the case of VAD, however, since a large perfusion area greatly contributes to a measurement value, VLD (as an index more sensitive to capillary occlusion) is used in a case where it is desired to perform measurement focusing on the state of a disease of the capillaries.

In addition to the above, for example, a fractal dimension for quantizing the degree of complexity of the vascular structure and a vessel diameter index representing the distribution of the vascular diameter (distribution of blood vessel dilation and stenosis) may be measured.

The analysis unit 101-46 then performs pre-processing of the measurement. Arbitrary known image processing can be applied as the pre-processing. In the present embodiment, top-hat filtering, which is a kind of morphology operation, is performed on motion contrast images. Applying the top-hat filtering allows reduction in luminance unevenness in a background component.

<Step S607>

The analysis unit 101-46 identifies the lamina cribrosa region in a superimposed image of the tomographic images, identifies the lamina pore region in a superimposed front image of the tomographic image, and/or identifies the perfusion area in motion contrast images. In the present embodiment, the enhancement unit 101-461 performs blood vessel enhancement based on a Hessian filter on motion contrast images. The extraction unit 101-462 then performs segmentation on tomographic images, a tomographic front image, and a blood vessel enhancement image to shape the images to identify the lamina cribrosa, the lamina pores, and the perfusion area.

The identification of the lamina cribrosa, the lamina pores, and the perfusion area will be described in detail in the description of steps S6071 to S6078.

<Step 608>

The measurement unit 101-463 measures the shape of the lamina cribrosa and the blood vessel distribution in a single examination image based on information on the measurement target region specified by the operator. The display control unit 101-05 subsequently displays the result of the measurement on the display unit 104.

As the blood vessel density, which is the index of the blood vessel distribution, the two types of indices, VAD and VLD, are used. In the present embodiment, the procedure of calculation of VLD, which is an index more sensitive to failure of capillaries, will be described by way of example.

The measurement of the lamina cribrosa thickness in tomographic images and the lamina pore area in a tomographic front image will be described in the description of steps S6081 to S6083, and the measurement of VLD in motion contrast images will be described in the description of steps S6084 to S6087.

<Step S609>

The display control unit 101-05 displays a report on the measurement performed in step S608 on the display unit 104.

Figure 9A:
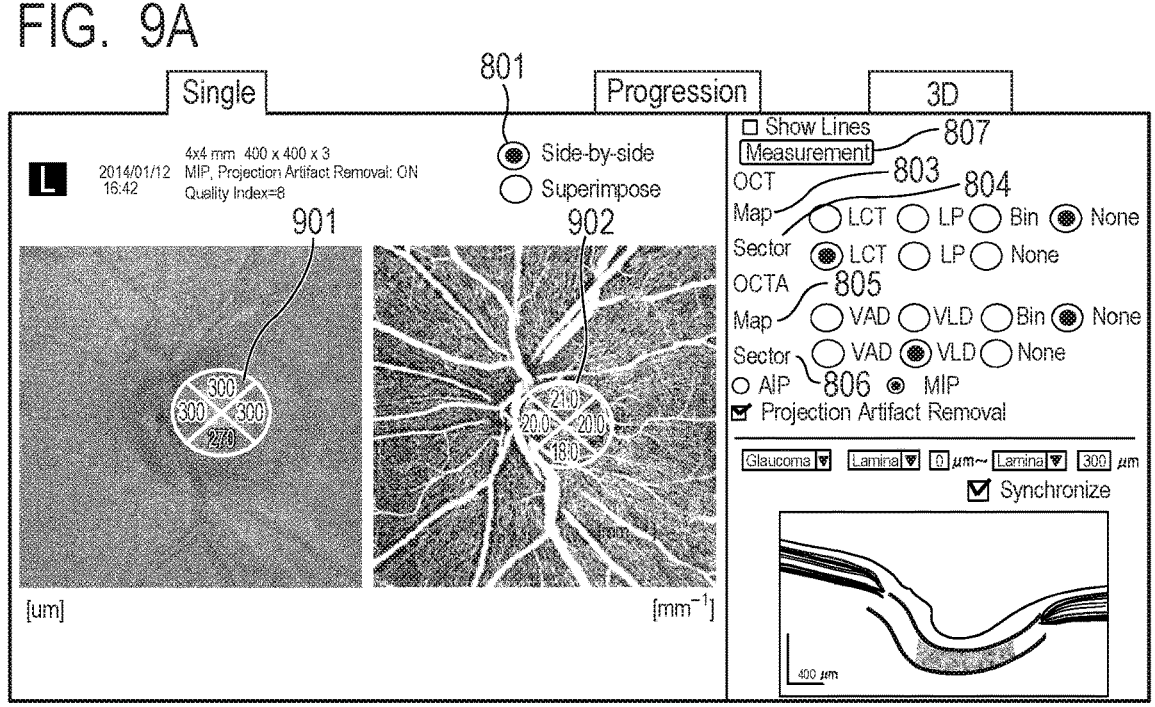
FIG. 9A, FIG. 9B, FIG. 9C, FIG. 9D, and FIG. 9E describe a measurement report screen displayed on a display unit in the second embodiment.

In the present embodiment, the side-by-side display button 801, "None" as the type of the measurement performed on the tomographic images (display content of measurement result) in the OCT map selection button 803, and "LCT" in the OCT sector map selection button 804 are selected in a single examination measurement report screen illustrated in FIG. 9A. Further, as the type of the measurement performed on the motion contrast images (display content of measurement result), "None" in the OCTA map selection button 805 and "VLD" in the OCTA sector map selection button 806 are selected. A tomographic front image and a lamina cribrosa thickness sector map, which is the result of the measurement of the lamina cribrosa portion, are superimposed and displayed in a left portion of the single examination measurement report, and a motion contrast image and a VLD sector map, which is the result of the measurement of the lamina cribrosa portion, are superimposed and displayed in a right portion of the single examination measurement report. The relationship between the distribution of the blood-perfusion blood vessels in the lamina cribrosa portion and the shape of the lamina cribrosa in each region is readily grasped.

In association with each measurement target image, the following pieces of information may be displayed on the display unit 104: selection of the right or left eye; the imaging time and date; the viewing angle and the number of pixels; the number of tomographic images in substantially the same position; information on conditions under which the OCTA superimposition has been performed; an evaluation value (quality index) of OCT tomographic images or motion contrast images; and/or information on whether or not the projection artifact removal has been performed.

In the present embodiment, the measurement value of the lamina cribrosa shape and the measurement value of the distribution of the blood-perfusion blood vessels in the lamina cribrosa portion are displayed side by side, but not necessarily in the present invention. For example, to accurately grasp the positional correspondence between a local shape of the lamina cribrosa and a local distribution of blood vessels, the superimposition display button 802 illustrated in FIG. 9B may be selected to superimpose and display the two measurement values. In the example illustrated in FIG. 9B, as the type of the measurement performed on the tomographic images (display content of measurement result), "None" is selected in the OCT map display button, and "LCT" is selected in the OCT sector map selection button 804. Further, as the type of the measurement performed on the motion contrast images (display content of measurement result), "VLD" is selected in the OCTA map selection button 805, and "None" is selected in the OCTA sector map selection button 806. A lamina cribrosa thickness sector map is superimposed and displayed on the VLD map associated with the lamina cribrosa portion. To superimpose and display the OCT map and the OCTA map, the two maps are so superimposed on each other and displayed that the two maps are distinguished from each other (in different colors or transparencies, for example). To superimpose and display the OCT sector map and the OCTA sector map, the numerals in the two sector maps are displayed side by side in the same sector, as illustrated in FIG. 9C. Numerals displayed side by side may be so written as to be distinguished from each other (accompanied by units or in different colors, font sizes, fonts, or thicknesses).

In the present embodiment, the description has been made of display of a region identified in the lamina cribrosa region in the portion inside the optic papilla boundary D (lamina cribrosa, lamina pores, and blood vessels) or a measurement value acquired in the lamina cribrosa region, but not necessarily in the present invention. For example, the present invention also encompasses a case where regions and measurement values identified or acquired in the lamina cribrosa region (region surrounded by front surface B6 and rear surface B7 of lamina cribrosa) in the portion inside the optic papilla boundary D and regions and measurement values identified or acquired in the depth range defined by the retinal superficial layer (nerve fiber layer, for example) in the portion outside the optic papilla boundary D. A specific example may be a case where the following two measurement value maps are displayed side by side: a measurement value map that displays "the lamina cribrosa thickness in the portion inside the optic papilla boundary D, the nerve fiber layer thickness (or ganglion cell layer thickness, ganglion cell complex (GCC) thickness) in the portion outside the optic papilla boundary D" is displayed in a left portion of the display unit 104; and a measurement map that displays "the blood vessel density (VLD or VAD) in the lamina cribrosa portion in the portion inside the optic papilla boundary D and the blood vessel density (VLD or VAD) in the RPC in the portion outside the optic papilla boundary D" is displayed in a right portion of the display unit 104. The side-by-side display described above (or superimposition display) allows not only grasp of the relation between the distribution of blood-perfusion blood vessels in the lamina cribrosa portion and a site of the lamina cribrosa where the shape thereof has changed but grasp of the relation between a site where the lamina cribrosa shape has changed and a region where nerve fiber layer has thinned. That is, a symptom that causes thinning of the nerve fiber layer and the ganglion cell layer (retraction of blood-perfusion blood vessels in the lamina cribrosa portion and resultant change in shape of lamina cribrosa portion) and a situation of ganglion cell death (thinning of nerve fiber layer and ganglion cell layer) resulting from the symptom can be listed and is therefore useful as display setting for glaucoma diagnosis. To display measurement value distributions acquired in the lamina cribrosa region in the portion inside the optic papilla boundary D and within the depth range of the retinal superficial layer in the portion outside the optic papilla boundary D on the display unit 104, only the measurement value map that displays "the lamina cribrosa thickness in the portion inside the optic papilla boundary D, the nerve fiber layer thickness (or ganglion cell layer thickness, ganglion cell complex (GCC) thickness) in the portion outside the optic papilla boundary D" may be displayed on the display unit 104, or only the measurement value map that displays "the blood vessel density in the lamina cribrosa portion in the portion inside the optic papilla boundary D, the blood vessel density in the RPC in the portion outside the optic papilla boundary D" may be displayed on the display unit 104. The depth range outside the papilla and blood vessels identified and measured in the portion outside the papilla are not limited to the nerve fiber layer and RPC, respectively. For example, capillaries in the retinal superficial layer may be identified and measured over the projection depth range defined by the retinal superficial layer, or capillaries in the retinal deep layer within the projection depth range defined by the retinal deep layer may be identified and measured and the distribution of the capillaries may be displayed. Further, the result of the identification and measurement of blood vessels displayed in the portion inside and outside the papilla is not necessarily displayed in the form of the blood vessel density. For example, the result may be displayed in the form of the position of the perfusion area, the position of the non-perfusion area, the shape of the non-perfusion area, the area of the perfusion area, the area of the non-perfusion area, the length of each blood vessel, and/or the curvature of each blood vessel.

Figure 9B:
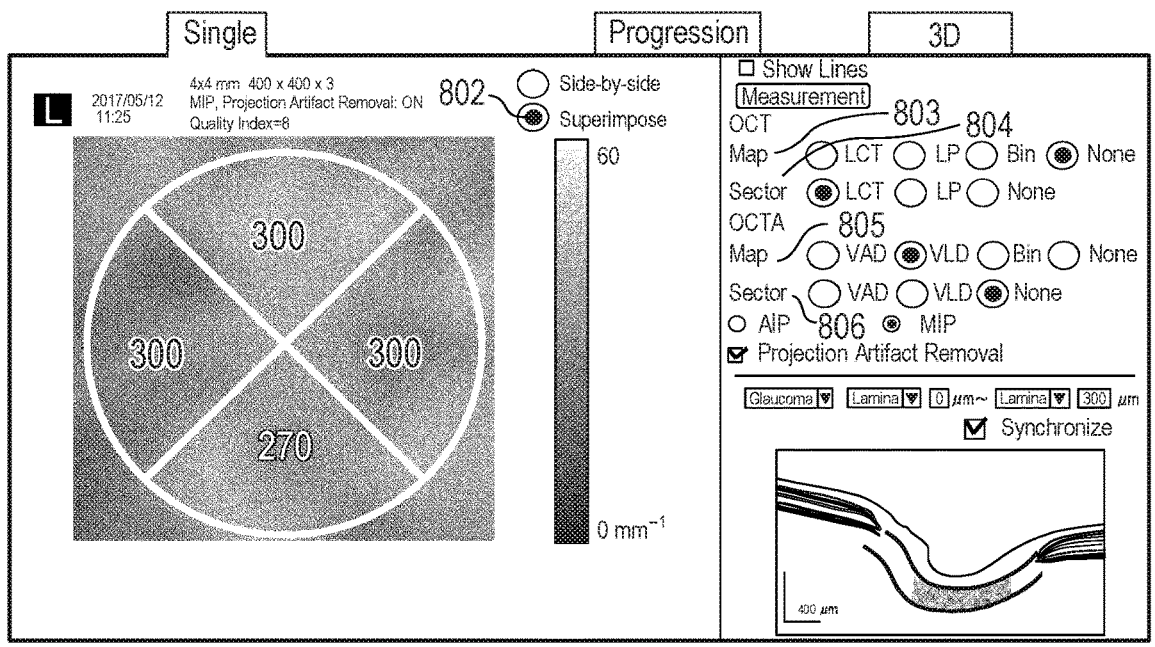
Figure 9C:
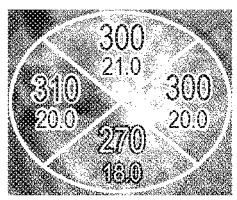

In FIG. 9A or FIG. 9B, "Bin" or "LP" may be selected in the OCT map selection button 803 to display the lamina cribrosa or the lamina pore region identified in step S607, or "Bin" may be selected in the OCTA map selection button 804 to display a binary image of the perfusion area on the display unit 104. The type of measurement in the present invention is not limited to those described above. For example, measurement of the non-perfusion area, the shape (length and circularity) of the non-perfusion area, the areas of the perfusion and non-perfusion areas, the blood vessel length, the blood vessel curvature, the area and shape (length and circularity) of each lamina pore also fall within the scope of the present invention.

Figure 9D:
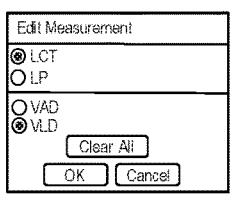
Figure 9E:
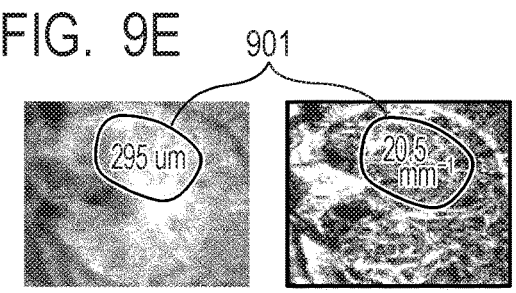

Further, the operator may select the type of measurement from the menu illustrated in FIG. 9D and displayed by specifying the button 807 in FIG. 9A (lamina cribrosa thickness (LCT) and VLD, for example), specify a region of interest having an arbitrary shape in tomographic images or motion contrast images to display the same region of interest 901 in the two images as illustrated in FIG. 9E, calculate a measurement value in each of the regions of interest, and display the calculated values side by side. In the case where the superimposition display button 802 has been selected, only one region of interest 901 is displayed in the single examination measurement report screen. In the case where only one region of interest 901 is displayed, a plurality of measurement values in the region of interest may be so displayed side by side as to be distinguished from one another (accompanied by units or in different colors, font sizes, fonts, or thicknesses).

Instead, tomographic images, motion contrast images, or a binary image of the front lamina cribrosa region, the lamina cribrosa region, the rear lamina cribrosa region, the lamina pore region, the perfusion area, or the blood vessel central line may be superimposed on one another and displayed on the display unit 104 with the color and transparency changed as appropriate on a predetermined depth range basis. Further, a tomographic image, or a binary image of the lamina cribrosa or the lamina pore region, and a motion contrast image, or a binary image of the perfusion area or the blood vessel central line is not necessarily displayed in the form of a front image and may instead be superimposed and displayed on a B-scan image or may be three-dimensionally rendered and displayed as a three-dimensional image in the side-by-side or superimposition form.

The combination display region is not limited to the entire image, as in the first embodiment. For example, the operator may use the input unit 103 to specify a combination target region, and only the image in the combination target region may be displayed on the display unit 104 in the superimposition or side-by-side form. For example, in the example illustrated in FIG. 9B, a rectangular region containing the lamina cribrosa portion is specified, and only the portion inside the rectangular region is displayed in the superimposition form. No region outside the combination target is displayed for ease of visual recognition of the measurement value distribution in the example illustrated in FIG. 9B, and both the combination target region and the region outside the combination target may instead be displayed on the display unit 104.

Further, the projection method (MIP/AIP) and the projection artifact removal may also be changed, for example, by a method based on selection from a context menu. Binary images of the lamina cribrosa region, the lamina pore region, and the perfusion area identified in step S607 and the measurement values and the measurement maps calculated in step S608 may each be output to and saved as a file in the external storage unit 102.

<Step S610>

The image processing apparatus 101 externally acquires an instruction of whether or not the series of processes from step S601 to S610 is terminated. The instruction is input by the operator via the input unit 103. When the image processing apparatus 101 acquires the process termination instruction, the image processing apparatus 101 terminates the processes. On the other hand, in a case where the image processing apparatus 101 acquires a process continuation instruction, the image processing apparatus 101 returns to the process in step S602 to carry out the following processes on the following eye to be inspected (or the same eye to be inspected again).

Figure 7B:
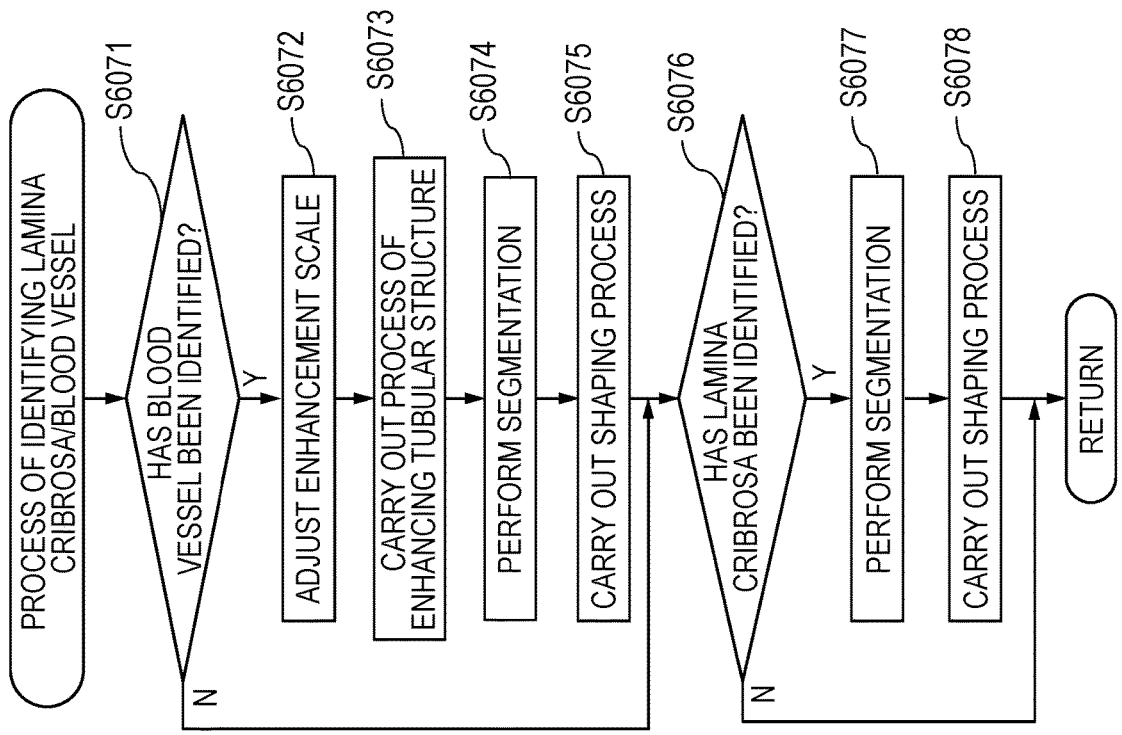
FIG. 7B is a flowchart illustrating processes carried out in step S608 in the second embodiment in detail.
Figure 7A:
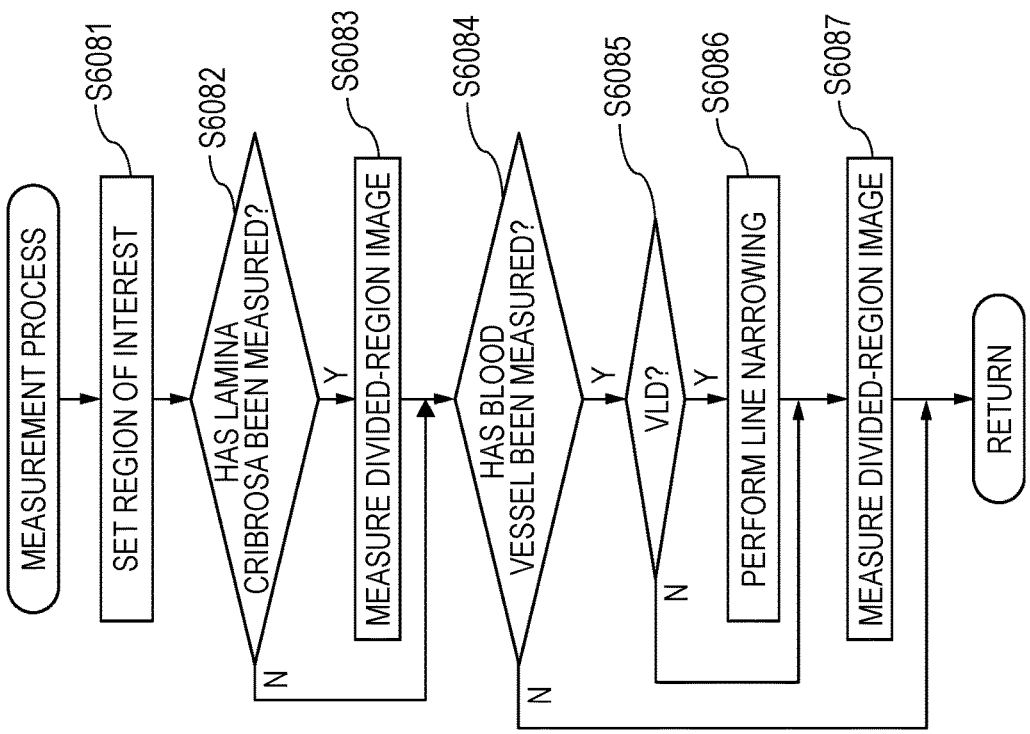
FIG. 7A is a flowchart illustrating processes carried out in step S607 in detail.

Further, the process carried out in step S607 will be described in detail with reference to the flowchart illustrated in FIG. 7A.

<Step S6071>

The analysis unit 101-46 evaluates whether or not the measurement content instructed by the operator's specification of the OCTA map selection button 805 and the OCTA sector map selection button 806 or the arbitrary shape ROI selection button 807 in FIG. 8A requires identification of the perfusion area. In a case where the result of the evaluation shows YES, the analysis unit 101-46 proceeds to the process in step S6072, whereas in a case where the result of the evaluation shows No, the analysis unit 101-46 proceeds to the process in step S6076.

<Step S6072>

In the present embodiment, enhancement scale adjustment is performed by setting a variety of enhancement scales in accordance with the depth range.

Setting a large enhancement scale for a depth range in which the distance from the inner limiting membrane is smaller than a predetermined value, such as the distance to the retinal superficial layer, allows appropriate enhancement of a blood vessel having a large diameter, such as retinal artery and vein, (without disappearance of blood vessel or separation of blood vessel into multiple regions), whereby the perfusion area can be accurately identified. On the other hand, in a region where only capillaries are present, such as the retinal deep layer, small-scale enhancement can be performed to enhance the edge of a thinner blood vessel for more accurate identification of the perfusion area when binarized (can prevent phenomenon of overdetection of perfusion area).

The present invention does not limit the enhancement scale adjustment for blood vessels having different diameters to setting the enhancement scale in a motion contrast front image. For example, the enhancement scale may be adaptively set in a three-dimensional motion contrast image.

<Step S6073>

The enhancement unit 101-461 performs blood vessel enhancement filtering based on an eigenvalue of a Hessian matrix on the motion contrast images having undergone the pre-processing in step S606. The enhancement filter is collectively called a Hessian filter and may, for example, be a vesselness filter or a multi-scale line filter. In the present embodiment, the multi-scale line filter is used, and an arbitrary known blood vessel enhancement filter may instead be used.

A Hessian filter smoothens an image by using a size appropriate for the diameter of a blood vessel desired to be enhanced, calculates a Hessian matrix the elements of which have second derivatives of the luminance values at the pixels of the smoothened image, and enhances a local structure based on the magnitude of the eigenvalue of the matrix. A Hessian matrix is a square matrix expressed by Expression (3), and each element of the matrix is expressed by the second derivative of a luminance value Is of an image having a smoothened luminance value I, as indicated by Expression (4). In a case where "one of the eigenvalues ($\lambda 1$, $\lambda 2$) of the Hessian matrix is close to zero and the other has a large negative absolute value," the Hessian filter enhances the pixels as a linear structure. This corresponds to enhancement of a feature of a perfusion area in motion contrast images, that is, pixels that satisfy "the luminance changes by a small amount in the blood traveling direction, whereas the luminance value greatly decreases in the direction perpendicular to the blood traveling direction" as a linear structure.

Since motion contrast images contain blood vessels having a variety of diameters from capillaries to small artery and vein, a Hessian matrix is applied to an image smoothened with a Gaussian filter at a plurality of scales to generate a line enhancement image. The square of a smoothening parameter $\sigma$ of the Gaussian filter is multiplied as a correction coefficient as shown in Expression (5), and the result of the multiplication undergoes combination by using maximum value operation. The resultant combined image Ihessian is output from the Hessian filter.

The present invention is not limited to the application of a two-dimensional Hessian filter to motion contrast front images. For example, a three-dimensional Hessian filter may be applied to a three-dimensional motion contrast image to generate a three-dimensionally enhanced image.

A Hessian filter is advantageously insensitive to noise and improves continuity of a blood vessel. On the other hand, since the maximum diameter of each blood vessel contained in an image is unknown in advance in many cases, an enhanced perfusion area is disadvantageously likely to be thicker particularly in a case where the smoothening parameter is too large with respect to the maximum diameter of the blood vessel. In the present embodiment, the disadvantage is eliminated by performing the enhancement scale adjustment described in step S6072. The method for appropriately enhancing and binarizing motion contrast images irrespective of the diameter of a blood vessel is not limited to the method described in the present embodiment. For example, a region common to a binary Hessian enhancement image and a binary blood vessel enhancement image enhanced by edge selective sharping may be identified as the perfusion area.

$$H = \begin{bmatrix} \partial_{xx} \, I_s & \partial_{xy} \, I_s \\ \partial_{yx} \, I_s & \partial_{yy} \, I_s \end{bmatrix} \tag{3}$$

$$\partial_{xx} \, I_s = \frac{\partial^2}{\partial x^2} G(x, y; \sigma) * I(x, y) \tag{4}$$

$$I_{hessian}(x, y) = \max_i \{\sigma_i^2 I_{hessian}(x, y; \sigma_i)\} \tag{5}$$

<Step S6074>

The extraction unit 101-462 binarizes the blood vessel enhancement image enhanced by the Hessian filer (hereinafter referred to as Hessian enhancement image) and generated in step S6073. In the present embodiment, the binarization is performed by using the average of the Hessian enhancement image as a threshold. It is, however, noted that a predetermined lower value of the binarization threshold is set to prevent misdetection of a region other than a blood vessel as an artifact. FIG. 8B illustrates an example of motion contrast images of the lamina cribrosa portion, and FIG. 8C illustrates an example of the blood perfusion area located in the lamina cribrosa and binarized in the process in the present step.

The process in the present step is not limited to the thresholding, and the binarization may be performed by using an arbitrary known segmentation method. Further, the segmentation in the present step is not necessarily applied to an entire image. For example, the operator may instead use the input unit 103 to perform the segmentation only on an arbitrarily shaped region set in motion contrast images or an enhanced version of the motion contrast images. Still instead, the image processing unit 101-04 may automatically set the same segmentation target region set in motion contrast images in the present step as a segmentation target region in tomographic images in step S6077, which will be described later.

<Step S6075>

The extraction unit 101-462 performs morphology operation (opening process (expansion after contraction) and closing process (contraction after expansion)) as the process of shaping the perfusion area. The shaping process is not limited to the process described above. For example, in a case where a binary image of the perfusion area is labeled, small region removal based on the area of each label may be performed.

<Step S6076>

The analysis unit 101-46 evaluates whether or not the measurement content instructed by the operator's specification of the OCT map selection button 803 and the OCT sector map selection button 804 or the arbitrary shape ROI selection button 807 in FIG. 8A requires identification of the lamina cribrosa or the lamina pores. In a case where the result of the evaluation shows YES, the analysis unit 101-46 proceeds to the process in step S6077, whereas in a case where the result of the evaluation shows No, the analysis unit 101-46 proceeds to the process in step S608.

It is assumed that "None" has been selected in the initial states of the two buttons.

<Step S6077>

In a case where the operator has selected the lamina cribrosa thickness as the content of the measurement performed on the tomographic images, the extraction unit 101-462 identifies a high-luminance region within the depth range surrounded by the front surface B6 and the rear surface B7 of the lamina cribrosa portion and acquired from the superimposed tomographic image generated in step S303 as a lamina cribrosa region L (white region in FIG. 8E).

Similarly, in a case where the operator has selected the lamina pore area as the content of the measurement, the image feature acquisition unit 101-44 identifies a low-luminance bulk-state region acquired from the superimposed tomographic front image (FIG. 8D) generated in step S303 as a lamina pore region LP (black region in FIG. 8E). In a case where the low-luminance region is located in the same position where the perfusion area identified in step S6074 is located, the extraction unit 101-462 determines that the low-luminance region is a blood vessel shadow region V (gray region in FIG. 8E) and excludes the low-luminance region from the lamina pore region LP.

In the present embodiment, the segmentation is directly performed on tomographic images, but not necessarily, and the segmentation may be performed after arbitrary known enhancement is applied to the tomographic images.

The segmentation in the present step is not necessarily applied to an entire image. For example, the operator may instead use the input unit 103 to perform the segmentation only on an arbitrarily shaped region set in tomographic images or an enhanced version of the tomographic images.

<Step S6078>

The image processing unit 101-04 applies the morphology operation (opening process and closing process) to a binary image of the lamina cribrosa region L or the lamina pore region LP identified in step S6077 to shape the identified lamina cribrosa region or lamina pore region. The shaping process is not limited to the process described above. For example, in a case where the binary image is labeled, small region removal based on the area of each label may be performed.

Further, the process carried out in step S608 will be described in detail with reference to the flowchart illustrated in FIG. 7B.

<Step S6081>

The analysis unit 101-46 sets a region of interest (measurement target image and measurement region) based on the content instructed by the operator's specification of the OCT map selection button 803, the OCT sector map selection button 804, the OCTA map selection button 805, the OCTA sector map selection button 806, or the arbitrary shape ROI selection button 807 in FIG. 8A in step S606.

In the present embodiment, since "None" has been selected as the OCT map, the lamina cribrosa thickness ("LCT") has been selected as the OCT sector map, "None" has been selected as the OCTA map, and "VLD" has been selected as the OCTA sector map, as illustrated in FIG. 9A, sector regions illustrated in FIG. 8F are set as the sector regions set in the lamina cribrosa portion as the measurement region of interest in the tomographic images. The region of interest is not limited to the regions described above, and the tomographic images may each be divided into upper and lower two regions, as illustrated in FIG. 8G, or smaller sector regions may be set in the tomographic images, as illustrated in FIG. 8H. Still instead, a region of interest having an arbitrary shape may be set in the tomographic images.

<Step S6082>

The image processing unit 101-04 evaluates whether or not measurement of the lamina cribrosa or the lamina pores is performed based on the measurement content instructed by the operator's specification of the OCT map selection button 803 and the OCT sector map selection button 804 or the arbitrary shape ROI selection button 807 in FIG. 8A. In a case where the result of the evaluation shows YES, the image processing unit 101-04 proceeds to the process in step S6083, whereas in a case where the result of the evaluation shows No, the image processing unit 101-04 proceeds to the process in step S6084.

<Step S6083>

The measurement unit 101-463 calculates a measurement value associated with the lamina cribrosa shape in the region of interest set in step S6082. In the present embodiment, since the lamina cribrosa thickness has been set as the lamina cribrosa shape, the thickness of the lamina cribrosa in the depth direction is measured in the region of interest set in step S6082 (average of lamina cribrosa thicknesses in sector regions illustrated in FIG. 8F) based on the lamina cribrosa region identified in step S6077.

<Step S6084>

The analysis unit 101-46 evaluates whether or not the blood vessel distribution is measured based on the measurement content instructed by the operator's specification of the OCTA map selection button 805 and the OCTA sector map selection button 806 or the arbitrary shape ROI selection button 807 in FIG. 8A. In a case where the result of the evaluation shows YES, the analysis unit 101-46 proceeds to the process in step S6085, whereas in a case where the result of the evaluation shows No, the analysis unit 101-46 proceeds to the process in step S609.

<Step S6085>

The analysis unit 101-46 evaluates whether or not the content of the measurement to be performed on the perfusion area is VLD. In a case where the result of the evaluation shows YES, the analysis unit 101-46 proceeds to the process in step S6086, whereas in a case where the result of the evaluation shows No, the analysis unit 101-46 proceeds to the process in step S6087.

<Step S6086>

The measurement unit 101-463 thins a binary image of the perfusion area generated in step S6074 to generate a binary image having a one-pixel linewidth corresponding to the center line of each blood vessel (hereinafter referred to as skeleton image). An arbitrary thinning method or a skeleton process may be used. In the present embodiment, a Hilditch thinning method is used as the thinning method.

<Step S6087>

The measurement unit 101-463 performs the measurement based on the skeleton image generated in step S6086. In the present embodiment, in the position of each of the pixels of the skeleton image, the sum of the lengths of non-zero pixels (white pixels) per unit area [$mm^{-1}$] in a small region around the pixel may be calculated as the blood vessel density (VLD) at the pixel. Further, an image having the blood vessel density (VLD) value calculated at each of the pixels is generated (VLD map, FIG. 8I).

In a case where a sector region is specified as the region of interest, the sum of the lengths of non-zero pixels (white pixels) per unit area [$mm^{-1}$] in each sector region in the skeleton image may be calculated as the blood vessel density (VLD) in the sector.

In a case where a VAD map is specified as the measurement to be performed on motion contrast images, the following procedure may be taken. That is, in the position of each of the pixels of the binary image of the perfusion area acquired in step S6074, the proportion of the non-zero pixels (white pixels) that occupy the small region around the pixel is calculated as the blood vessel density (VAD) at the pixel; and an image having the calculated VAD value at each pixel is generated (VAD map, FIG. 8J). Similarly, a VAD sector map can be generated by calculating the proportion of the non-zero pixels (white pixels) in each sector region of the binary image of the perfusion area as the blood vessel density (VAD) in the sector.

According to the configuration described above, the image processing apparatus 101 generates a superimposed image formed of OCT tomographic images containing the lamina cribrosa portion acquired in EDI imaging, identifies the lamina cribrosa and the lamina pore region, and calculates measurement value associated with the lamina cribrosa thickness and the lamina pores. The image processing apparatus 101 further identifies the perfusion area based on a motion contrast front image of the lamina cribrosa portion generated from an OCTA superimposed image, calculates the blood vessel density, and displays the two images and measurement values acquired from the two images in the side-by-side or superimposition form. The relationship between the shape of the lamina cribrosa portion and the distribution of blood-perfusion blood vessels in the lamina cribrosa portion is readily grasped.

Third Embodiment

An image processing apparatus according to the present embodiment uses motion contrast images generated from OCT tomographic images and an OCTA superimposed image containing the lamina cribrosa portion of the same eye to be inspected acquired in substantially the same imaging conditions at times and dates different from one another to measure the shape of the lamina cribrosa and the blood vessel density. A description will be made of a case where measurement data produced from the acquired images and the measurement are progressively displayed in the side-by-side or superimposition form. The image superimposition and other operations are not essential in the present invention.

Figure 10:
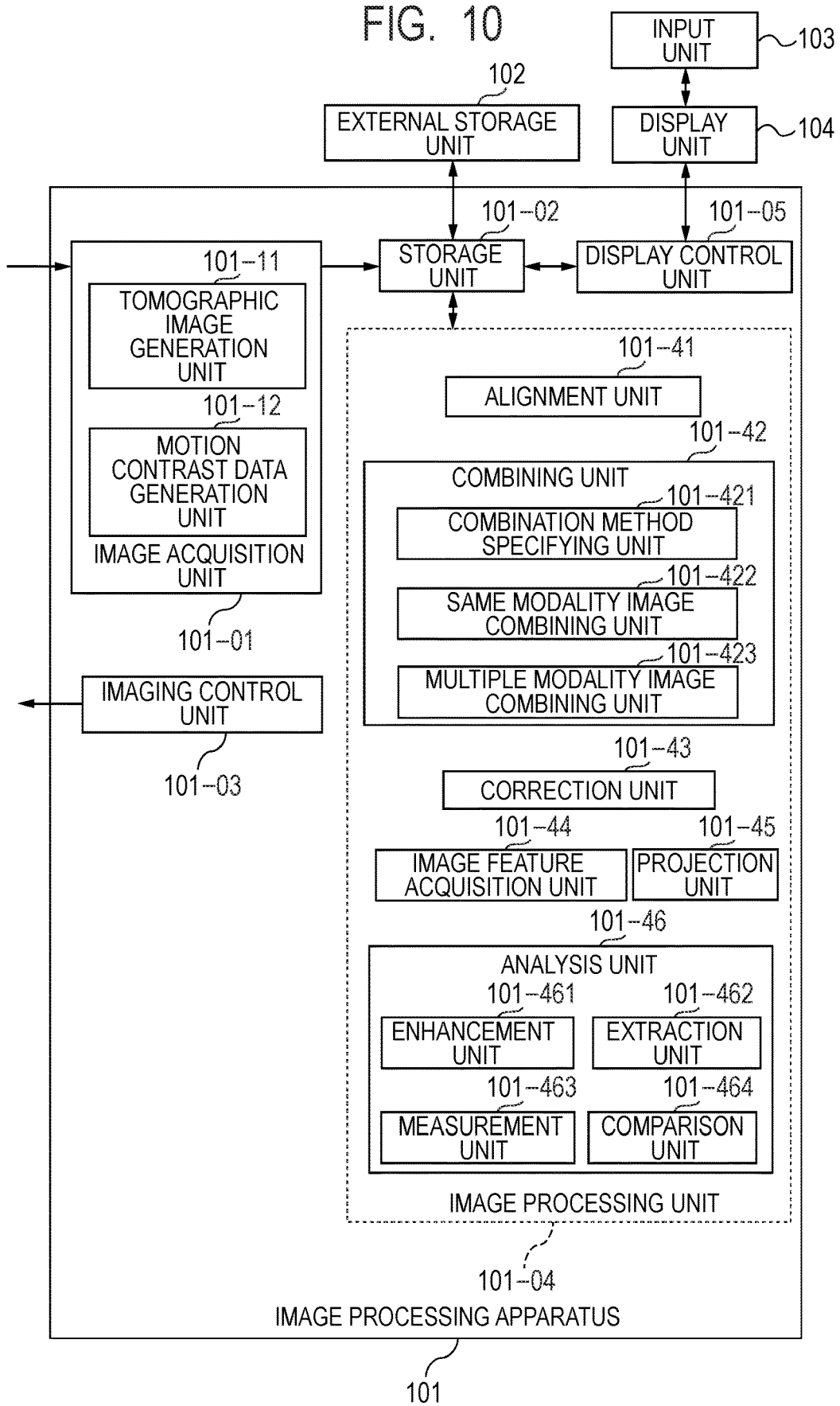
FIG. 10 illustrates the configuration of an image processing apparatus according to a third embodiment.

FIG. 10 illustrates the configuration of the image processing system 10 including the image processing apparatus 101 according to the present embodiment. The third embodiment differs from the second embodiment in that the analysis unit 101-46 includes a comparison unit 101-464.

Figure 11:
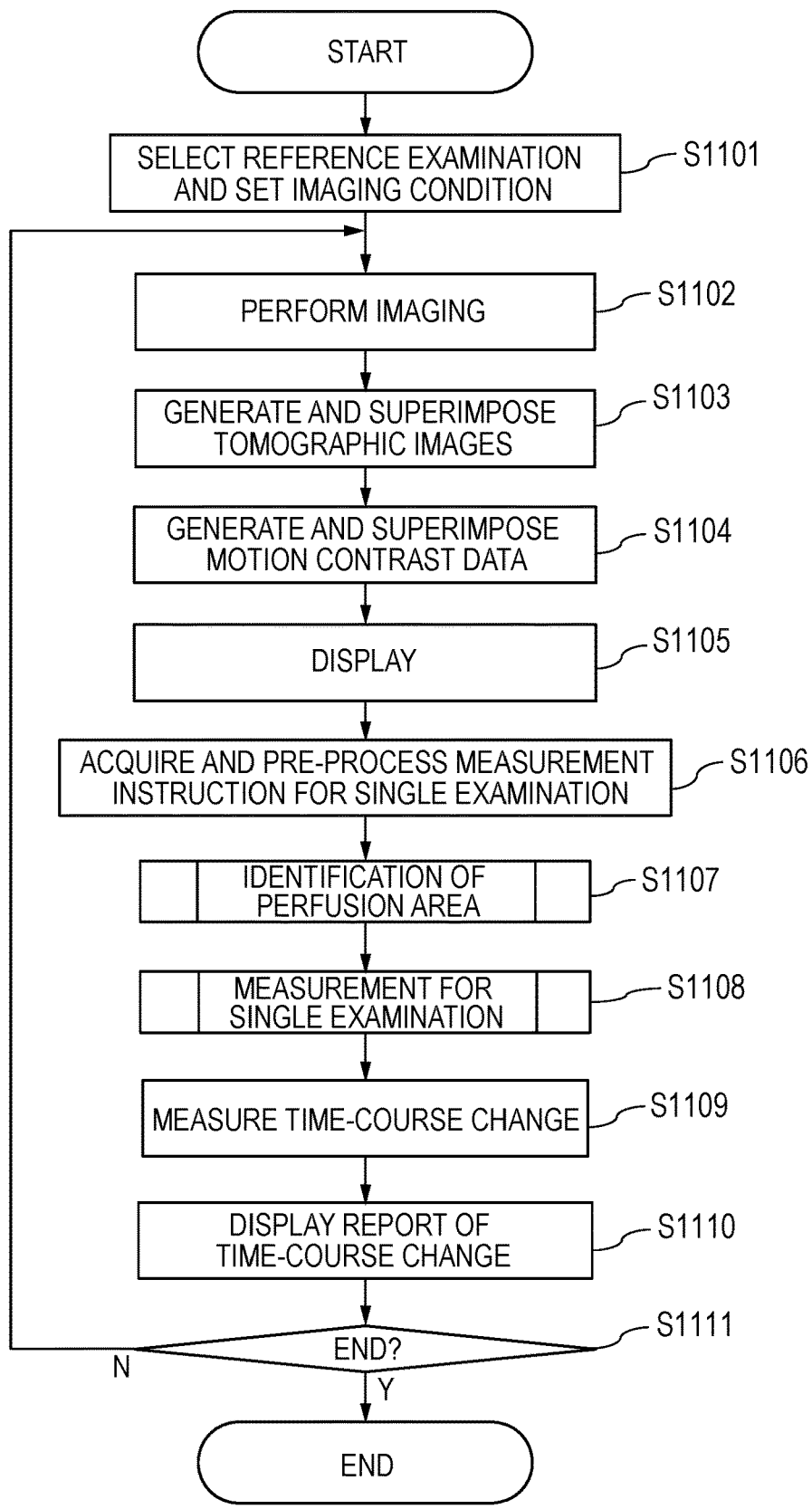
FIG. 11 is a flowchart of processes executable by an image processing system according to the third embodiment.

FIG. 11 illustrates the image processing flow in the present embodiment. In the image processing flow in the present embodiment, the steps in FIG. 11 excluding steps S1101, S1109, and S1110 are the same as those in the second embodiment and will not therefore be described.

<Step S1101>

The operator selects a baseline to be performed on the eye to be inspected on which past examination data has been saved. The image processing apparatus 101 sets imaging conditions under which the OCTA imaging is performed in such a way that the set imaging conditions are the same as the imaging conditions under which the selected baseline is performed.

In the present embodiment, the operator operates the input unit 103 to select a subject from a patient list in a patient screen (not illustrated). The operator further selects a baseline in follow-up examination from an examination list for the subject to determine the baseline. To select an examination set or a scan mode, the operator activates the imaging screen in the state in which the baseline has been selected to allow the image processing apparatus 101 to select a follow-up examination set and set the scan mode to be the same scan mode in the baseline (OCTA mode). The examination set refers to an imaging procedure set on an examination purpose basis (including scan mode) and a default method for displaying OCT images and OCTA images.

The image processing apparatus sets OCTA image capturing conditions instructed to the tomographic image capturing apparatus 100. The OCTA image capturing conditions are formed of the following setting items 1) to 7), and OCTA imaging is repeatedly performed by a predetermined number (under the same imaging conditions) in step S1102 with an interval interposed between the imaging actions as appropriate with the setting items set to have the same values as those of the baseline.

In the present embodiment, 7) OCTA imaging in which the B-scans per cluster is 4 is repeated 3 times.

1) Scan pattern
2) Scan size

3) Scanning direction
4) Distance between B-scans
5) Fixation position
6) C-gate orientation
7) B-scans per cluster <Step S1109>

Figure 12A:
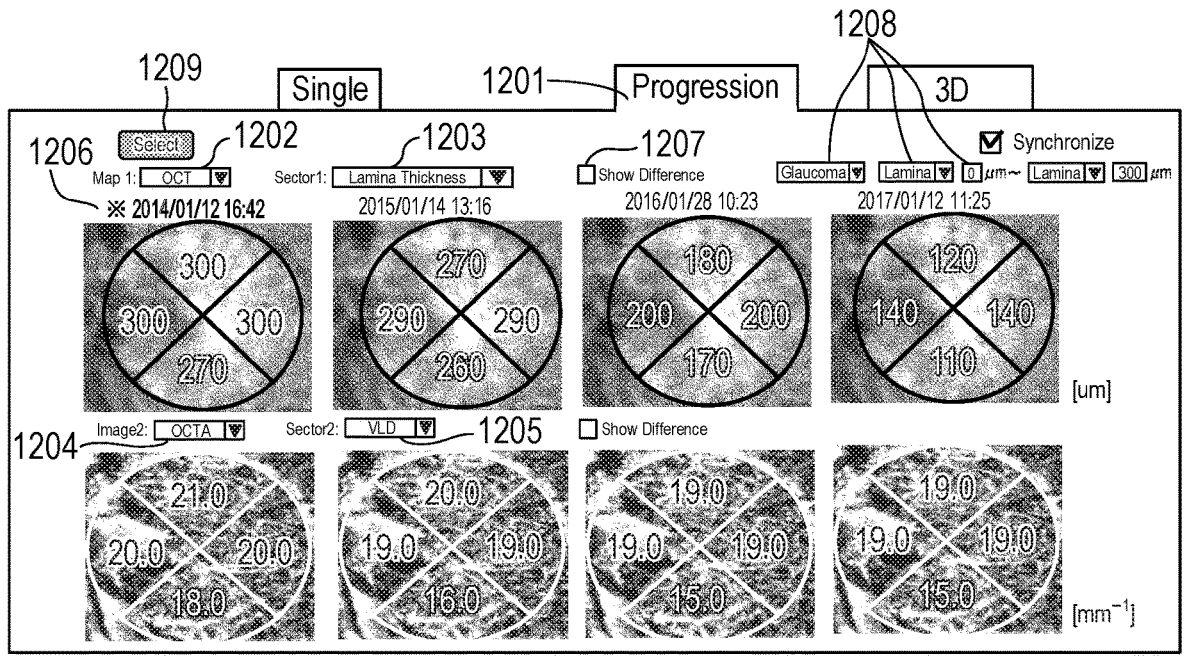
FIG. 12A and FIG. 12B describe a progressive measurement report screen displayed on a display unit in the third embodiment.
Figure 12B:
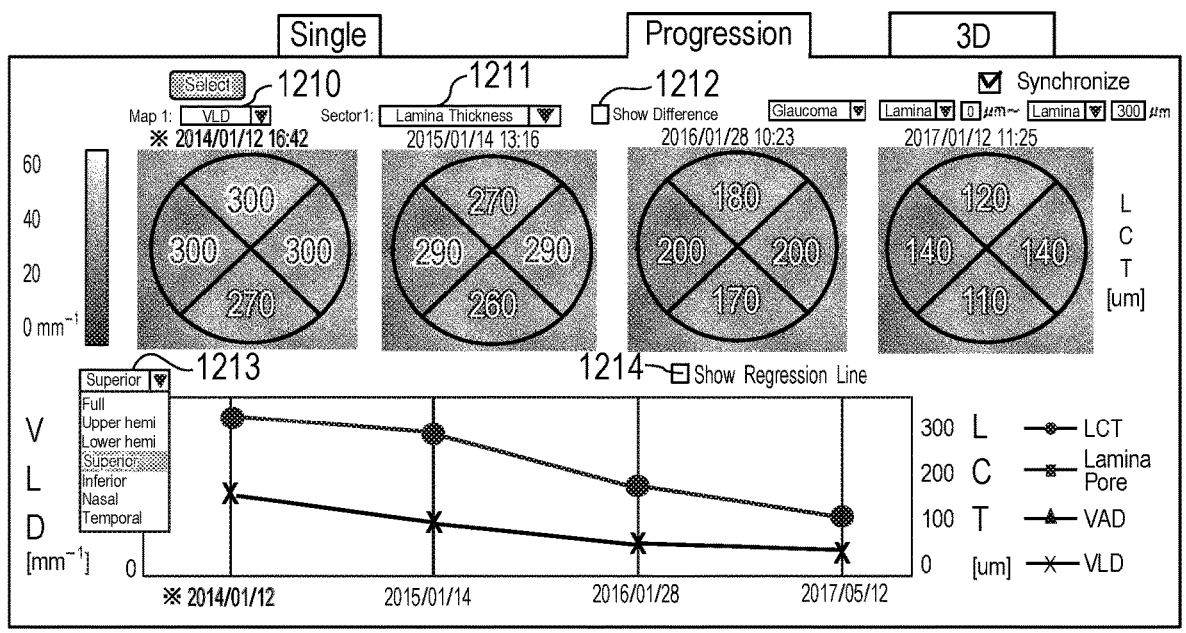

The comparison unit 101-464 performs progression measurement. FIGS. 12A and 12B illustrate examples of a progression measurement report. The operator specifies a progression mode tab 1201 to cause the screen of the report to be displayed and the progression measurement to start. In the present embodiment, as a progression measurement target image, images in four examinations are automatically selected in descending order of examination date, but not necessarily. For example, an image captured on the earliest examination date and an image in the latest examination and images captured at dates between the two examination dates and at roughly equal examination intervals may be selected. It is assumed to preferentially select as the measurement targets images a combined motion contrast image produced by performing the OCTA superimposition in such a way that the measurement target images are motion contrast images so captured that a large number tomographic images have been acquired in substantially the same position (at least 4) or motion contrast images equivalent thereto. The measurement target images are not limited thereto, and the operator may select a selection button 1209 in FIGS. 12A and 12B to cause a selection screen to be displayed and select images from an image list displayed in the selection screen.

The comparison unit 101-464 then acquires past examination images corresponding to the measurement content of the single examination performed in step S1108 and data on measurement values associated with the images from the external storage unit 102. Further, the alignment unit 101-41 aligns the single examination images measured in step S1108 with the past examination images, and the comparison unit 101-464 creates measurement values associated with a region common to the images and a progression graph associated with the measurement values.

In a case where it is believed that the image selection has been so performed that accurate measurement cannot be expected, that is, at least one of the following cases applies,
i) in a case where the selected measurement target images contain motion contrast images so captured that the number of tomographic images acquired in substantially the same position is smaller than a predetermined value, a combined motion contrast image corresponding to such a motion contrast image so captured that the number of the tomographic images acquired in substantially the same position is smaller than the predetermined value, or motion contrast images having a quality index smaller than a predetermined value; and
ii) in a case where the number of acquired tomographic images or the quality index in substantially the same position greatly varies among the selected measurement target images,
a warning may be so displayed as to prompt the operator to perform the selection again.

<Step S1110>

The display control unit 101-05 displays a report on the progression measurement performed in step S1109 on the display unit 104.

In the present embodiment, "OCT" is selected from a map selection list box 1202, and "Lamina Thickness" is selected from a sector selection list box 1203, which are located in an upper portion of the progression measurement report illustrated in FIG. 12A, and "OCTA" is selected from a map selection list box 1204, and "VLD" is selected from a sector selection list box 1205, which are located in a lower portion of the progression measurement report. As a result, the tomographic images of the lamina cribrosa portion and a lamina cribrosa thickness sector map are superimposed on each other in the upper portion, and the motion contrast images and a VLD sector map are superimposed on each other in the lower portion with the superimposed images progressively displayed. The display described above allows observation of the tomographic images and the motion contrast images in detail and progressive grasp of the progress of the state of the disease with the images related to the lamina cribrosa shape and the distribution of blood-perfusion blood vessels in the lamina cribrosa portion. In the example illustrated in FIG. 12A, the operator can grasp the way in which the blood vessel density decreases in the inferior portion of the lamina cribrosa portion and then in the superior portion thereof, the way in which the inferior and superior portions of the lamina cribrosa portion thin accordingly, and the way in which the overall lamina cribrosa thins as the time elapses.

In association with each measurement target image, the following pieces of information may be displayed on the display unit 104: selection of the right or left eye; the imaging time and date; the viewing angle and the number of pixels; the number of tomographic images in substantially the same position; information on conditions under which the OCTA superimposition has been performed; and/or an evaluation value (quality index) of OCT tomographic images or motion contrast images. Marks 1206 displayed in the upper portion of FIG. 12A represents the baseline.

In FIG. 12A, when the operator specifies a Show Difference check box 1207, an image illustrating the difference in the measurement value distribution between the reference image and each of the measurement target images (difference map illustrating difference in lamina cribrosa shape and difference map for blood-perfusion blood vessels in lamina cribrosa portion) can be progressively displayed in each of the upper and lower portions. That is, in FIG. 12A, a measurement value map in the reference image is displayed in the leftmost portion of each of the upper and lower portions, and the difference maps (illustrating difference from measurement value distribution in reference image) are displayed at three dates different from the date at which reference image has been captured. How much change in the lamina cribrosa shape and the distribution of the blood-perfusion blood vessels in the lamina cribrosa portion have occurred from the point of time of the baseline can be grasped in the form of a list.

In the present embodiment, tomographic images, measurement values associated therewith, motion contrast images, and measurement values associated therewith are progressively displayed side by side, but not necessarily in the present invention. For example, as illustrated in FIG. 12B, the measurement value map associated with the lamina cribrosa shape (lamina cribrosa thickness sector map, for example) and the distribution of blood-perfusion capillaries in the lamina cribrosa portion (VLD map for lamina cribrosa portion, for example) may be progressively displayed in the superimposition form. In this case, a portion where the lamina cribrosa shape has changed and a portion where the distribution of blood-perfusion blood vessels in the lamina cribrosa portion is abnormal can be accurately related to each other, and progressive changes in the two portions can be grasped in the form of a list.

Instead, when the operator specifies a Show Difference check box 1212 in FIG. 12B, an image illustrating the difference in the measurement value distribution between the reference image and each of the measurement target images (difference sector map illustrating difference in lamina cribrosa thickness and difference VLD map for blood-perfusion blood vessels in lamina cribrosa portion) can be progressively displayed in the superimposition form.

The progression of the measurement values associated with the lamina cribrosa shape and the distribution of blood-perfusion blood vessels in the lamina cribrosa portion are not necessarily displayed in the form of an image (map) and numerals. For example, the progression may be displayed in the form of a progression graph (trend graph), as illustrated n in FIG. 12B. In the example illustrated in FIG. 12B, the operator selects "Superior" from a list box 1213 to cause a trend graph illustrating the combination of the lamina cribrosa thickness and VLD in the superior region of the lamina cribrosa portion to be displayed. In addition to the above, measurement value graphs associated with the lamina cribrosa shape and the blood vessel distribution in the full lamina cribrosa portion, the upper-hemi-portion thereof, the lower-hemi-portion thereof, the inferior portion thereof, the nasal side thereof, the temporal portion, or any other region of interest having an arbitrary shape may be switched from one to another or may be displayed in the form of a list. To display a plurality of graphs in the form of a list, the graphs may be so displayed as to be distinguished from one another (in different colors, line types, thicknesses, or symbols, for example). Further, the operator may specify a Show Regression Line check box 1214 to display a regression line and a corresponding numeral expression on the display unit 104.

The present invention is no limited to the progressive display of images in the lamina cribrosa region in the portion inside the optic papilla boundary D or measurement values acquired in the lamina cribrosa region. For example, the present invention encompasses progressive display of regions and measurement values identified or acquired in the lamina cribrosa region (region surrounded by front surface B6 and rear surface B7 of lamina cribrosa) in the portion inside the optic papilla boundary D and regions and measurement values identified or acquired within the depth range defined by the retinal superficial layer (nerve fiber layer, for example) in the portion outside the optic papilla boundary D. A specific example may be a case where the following two measurement value maps are progressively displayed side by side: a measurement value map that displays "the lamina cribrosa thickness in the portion inside the optic papilla boundary D, the nerve fiber layer thickness (or ganglion cell layer thickness, ganglion cell complex (GCC) thickness) in the portion outside the optic papilla boundary D" is displayed in an upper portion of the display unit 104; and a measurement value map that displays "the blood vessel density (VLD or VAD) in the lamina cribrosa portion in the portion inside the optic papilla boundary D and the blood vessel density (VLD or VAD) in the RPC in the portion outside the optic papilla boundary D" is displayed in a lower portion of the display unit 104. The progressive side-by-side display described above (or progressive superimposition display) allows not only grasp of progressive changes in the relation between the distribution of blood-perfusion blood vessels in the lamina cribrosa portion and a site of the lamina cribrosa where the shape thereof has changed but grasp of progressive changes in the relation between a site where the lamina cribrosa shape has changed and a region where nerve fiber layer has thinned. That is, a symptom that causes thinning of the nerve fiber layer and the ganglion cell layer (retraction of blood-perfusion blood vessels in the lamina cribrosa portion and resultant change in shape of lamina cribrosa portion) and progressive changes in ganglion cell death (thinning of nerve fiber layer and ganglion cell layer) resulting from the symptom can be listed and is therefore useful as display setting for glaucoma diagnosis. To progressively display measurement value distributions acquired in the lamina cribrosa region in the portion inside the optic papilla boundary D and within the depth range of the retinal superficial layer in the portion outside the optic papilla boundary D on the display unit 104, only the measurement value map that displays "the lamina cribrosa thickness in the portion inside the optic papilla boundary D, the nerve fiber layer thickness (or ganglion cell layer thickness, ganglion cell complex (GCC) thickness) in the portion outside the optic papilla boundary D" may be displayed on the display unit 104, or only the measurement value map that displays "the blood vessel density in the lamina cribrosa portion in the portion inside the optic papilla boundary D, the blood vessel density in the RPC in the portion outside the optic papilla boundary D" may be displayed on the display unit 104. The projection depth range outside the papilla and blood vessels identified and measured in the portion outside the papilla are not limited to the nerve fiber layer and RPC, respectively. For example, capillaries in the retinal superficial layer may be identified and measured over the projection depth range defined by the retinal superficial layer, or capillaries in the retinal deep layer within the projection depth range defined by the retinal deep layer may be identified and measured and the distribution of the capillaries may be progressively displayed. Further, the progressively displayed result of the identification and measurement of blood vessels in the portion inside and outside the papilla is not necessarily displayed in the form of the blood vessel density. For example, the result may be displayed in the form of the position of the perfusion area, the position of the non-perfusion area, the shape of the non-perfusion area, the area of the perfusion area, the area of the non-perfusion area, the length of each blood vessel, and/or the curvature of each blood vessel.

The projection depth range used in the progressive side-by-side/superimposition display can be changed by using a user interface labeled with 1208 in FIG. 12A. Further, the projection method (MIP/AIP) and the projection artifact removal may also be changed, for example, by a method based on selection from a context menu.

In a case where the image processing apparatus 101 accepts an instruction associated with identification or measurement of the perfusion area in motion contrast images so captured that the number of tomographic images acquired in substantially the same scan position is smaller than a predetermined value or a combined motion contrast image corresponding to a value smaller than the predetermined value, a warning may be displayed on the display unit 104.

According to the configuration described above, the image processing apparatus 101 uses motion contrast images generated from OCT tomographic images and an OCTA superimposed image containing the lamina cribrosa portion of the same eye to be inspected acquired in substantially the same imaging conditions at times and dates different from one another to measure the lamina cribrosa shape and the blood vessel density. The image processing apparatus 101 progressively displays the acquired images and measurement data produced by the measurement in the side-by-side or superimposition form.

The relationship between progressive changes the shape of the lamina cribrosa portion and progressive changes in the distribution of blood-perfusion blood vessels in the lamina cribrosa portion is readily grasped.

According to the first to third embodiments described above, the relationship between the shape of a predetermined site, such as the lamina cribrosa portion, and the distribution of blood-perfusion blood vessels in the predetermined site can be readily grasped.

Fourth Embodiment

When a captured image of, e.g., a glaucomatous eye is examined, the lamina cribrosa located in deep layers can be observed within the optic disc. On the other hand, on the periphery of the optic disc, capillary vessels can be observed in shallower layers. In a conventional technique for this examination, a single depth range is set for the entire area of a two-dimensional front image to be generated. Therefore, if the deeper layers and the shallower layers are desired to be observed at a time in the two-dimensional front image, a single depth range extending from the deeper layers to the shallower layers needs to be set as the depth range for generating the two-dimensional front image.

With such depth-range setting, in some regions in a direction (for example, an in-plane direction on the XY plane) intersecting the depth direction of the eye to be inspected, the single depth range may include not only the site of interest but also sites of no interest. Consequently, identifying the site of interest in the generated two-dimensional front image may be difficult.

Fourth to eighth embodiments have an object that is to facilitate identification of the site of interest in a two-dimensional front image.

The fourth embodiment of the present invention will be described below with reference to the drawings. An image processing apparatus according to this embodiment allows setting (specifying) different depth ranges for multiple regions in a direction (for example, an in-plane direction on the XY plane) intersecting the depth direction of an eye to be inspected (for example, a region within the optic disc and a region on the periphery of the optic disc). An image processing apparatus according to this embodiment can generate a two-dimensional front image of an eye to be inspected using three-dimensional data about the eye to be inspected and information (for example, Z-direction coordinate values) about the different set depth ranges (for example, for deeper layers and shallower layers). This can facilitate, for example, identification of the site of interest (for example, a vascular network) in the two-dimensional front image.

An image processing apparatus according to this embodiment can, in generating three-dimensional motion contrast data with reduced artifacts, align multiple motion contrast data sets while selecting a motion contrast data set as the alignment reference for calculating an additive average. This enables three-dimensional motion contrast data of high image quality to be acquired even if the motion contrast data contains artifacts due to causes such as involuntary eye movements. Here, high image quality means that an image has an improved S/N ratio or an increased amount of information required for diagnosis, as compared with an image obtained with one-time imaging. It is to be noted that processing of reducing artifacts according to this embodiment (for example, step S1505 in FIG. 15A) is not an essential part of the present invention.

In this embodiment, three-dimensional data refers to three-dimensional tomographic image data composed of luminance values and to three-dimensional motion contrast data composed of decorrelation values. A two-dimensional front image generated using three-dimensional tomographic image data is referred to as a two-dimensional luminance front image (or an en face image or a luminance en face image). A two-dimensional front image generated using three-dimensional motion contrast data is referred to as a motion contrast front image (or an OCTA image or a motion contrast en face image).

The depth range for generating a two-dimensional front image, and at least one region (partial region) where a depth range is to be set that is different from the depth range in other regions among multiple regions in the direction intersecting the depth direction of the eye to be inspected, may be set according to an operator's instruction (manual setting), or may be set based on the result of analysis such as three-dimensional data analysis (automatic setting), or may be automatically set and then changed (modified) according to the operator's instruction. Thus, a setting unit that sets the depth range or the at least one region may include at least one of these functions. If the setting unit includes two or more of the functions, the setting unit may be configured to allow selection of any of the functions. This facilitates the operator's choice of a function depending on the purpose.

The direction intersecting the depth direction may be a direction orthogonal to the depth direction, but the present invention is not limited to such a direction. For example, a setting unit that sets the depth direction may use information on the tilt of the retina relative to the depth direction in the tomographic image of the retina to set the direction for setting the depth range in the at least one region (partial region). For example, the direction of the normal to the tilted retina can be set, so that the depth ranges in the at least one region and other regions can be set along the set direction. This facilitates observation of a desired site by the operator such as a medical doctor. Here, the setting unit may set an in-plane direction of the tilted retina as the direction intersecting the depth direction.

An image processing system including an image processing apparatus according to this embodiment will be described in detail below.

Figure 13:
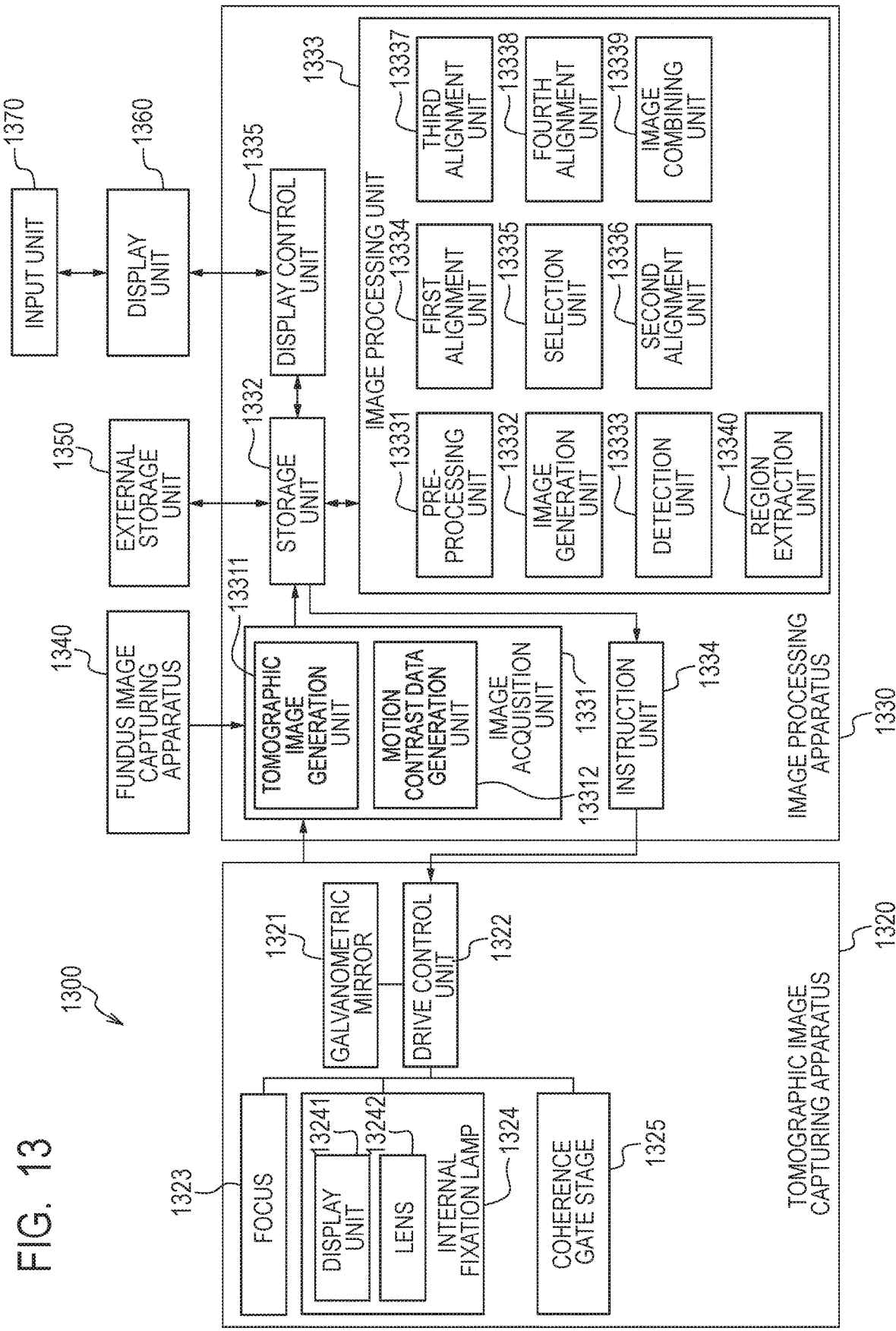
FIG. 13 illustrates the configuration of an image processing system according to a fourth embodiment.

FIG. 13 is a diagram illustrating a configuration of an image processing system 1300 including an image processing apparatus 1330 according to this embodiment. As shown in FIG. 13, the image processing system 1300 has the image processing apparatus 1330 connected, via interfaces, to a tomographic image capturing apparatus (also referred to as an OCT) 1320, a fundus image capturing apparatus 1340, an external storage unit 1350, a display unit 1360, and an input unit 1370.

The tomographic image capturing apparatus 1320 is an apparatus that captures a tomographic image of an eye. Exemplary apparatuses usable as the tomographic image capturing apparatus include an SD-OCT and an SS-OCT. The tomographic image capturing apparatus 1320 is a known apparatus and therefore will not be described in detail; here, tomographic image capturing performed in response to an instruction from the image processing apparatus 1330 will be described.

In FIG. 13, a galvanometric mirror 1321, which is used for scanning a fundus with measurement light, defines an OCT imaging range in the fundus. A drive control unit 1322 regulates the imaging range in the planar direction in the fundus and the number of scan lines (the scanning speed in the planar direction) by controlling the driving range and speed of the galvanometric mirror 1321. Although the galvanometric mirror is shown here as a single unit for simplicity, the galvanometric mirror actually includes two mirrors for X-scanning and Y-scanning, respectively, thereby being capable of scanning a desired range in the fundus with the measurement light.

A focus 1323 is used for focusing on retina layers of the fundus through the anterior eye portion of the eye to be inspected. A focus lens (not shown) focuses the measurement light on the retina layers of the fundus through the anterior eye portion of the eye to be inspected. The measurement light illuminating the fundus is reflected on and scattered back from each retina layer.

An internal fixation lamp 1324 includes a display unit 13241 and a lens 13242. As the display unit 13241, light-emitting diodes (LDs) arranged in a matrix are used. The positions where the light-emitting diodes emit light are varied under the control of the drive control unit 1322 as appropriate for the site to be imaged. The light from the display unit 13241 is guided through the lens 13242 to the eye to be inspected. The display unit 13241 emits light of 520 nm, with which a desired pattern is displayed under the control of the drive control unit 1322.

A coherence gate stage 1325 is controlled by the drive control unit 1322 to accommodate the axial-length difference of the eye to be inspected. A coherence gate refers to a position where the measurement light and the reference light of the OCT have an equal optical distance. Further, in imaging, the position of the coherence gate is controlled to image either the retina layer side or the side deeper than the retina layers. Now, the eye structure and images acquired by the image processing system will be described with reference to FIGS. 14A to 14C.

Figure 14A:
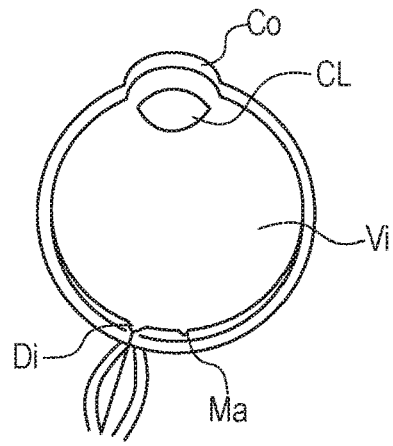
FIG. 14A, FIG. 14B, and FIG. 14C describe the structure of an eye portion, tomographic images, and a fundus image.

FIG. 14A is a schematic diagram of an eyeball. FIG. 14A shows the cornea Co, the crystalline lens CL, the vitreous body Vi, the macular area Ma (the center of the macula lutea represents the fovea centralis), and the optic disc Di. The tomographic image capturing apparatus 1320 according to this embodiment will be described mainly for the case of imaging the posterior pole portion of the retina, including the vitreous body, the macular area, and the optic disc. Although not described in the present invention, the tomographic image capturing apparatus 1320 can also image the anterior eye portion, including the cornea and the crystalline lens.

Figure 14B:
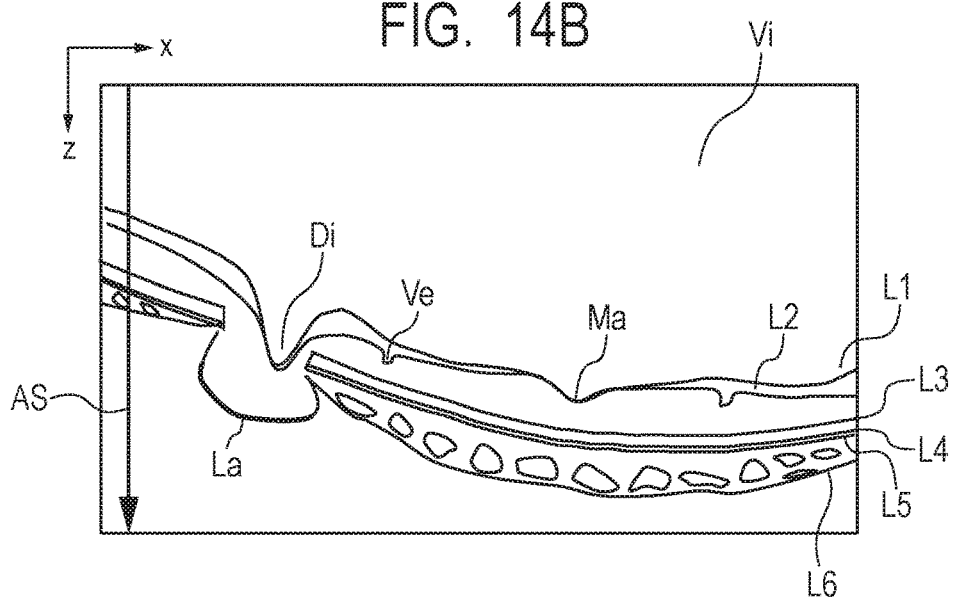

FIG. 14B illustrates an exemplary tomographic image acquired in imaging of the retina by the tomographic image capturing apparatus 1320. In FIG. 14B, AS represents an A scan, which is an image acquisition unit in an OCT tomographic image. Multiple A scans collectively forms a B scan, which is referred to as a tomographic image (or a tomographic picture). FIG. 14B shows a blood vessel Ve, the vitreous body Vi, the macular area Ma, the optic disc Di, and the posterior surface La of the lamina cribrosa. FIG. 14B also shows the boundary L1 between the inner limiting membrane (ILM) and the nerve fiber layer (NFL), the boundary L2 between the nerve fiber layer and the ganglion cell layer (GCL), the photoreceptor inner segment/outer segment junction (ISOS) L3, the retinal pigment epithelium layer (RPE) L4, the Bruch membrane (BM) L5, and the choroid L6. In the tomographic image, the abscissa (the main scanning direction of the OCT) is the x-axis, and the ordinate (the depth direction) is the z-axis.

Figure 14C:
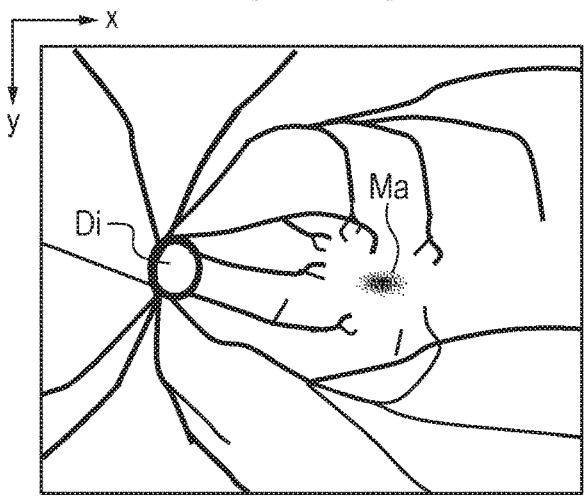

FIG. 14C illustrates an exemplary fundus image acquired by the fundus image capturing apparatus 1340. The fundus image capturing apparatus 1340 is an apparatus that captures a fundus image of an eye, examples of which including a fundus camera and an SLO (Scanning Laser Ophthalmoscope). FIG. 14C shows the macular area Ma and the optic disc Di, and bold curves represent blood vessels of the retina. In the fundus image, the abscissa (the main scanning direction of the OCT) is the x-axis, and the ordinate (the sub-scanning direction of the OCT) is the y-axis. The tomographic image capturing apparatus 1320 and the fundus image capturing apparatus 1340 may be integrated as a single apparatus or may be separate apparatuses.

The image processing apparatus 1330 includes an image acquisition unit 1331, a storage unit 1332, an image processing unit 1333, an instruction unit 1334, and a display control unit 1335. The image acquisition unit 1331 includes a tomographic image generation unit 13311 and a motion contrast data generation unit 13312. The image acquisition unit 1331 generates tomographic images and motion contrast data by acquiring signal data about tomographic images captured by the tomographic image capturing apparatus 1320 and performing signal processing on the acquired signal data. The image acquisition unit 1331 also acquires data about fundus images captured by the fundus image capturing apparatus 1340. The generated tomographic images and the fundus images are stored in the storage unit 1332. The image processing unit 1333 includes a preprocessing unit 13331, an image generation unit 13332, a detection unit 13333, a first alignment unit 13334, a selection unit 13335, a second alignment unit 13336, a third alignment unit 13337, a fourth alignment unit 13338, an image combining unit 13339, and a region extraction unit 13340.

The preprocessing unit 13331 performs processing of removing artifacts from the motion contrast data. The image generation unit 13332 uses the three-dimensional motion contrast data to generate two-dimensional motion contrast front images (also referred to as OCTA images), or uses the three-dimensional tomographic image data to generate two-dimensional luminance front images (also referred to as en face images). The detection unit 13333 detects the boundary lines between the layers from the retina. The first alignment unit 13334 aligns the two-dimensional front images. The selection unit 13335 selects reference data from the alignment result of the first alignment unit 13334. The second alignment unit 13336 aligns the retina in the horizontal direction (x-axis) using the OCTA images. The third alignment unit 13337 aligns the retina in the depth direction (z-axis). The fourth alignment unit 13338 sets alignment regions in characteristic portions in the tomographic images and aligns the retina in the depth direction (z-axis) in each region. The image combining unit 13339 calculates an additive average of the three-dimensional data aligned by the first to fourth alignment units. The region extraction unit 13340, which is an example of a region setting unit, extracts (sets, identifies or detects) at least one region where a depth range is to be set that is different from the depth range in other regions among multiple regions in the direction intersecting the depth direction of the eye to be inspected. Thus, in the at least one extracted region, a depth range different from the depth range in the other regions is set. Here, the set depth ranges are depth ranges for generating the OCTA images and/or the en face images.

The external storage unit 1350 holds information on the eye to be inspected (such as the patient's name, age and gender), captured image data, imaging parameters, image analysis parameters, and operator-set parameters, in association with each other.

The input unit 1370 is a mouse, a keyboard, or a touch-operation screen, for example. The operator provides instructions through the input unit 1370 to the image processing apparatus 1330, the tomographic image capturing apparatus 1320, and the fundus image capturing apparatus 1340.

Figure 15A:
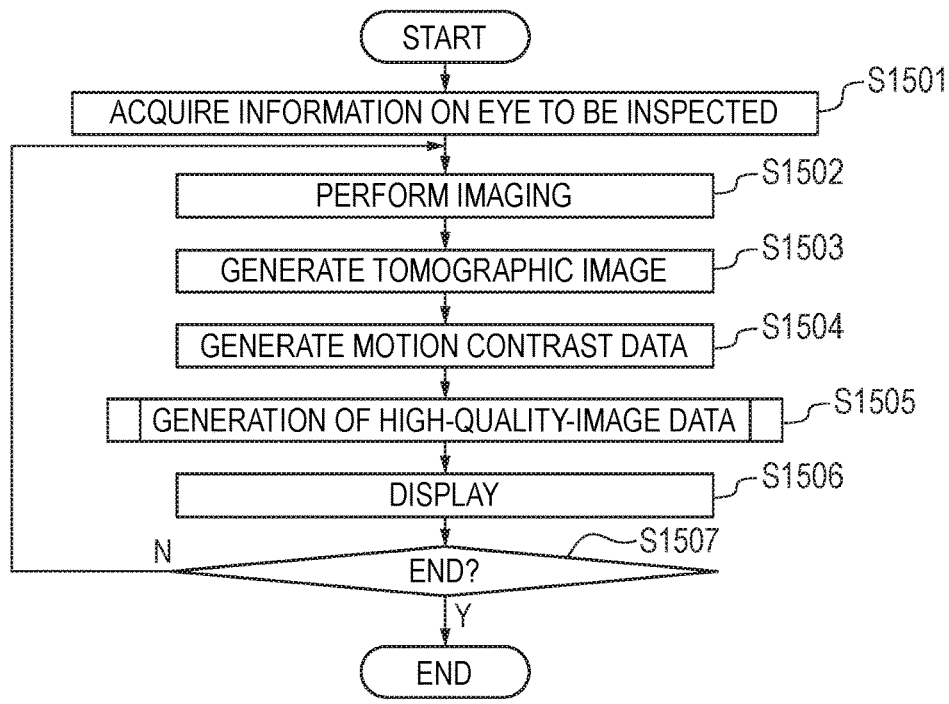
FIG. 15A is a flowchart illustrating the process flow in the image processing system according to the fourth embodiment.
Figure 15B:
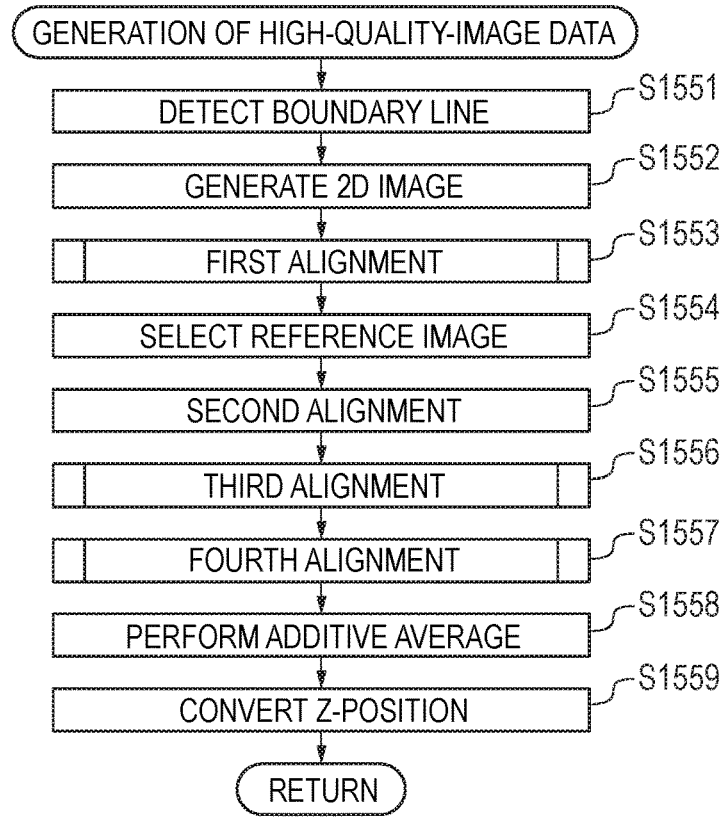
FIG. 15B is a flowchart illustrating the flow of high-quality data generation.
Figure 16:
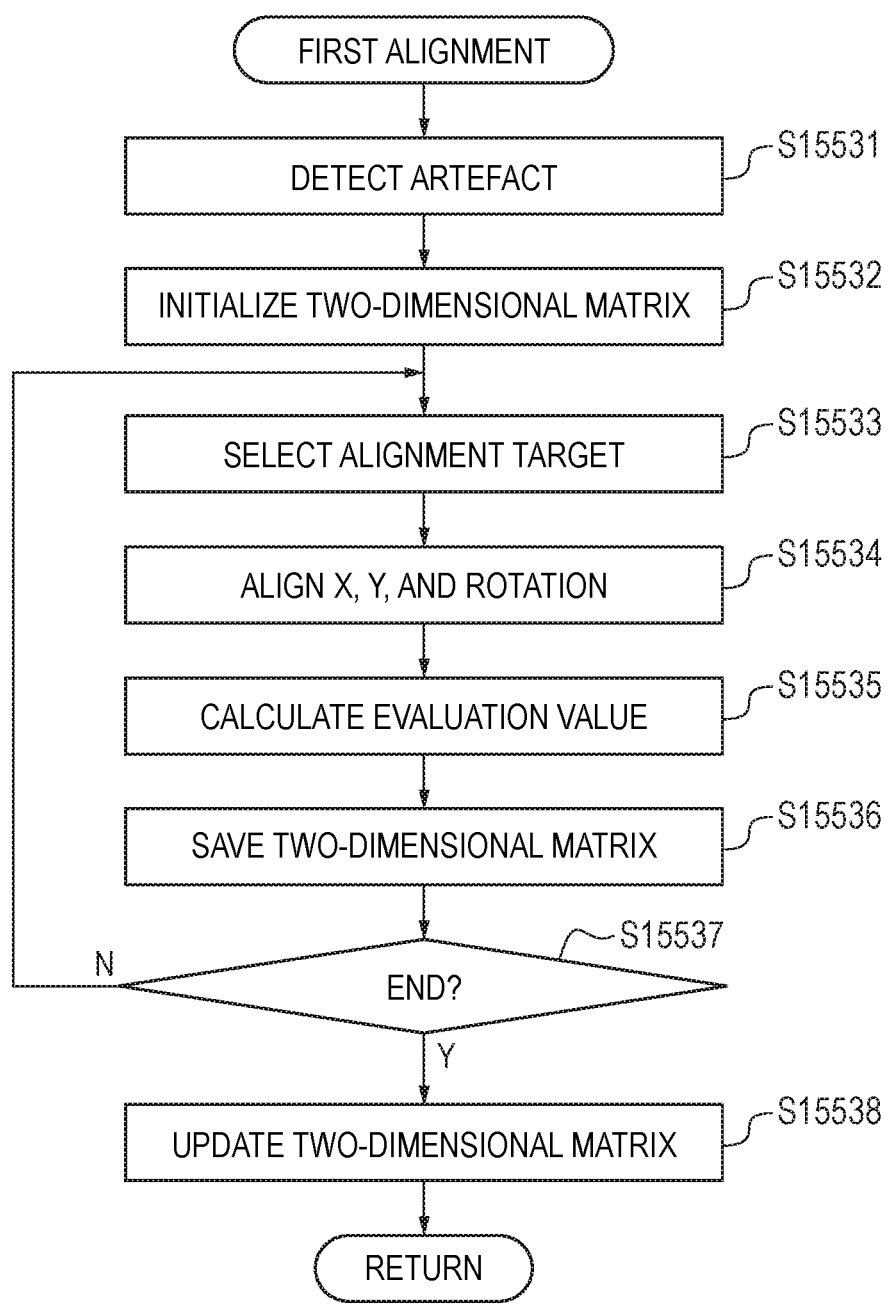
FIG. 16 is a flowchart illustrating the flow of first alignment.
Figure 17:
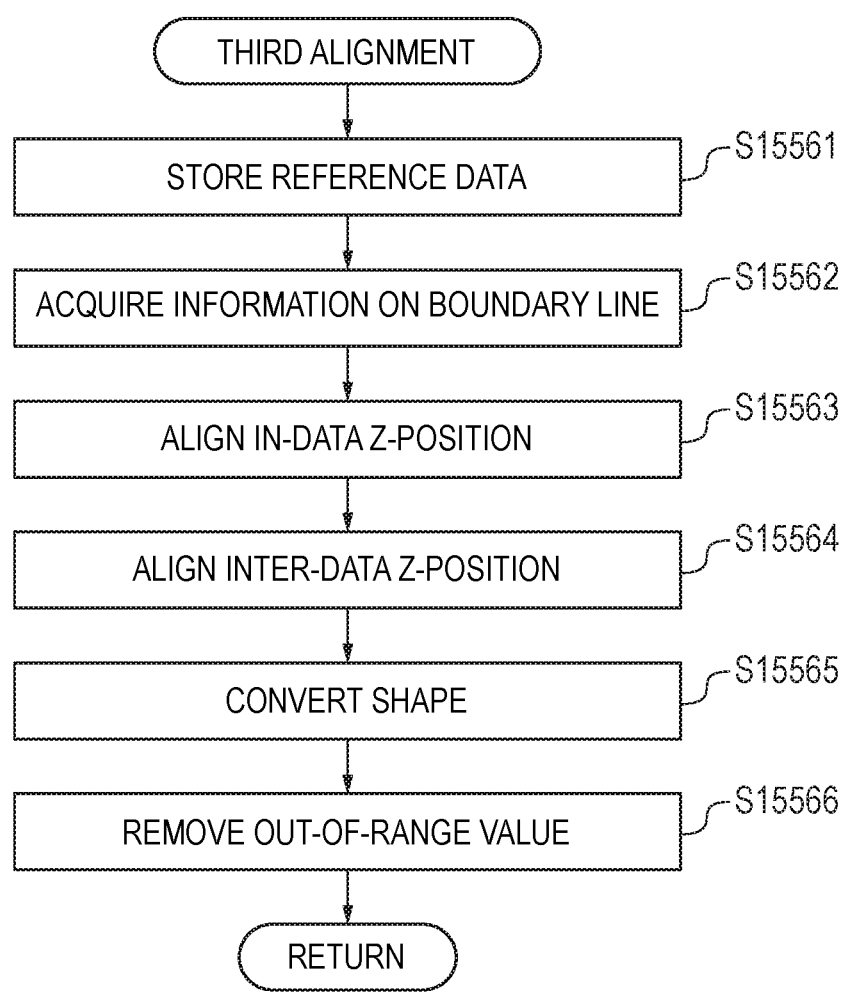
FIG. 17 is a flowchart illustrating the flow of third alignment.
Figure 18:
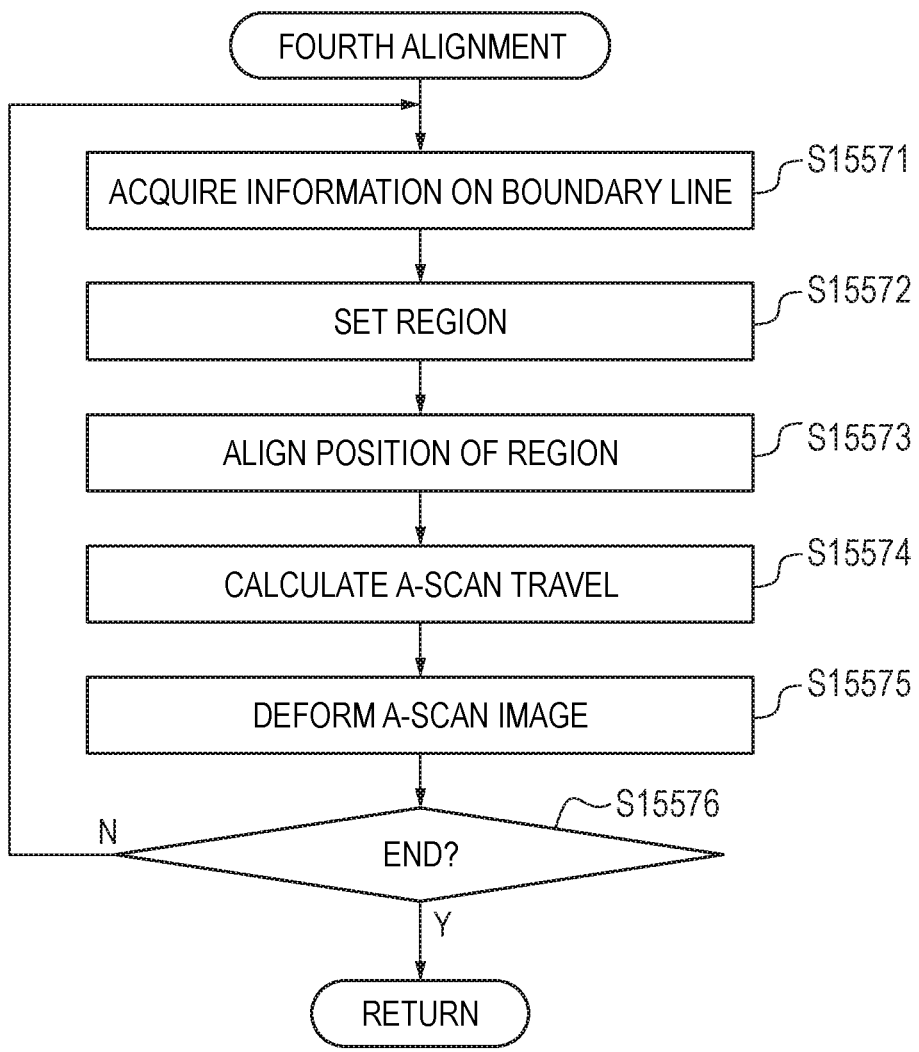
FIG. 18 is a flowchart illustrating the flow of fourth alignment.

Now, a procedure of the image processing apparatus 1330 in this embodiment will be illustrated with reference to FIGS. 15A and 15B. FIG. 15A is a flowchart illustrating the flow of a general operation process of the system in this embodiment. FIG. 15B is a flowchart illustrating the flow of a process of generating high-quality-image data in this embodiment.

<Step S1501>

At step S1501, as information for identifying an eye to be inspected, a subject's eye information acquisition unit (not shown) acquires a subject's identity number from an external entity. Based on the subject's identity number, information on the eye to be inspected held in the external storage unit 1350 is acquired and stored in the storage unit 1332.

<Step S1502>

At step S1502, the eye to be inspected is scanned to perform imaging. The eye to be inspected is scanned as follows. Upon the operator's selection of "start scan" (not shown), the tomographic image capturing apparatus 1320 controls the drive control unit 1322 to operate the galvanometric mirror 1321, which performs scanning for tomographic images. The galvanometric mirror 1321 includes an X scanner for the horizontal direction and a Y scanner for the vertical direction. Varying the orientations of these scanners enables scanning in the respective horizontal direction (X) and vertical direction (Y) in the coordinate system of the apparatus. Simultaneously varying the orientations of both scanners enables scanning in a composite direction of the horizontal and vertical directions, so that scanning is possible in any direction on the fundus plane.

Before imaging, various imaging parameters are adjusted. Specifically, at least the following parameters are set: the position of the internal fixation lamp, the scan range, the scan pattern, the position of the coherence gate, and the focus. The drive control unit 1322 controls the light-emitting diodes of the display unit 13241, so that the position of the internal fixation lamp 1324 is controlled for imaging of the central macular area and the optic disc. The scan pattern is set to a pattern for three-dimensional volume imaging, such as raster scan, radial scan or cross scan. After these imaging parameters are adjusted, the operator selects "start imaging" (not shown) to perform imaging.

In this embodiment, a scan pattern for three-dimensional volume based on raster scan is used, and a three-dimensional volume is imaged N times (N≥2) for generating high-quality-image data. The same imaging range is repeatedly imaged N times in the same scan pattern. For example, a 3 mm×3 mm range is repeatedly imaged at intervals of 300× 300 (main scanning×sub-scanning). For a three-dimensional volume, the location of a single line is repeatedly imaged M times (M≥2) for calculating the motion contrast. Thus, for M=2, actually 300×600 data is imaged to generate 300×300 three-dimensional motion contrast data.

Although not described in detail in this embodiment, in order to image the same locations for additive averaging, the tomographic image capturing apparatus 1320 tracks the eye to be inspected, thereby reducing the influence of fixational eye movements while scanning the eye to be inspected. Further, if a movement, such as a blink, that leads to an artifact in image generation is detected, rescanning is automatically performed at the location where the artifact occurs.

<Step S1503>

At step S1503, tomographic images are generated. The tomographic image generation unit 13311 generates the tomographic images by performing general reconfiguration processing on each interference signal.

First, the tomographic image generation unit 13311 removes fixed-pattern noise from the interference signal. The fixed-pattern noise is removed by averaging detected A scan signals to extract the fixed-pattern noise and subtracting the noise from the input interference signal. The tomographic image generation unit 13311 then performs desired window function processing in order to optimize the depth resolution and the dynamic range, which have a trade-off relationship when subjected to Fourier transform over a finite interval. The tomographic image generation unit 13311 then performs FFT processing to generate a tomographic signal.

<Step S1504>

Figure 19:
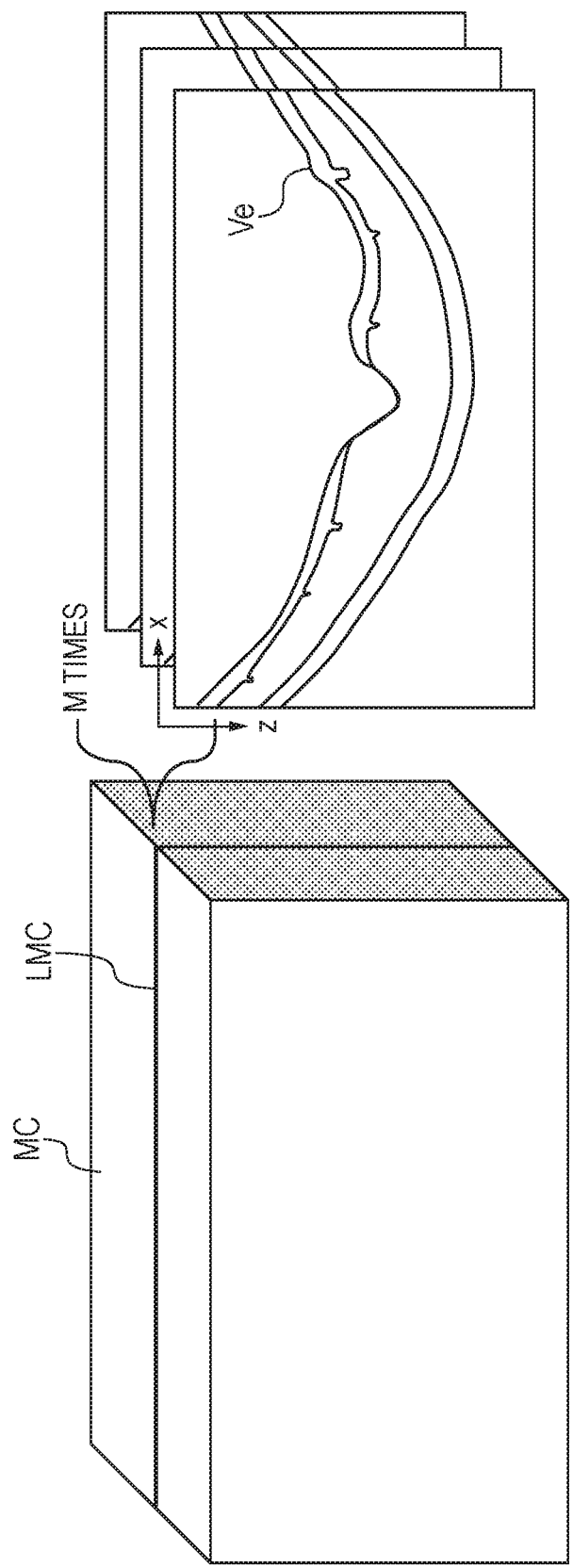
FIG. 19 describes motion contrast data generation.

At step S1504, the motion contrast data generation unit 13312 generates motion contrast data. This data generation will be described with reference to FIG. 19. FIG. 19 illustrates three-dimensional motion contrast data MC and two-dimensional motion contrast data LMC that constitutes the three-dimensional motion contrast data. Here, a method of generating the two-dimensional motion contrast data LMC will be described.

The motion contrast data generation unit 13312 first corrects misalignment between tomographic pictures imaged in the same range of the eye to be inspected. The misalignment may be corrected in any manner. For example, the motion contrast data generation unit 13312 performs alignment for tomographic image data sets corresponding to the same location, which are acquired by imaging same range M times, using a feature such as the fundus shape. Specifically, one of the M tomographic image data sets is selected as a template. While the position and angle of the template are varied, the degrees of similarity to the other tomographic image data sets are obtained to determine the amounts of misalignment with the template. The motion contrast data generation unit 13312 then corrects each tomographic image data set based on the determined amounts of misalignment.

The motion contrast data generation unit 13312 then determines a decorrelation value Mxz with Expression (1) between every two tomographic image data sets imaged at adjacent time points.

The motion contrast data generation unit 13312 can determine multiple decorrelation values Mxz at the same position (x, z) if the number M of repetitions of acquisition at the same position is three or more. The motion contrast data generation unit 13312 can statistically process the determined decorrelation values Mxz, such as by calculating the maximum or average, to generate final motion contrast data. If the number M of repetitions is two, no statistic processing such as maximum or average calculation is performed. Rather, the decorrelation value Mxz between the two adjacent tomographic pictures A and B is used as the motion contrast value at the position (x, z).

The expression for the motion contrast calculation as shown in Expression (1) tends to be noise-sensitive. For example, if the multiple tomographic image data sets contain noise of different values in signal-free portions, the decorrelation values will be high and the noise will be superimposed on the motion contrast images. To avoid this, the motion contrast data generation unit 13312 can perform preprocessing in which tomographic data sets having values below a predetermined threshold are regarded as noise and replaced with zero. This enables the image generation unit 13332 to generate, based on the generated motion contrast data, motion contrast images with reduced influence of noise.

The above-described processing from step S1502 to step S1504 can be repeated predetermined times to acquire multiple three-dimensional tomographic images and multiple three-dimensional motion contrast data sets. Using these acquired data sets, the image processing unit 1333 generates high-quality-image data at step S1505. A display format for data selection and execution for generating the high-quality-image data will be described later (step S1506). Here, processing performed by the image processing unit 1333 will be described with reference to the flowcharts in FIGS. 15B and 16 to 18 and FIGS. 19 to 27B.

<Step S1551>

At step S1551, the detection unit 13333 detects boundary lines between the retina layers in the tomographic images captured by the tomographic image capturing apparatus 1320. The detection unit 13333 detects, in the tomographic images as in FIG. 14B, either the boundaries L1 to L6 or the boundaries of GCL/IPL, IPL/INL, INL/OPL, and OPL/ONL (not shown) in the following manner. A tomographic image to be processed is subjected to a median filter and a Sobel filter to generate respective images (hereinafter referred to as a median image and a Sobel image). From the generated median image and Sobel image, a profile is generated for each A scan. The profiles in the median image are luminance value profiles, and the profiles in the Sobel image are gradient profiles. Peaks in the profiles generated from the Sobel image are detected. By referring to profiles in the median image corresponding to the positions before and after the detected peaks and between the peaks, the boundaries between the retina layer regions are detected.

<Step S1552>

At step S1552, the image generation unit 13332 projects, onto a two-dimensional plane, the motion contrast data corresponding to the range between the upper edge and the lower edge of the generation range that are set for the three-dimensional motion contrast data, thereby generating OCTA images. Specifically, based on the motion contrast data corresponding to the range between the upper edge and the lower edge of the generation range in the entire motion contrast data, the image generation unit 13332 performs processing such as Average Intensity Projection (API) or Maximum Intensity Projection (MIP) on the motion contrast data in that range to generate OCTA images, which are front images of the motion contrast images. The generation of the OCTA images may not be based on the average or maximum but may be based on a value such as the minimum, median, variance, standard deviation, or sum.

In this embodiment, it is assumed that the upper edge of the generation range is the ILM/NFL boundary line, and the lower edge of the generation range is the boundary line located at 50 μm from the GCL/IPL in the depth direction. The OCTA images are generated with Average Intensity Projection.

Alternatively, the motion contrast data generation unit 13312 may be configured to generate the motion contrast data using the tomographic data in the range between the upper edge and the lower edge of the generation range. In this case, the image generation unit 13332 can generate OCTA images based on the generated motion contrast data, so that the OCTA images based on the tomographic data with the set depth range can be generated.

<Step S1553>

At step S1553, alignment in the horizontal direction (x-axis) and vertical direction (y-axis), and rotational alignment on the xy plane, are performed between the N OCTA images. This will be described with reference to the flowchart in FIG. 16.

<Step S15531>

Figure 20A:
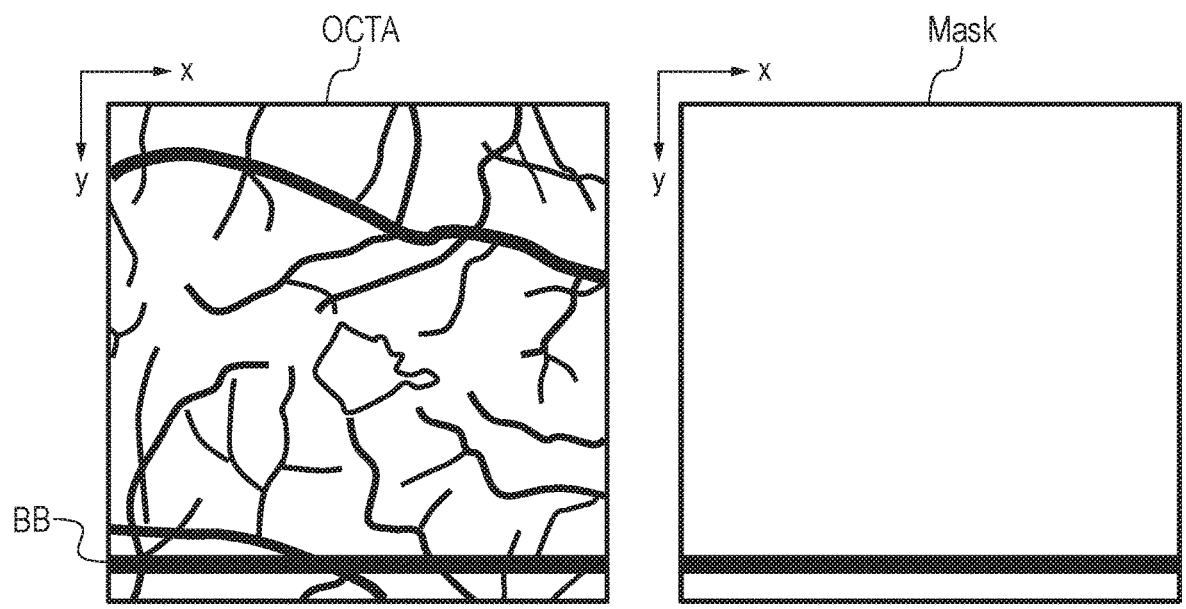
FIG. 20A and FIG. 20B describe artifact removal.
Figure 20B:
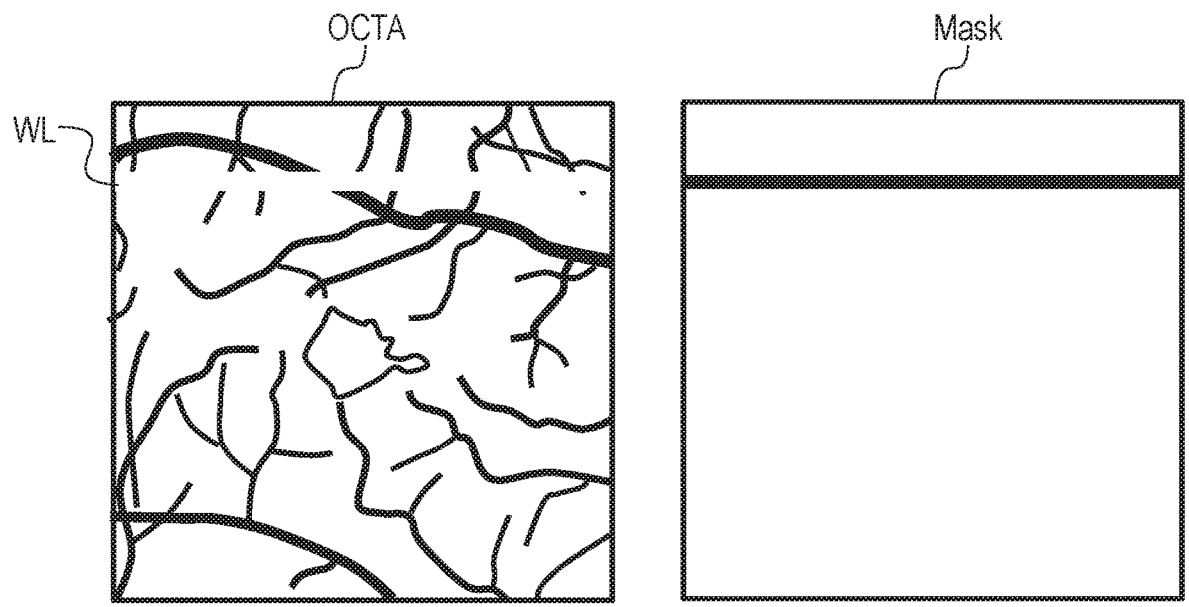

At step S15531, the preprocessing unit 13331 detects and deletes artifacts such as black bands and white lines from the OCTA images generated by the image generation unit 13332. This will be described with reference to FIGS. 20A and 20B. In FIGS. 20A and 20B, the black areas in the OCTA image represent where the decorrelation value is high, i.e., where blood flows are detected (corresponding to blood vessels), whereas the white areas represent where the decorrelation value is low. FIG. 20A shows an exemplary black band BB, and FIG. 20B shows an exemplary white line WL. A black band appears due to a decrease in decorrelation value, which occurs when the subject's movement during the imaging causes the retina to be apart from a highly sensitive position to reduce the luminance value of the retina tomographic picture, or when the entire image is darkened by a cause such as a blink. A white line appears due to an increase in decorrelation value in the entire image, which occurs when the alignment between the M tomographic pictures for decorrelation calculation fails or cannot completely correct misalignment. Since these artifacts occur in the decorrelation calculation, each artifact appears as a single line in the main scanning direction. Therefore, the preprocessing unit 13331 detects the artifacts in units of lines.

For example, a black band is detected if the average decorrelation value for a line is equal to a threshold $TH_{AVG\_B}$ or less. A white line is detected if the average decorrelation value for a line is equal to a threshold $TH_{AVG\_W}$ or more and if the standard deviation (or variance) is equal to $TH_{SD\_W}$ or less. The reason why the detection of a white line does not rely only on the average is as follows. A high decorrelation value may occur at features such as a great vessel, and a region containing such a blood vessel with a high decorrelation value might be erroneously detected as a white line. To prevent such erroneous detection, the average is combined with an index for evaluating the variation of values, such as the standard deviation or variance. Specifically, a line containing a blood vessel with a high decorrelation value will have a high average and also a high standard deviation. In contrast, a white line will have a high average but a low standard deviation due to a narrow variation of values. In an OCTA image, the decorrelation value depends on whether the eye is healthy or diseased, and further on the type of the disease. Therefore, the thresholds may be set for each image, or may be varied with the brightness of the OCTA image using dynamic thresholding, such as P-tile or discriminant analysis. If dynamic thresholding is used, the upper and lower thresholds are preset, and if the decorrelation value is above or below these thresholds, the upper or lower threshold of the value is set as the threshold.

The preprocessing unit 13331 stores the above-determined artifact regions in Mask images corresponding to the OCTA images. The Mask images shown illustrates an example in which 1 is set in the white area and 0 is set in the black area.

<Step S15532>

At step S15532, the first alignment unit 13334 initializes a two-dimensional matrix for saving alignment parameters resulting from the alignment of the OCTA images. Information necessary for improving the image quality, such as deformation parameters used in the alignment and the degrees of image similarity, is collectively saved in each element of the matrix.

<Step S15533>

Figure 21A:
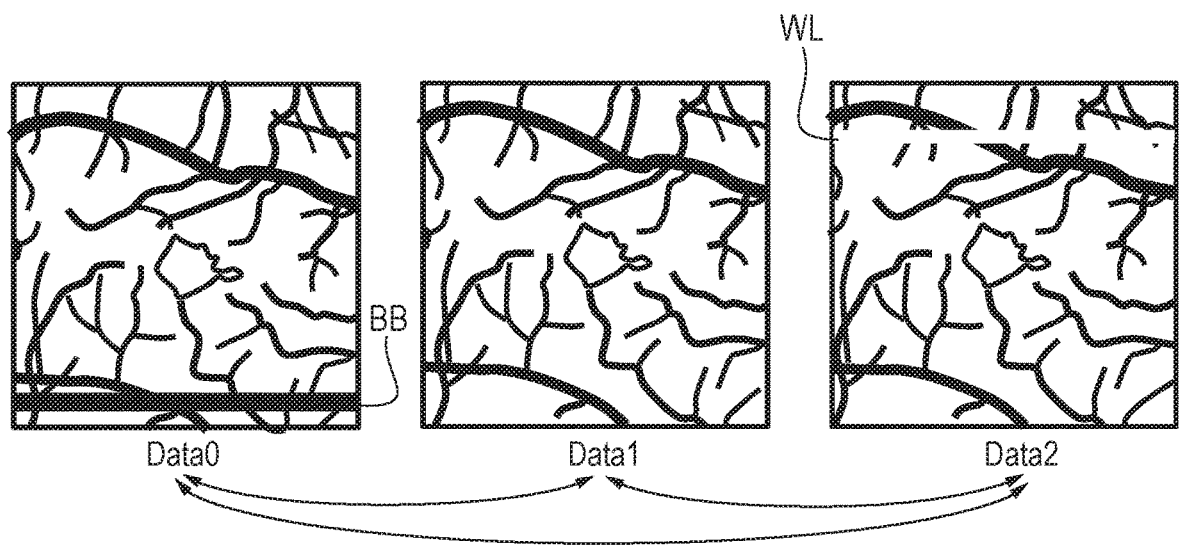
FIG. 21A and FIG. 21B describe first alignment.
Figure 21B:
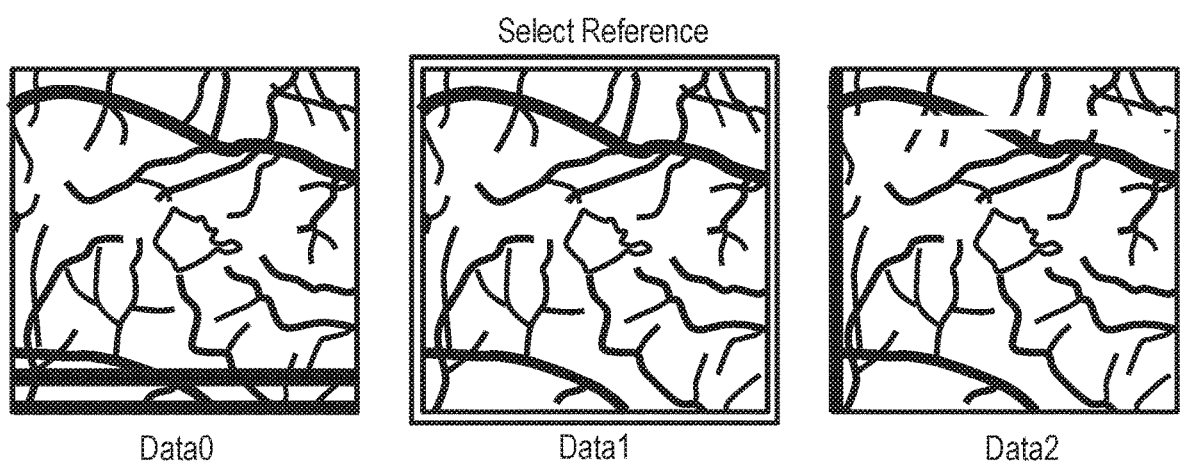

At step S15533, the first alignment unit 13334 selects alignment targets. In this embodiment, each OCTA image is set as the reference image to be aligned with the rest of the OCTA images. Therefore, at step S15533, for the reference OCTA image of Data 0, alignment is performed with each image of Data 1 to Data (N−1). Then, for the reference OCTA image of Data 1, alignment is performed with each image of Data 2 to Data (N−1). Then, for the reference OCTA image of Data 2, alignment is performed with each image of Data 3 to Data (N−1). This processing is repeated. FIG. 21A illustrates an example of this processing. Although FIGS. 21A and 21B show Data 0 to Data 2 for simplicity, the alignment is performed between N OCTA images in the case of N times of three-dimensional volume imaging.

As the reference image Data is incremented by one as illustrated here, the start Data as the alignment target image is also incremented by one. This will be described for the case where the OCTA image of Data 2 is the reference. For the reference of Data 2, alignment between Data 0 and Data 1, Data 0 and Data 2, and Data 1 and Data 2 has been performed in the previous process. Therefore, for the reference OCTA image of Data 2, alignment may start at Data 3. Thus, despite alignment between all OCTA images, calculation is required for only half of the combinations.

<Step S15534>

At step S15534, the first alignment unit 13334 performs alignment in the horizontal direction (x-axis) and vertical direction (y-axis), and rotational alignment on the xy plane, between the OCTA images. In the alignment between the OCTA images, the size of the OCTA images is enlarged for performing sub-pixel alignment on the xy plane. With the sub-pixel alignment, more precise alignment is expected than with pixel alignment. For example, the OCTA images of an imaging size of 300×300 are enlarged to images of 600×600. An interpolation method such as Bicubic or Lanczos (n) is used for enlarging. For the alignment processing between the images, for example, an evaluation function representing the degree of similarity between two OCTA images is predefined. Evaluation values are calculated while the OCTA images are translated and rotated, and the position where the best evaluation value is obtained is regarded as the alignment result. As the evaluation function, a function based on an evaluation method in terms of pixel values may be used (for example, an evaluation method using a correlation coefficient).

As an evaluation function representing the degree of similarity, Expression (6) illustrates an expression using a correlation coefficient.

$$\frac{\iint_s (f(x, y) - \bar{f})(g(x, y) - \bar{g}) dx dy}{\sqrt{\iint_s (f(x, y) - \bar{f})^2 dx dy \iint_s (g(x, y) - \bar{g})^2 dx dy}} \quad (6)$$

In Expression (6), f(x, y) denotes a region in the OCTA image of Data 0, and g(x, y) denotes a region in the OCTA image of Data 1.

$\bar{f}, \bar{g}$ respectively denote the averages in the region f(x, y) and the region g(x, y). Here, a region is an image region for use in the alignment. A region of the size not larger than the OCTA image, typically a region of the above-described ROI size, is set.

In addition to the above evaluation function, other evaluation functions capable of evaluating the degree of similarity or difference between images may be used, such as SSD (Sum of Squared Difference) and SAD (Sum of Absolute Difference). Alternatively, the alignment may be performed with a method like POC (Phase Only Correlation). Thus, the global alignment on the XY plane is completed with the above processing.

Although the example illustrated here performs the alignment by enlarging the size of the OCTA images, this is not limitation. The enlargement may not be necessary in the case of high-density scan in which the input OCTA images have a size such as 900×900. For fast alignment, pyramid-structured data may be generated to perform the alignment.

<Step S15535>

At step S15535, the first alignment unit 13334 calculates image evaluation values of the OCTA image. For the OCTA images two-dimensionally aligned at step S15534, the image evaluation values are calculated using regions common to the images excluding invalid regions resulting from the alignment. For example, the image evaluation value Q can be obtained with Expression (7).

$$Q = \frac{\sigma_{fg}}{\sigma_f \sigma_g} \cdot \frac{2\bar{f}\bar{g}}{(\bar{f})^2 + (\bar{g})^2} \cdot \frac{2\sigma_f \sigma_g}{\sigma_f^2 + \sigma_g^2} \quad (7)$$

For Expression (7), it is assumed that f(x, y) denotes the region in the OCTA image of Data 0, and g(x, y) denotes the region in the OCTA image of Data 1. The first term represents a correlation coefficient as in Expression (6). Therefore, $\sigma_f$ and $\sigma_g$ in the expression respectively correspond to the values shown in Expression (6). The second term evaluates the brightness, and $\bar{f}, \bar{g}$ respectively represent the averages in the region f(x, y) and the region g(x, y). The third term evaluates the contrast. Each term ranges from the minimum 0 to the maximum 1. For example, If Data 0 and Data 1 are identical images, the evaluation value is 1. Accordingly, the evaluation value will be high if an average image among the N OCTA images is set as the reference, whereas the evaluation value will be low if an OCTA image that is distinct from the other OCTA images is set as the reference. Here, an image that is distinct from the other OCTA images is such an image that shows a different imaged location, is skewed, is generally too dark or bright, or contains an artifact such as a white line or a black band. The image evaluation value may not necessarily be obtained with the expression indicated here; each term may be individually evaluated or the terms may be differently combined.

<Step S15536>

At step S15536, the first alignment unit 13334 saves values in the two-dimensional matrix initialized at step S15532, which is a matrix for saving parameters necessary for improving the image quality, such as the alignment parameters and the degrees of image similarity. For example, for Data 0 as the reference image and Data 1 as the target image, parameters are saved in the element (0, 1) of the two-dimensional matrix, including the horizontal alignment parameter X, the vertical alignment parameter Y, the rotation parameter a on the XY plane, the image evaluation value, and the degree of image similarity. In addition to these pieces of information, the Mask image shown in FIGS. 20A and 20B are saved in association with the OCTA image.

Further, although not described in this embodiment, the scaling factor may be saved if scale correction is performed.

<Step S15537>

At step S15537, the first alignment unit 13334 determines whether or not all images have been used as the reference image to perform the alignment with the rest of the images as target images. If not all images have been used as the reference to perform the processing, the process returns to step S15533. If all images have been used as the reference to perform the processing, the process proceeds to step S15538.

<Step S15538>

At step S15538, the first alignment unit 13334 updates the remaining elements of the two-dimensional matrix. As described with respect to step S15533, the calculation in the above processing has only been performed for half of the combinations. Therefore, values are copied into the elements for which the calculation has not been performed. For example, the parameters in the element (0, 1) of the two-dimensional matrix are copied into the element (1, 0). That is, the element (i, j) is copied into the element (j, i). In doing so, since the alignment parameters X and Y and the rotation parameter a are to be inverted, these parameters are multiplied by a negative value and copied. Parameters such as the degree of image similarity are not to be inverted, so that the values are simply copied. Thus, the OCTA images are aligned with the above processing. Now, the description returns to the process flow in FIG. 15B.

<Step S1554>

At step S1554, the selection unit 13335 selects a reference image. The reference image is selected based on the result of the alignment performed at step S1553. The two-dimensional matrix has been generated at step S1553, and the elements of the matrix contain the information necessary for generating images of improved quality. This information is used to select the reference image. The reference image is selected using an image evaluation value, an alignment parameter evaluation value, and an artifact region evaluation value. The image evaluation value is a value obtained using the values determined at step S15535. The alignment parameter evaluation value is a value obtained with X and Y resulting from the alignment at step S15534, for example with Expression (8). Expression (8) yields a larger value for a larger amount of shifting.

$$SV = \sqrt{X^2 + Y^2} \quad (8)$$

The artifact region evaluation value is a value obtained with the Mask images created at step S15531, for example with Expression (9). In Expression (9), T(x, y) denotes pixels in artifact-free areas in the Mask image, and A(x, y) denotes all pixels in the Mask image. Therefore, in the absence of artifacts, the expression yields the maximum 1.

$$NA = \frac{\sum_{(x,y)}^{n} T_{(x,y)}}{\sum_{(x,y)}^{n} A_{(x,y)}} \quad (9)$$

The image evaluation value and the artifact region evaluation value are desirably larger, and the alignment parameter evaluation value is desirably smaller. The image evaluation value and the alignment parameter evaluation value are determined based on the relationships between an image as the reference and the other images, so that these evaluation values are the sums of N−1 values. Since the evaluation values are different in evaluation measure, the values involved in each evaluation value are sorted to select the reference image based on the sum of the sorted indices. For example, for each of the image evaluation value and the artifact region evaluation value, the indices are sorted so that the larger the value, the smaller the sorted indices. For the alignment parameter evaluation value, the indices are sorted so that the smaller the value, the smaller the sorted indices. The image with the smallest sorted index values is selected as the reference image.

Although the described example selects the reference image by summing the sorted values, this is not limitation. Each evaluation value may be calculated by weighting the sorted indices.

Instead of the sorted values, the calculation may involve normalizing each evaluation value to 1. For example, while the image evaluation value is normalized to 1, the average may be used because the image evaluation value is the sum of N−1 values in this embodiment.

The alignment parameter evaluation value can be normalized to 1 by defining as in Expression (10). In this case, the evaluation value nearer 1 is better.

$$NSV_n = 1.0 - \alpha \frac{SV_n}{SV_{max}} \quad (10)$$

In Expression (10), $SV_n$ is the sum of the N−1 values obtained with Expression (8). The subscript n corresponds to the Data number, such that the sum for Data 0 is $SV_0$. $SV_{max}$ is the maximum alignment parameter evaluation value among Data 0 to Data (N−1). α is a weight that is a parameter for adjusting the value of $NSV_n$ when $SV_n$ and $SV_{max}$ are the same value. The maximum $SV_{max}$ may be determined from the actual data as described above, or may be predefined as a threshold.

The artifact region evaluation value is normalized to 0 to 1 and therefore may be used as it is.

With all evaluation values normalized to 1 as above, the image with the largest sum of the evaluation values is selected as the reference image.

As described here, the image selected as the reference best satisfies the conditions that the image is an average image among the N images, the other images are required to be shifted little in the alignment, and the image contains few artifacts. FIG. 21B illustrates an exemplary reference image selected according to this example. In this example, Data 1 is selected as the reference image. Data 0 and Data 2 have been shifted based on the alignment parameters determined by the first alignment unit 13334.

<Step S1555>

Figure 22A:
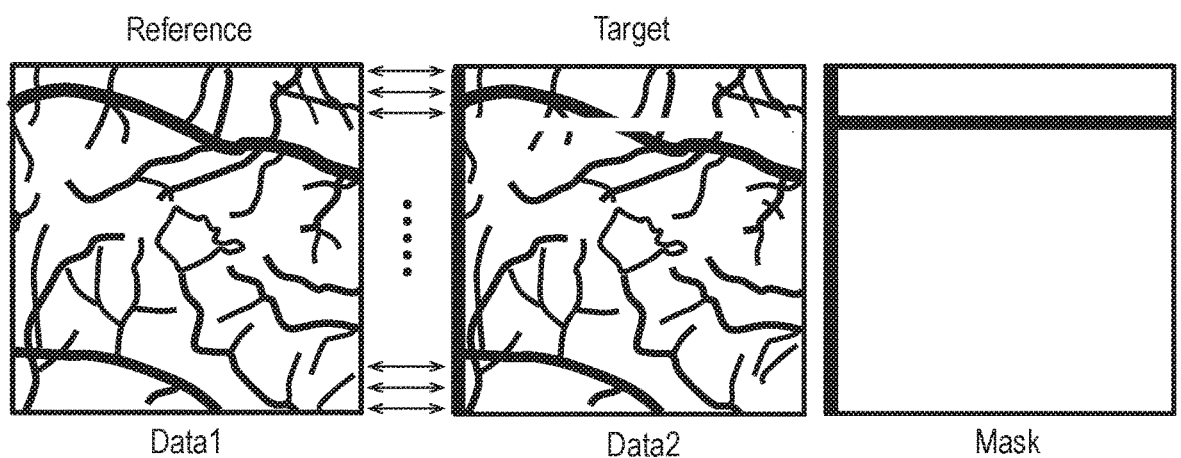
FIG. 22A and FIG. 22B describe second alignment.

At step S1555, the second alignment unit 13336 performs alignment of the retina in the horizontal direction (x-axis) using the OCTA images. This will be described with reference to FIGS. 22A and 22B. FIG. 22A illustrates an example of the horizontal alignment between Data 1 as the reference image and Data 2 as the alignment target. In Mask, 0 is set in the region of an artifact contained in Data 2 (the horizontal black line in the figure), and an invalid region created by shifting of Data 2 as a result of the alignment with Data 1 (the vertical black line in the figure). The reference image and the alignment target image are horizontally aligned line by line to calculate the degree of similarity of each line. The degree of similarity is calculated with Expression (6), for example, and the lines are shifted to a position where the maximum degrees of similarity are achieved. Also, a weight is set in Mask according to the degree of similarity to the reference image calculated for each line.

Figure 22B:
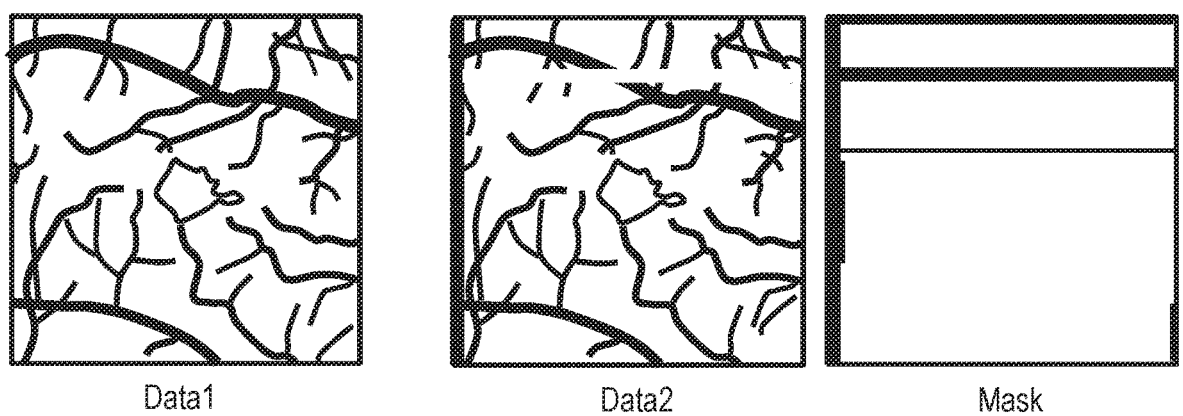

FIG. 22B illustrates an example of the result of the alignment performed by the second alignment unit 13336. In the example shown in FIG. 22B, the target image is determined not to be similar to the reference image at the upper edge and around the center of the image, so that horizontal black lines are set in the Mask image as lines not to be used for superimposition. This example also shows that a region around the center of the image is shifted to the left and a region at the lower edge of the image is shifted to the right as a result of the line-by-line alignment. Since the shifting creates invalid regions, 0 is set in the invalid regions in Mask. Thus, the local alignment on the XY plane is completed with the above processing.

The rotation parameter a obtained in the first alignment may be applied to each image either before or after the second alignment.

<Step S1556>

At step S1556, the third alignment unit 13337 performs alignment in the depth direction (z-direction) between the reference three-dimensional data set and the other three-dimensional data sets. This processing will be described with reference to the flowchart in FIG. 17.

<Step S15561>

At step S15561, the third alignment unit 13337 stores three-dimensional motion contrast data to be used as the reference and three-dimensional tomographic image data to be used as the reference. For example, in this embodiment, the motion contrast data and three-dimensional tomographic image data of Data 1 are stored.

<Step S15562>

At step S15562, the third alignment unit 13337 acquires the boundary line information detected at step S1551. In this embodiment, the boundary line L1 is used for the depth-direction alignment.

<Step S15563>

Figure 23A:
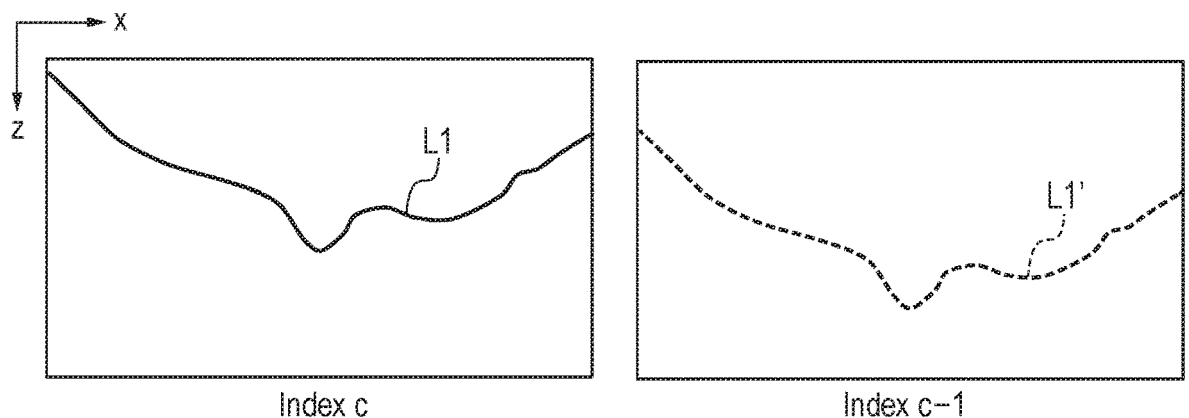
FIG. 23A, FIG. 23B, and FIG. 23C describe third alignment.

At step S15563, the third alignment unit 13337 aligns the position and tilt in the depth direction for each three-dimensional data set. The eye is moving during imaging of a three-dimensional tomographic picture. Movements on the XY plane are tracked in real time during the imaging and therefore almost aligned at the time of imaging. However, movements in the depth direction are not tracked in real time and therefore need to be aligned within each data set. That is, the description here relates to alignment within a single three-dimensional data set. This will be described with reference to FIGS. 23A to 23C. FIG. 23A illustrates an exemplary boundary line used for the alignment. In this embodiment, the case of using the boundary line L1 (ILM) will be described. Although the example of using the boundary line L1 is described in this embodiment, the boundary line used is not limited to the boundary line L1. Another boundary line or a combination of boundary lines may be used.

In FIG. 23A, Index c is the reference data and Index c−1 is the target data. The initial reference data is the boundary line data in the center of the three-dimensional data, and the initial target data is the boundary line data adjacent to the reference data in the sub-scanning direction.

Figure 23B:
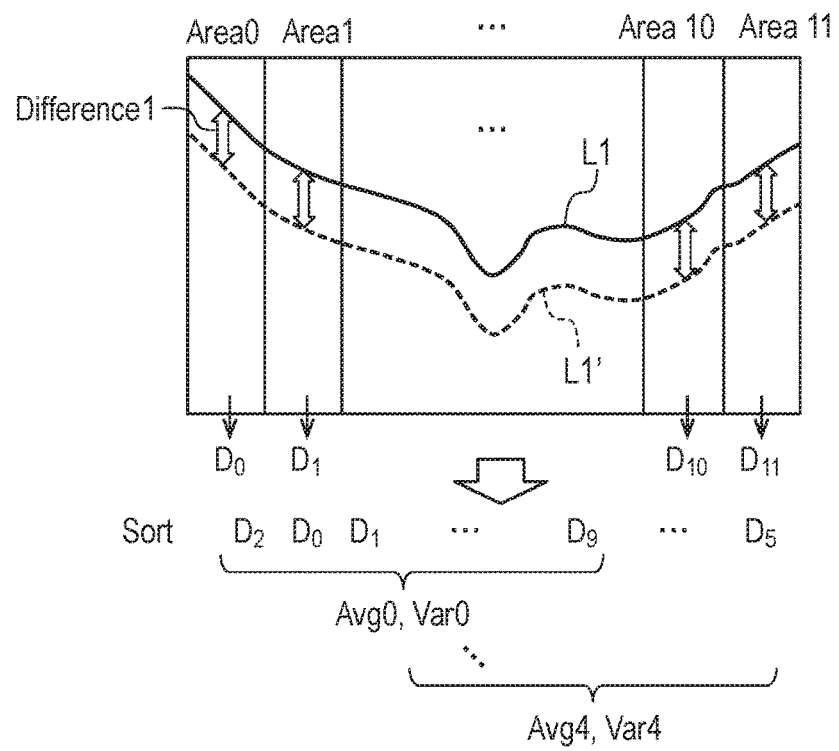

For illustrative purposes, FIG. 23B simultaneously shows the boundary line L1 of the reference data and the boundary line L1' of the alignment target. In FIG. 23B, the boundary lines are vertically divided into 12 areas. In the description of this embodiment, the number of divided areas is 12: Area 0 to Area 11. Although FIG. 23B depicts no divided areas in the center of the image, the entire image is actually divided into the areas. Up-down arrows Difference 1 represent the differences between the boundary line L1 and the boundary line L1'. These differences are determined in the respective areas Area 0 to Area 11. The number of divided areas may depend on the width of the image or on the horizontal length of the simultaneously detected boundary lines. Although the boundary lines are shown as having the same horizontal length in this embodiment for simplicity, actually the retina layers may be displaced upward in the image (toward 0 on the Z-axis) and a partial region of the retina layers may be missing in the image. In that case, the boundary line cannot be detected across the entire width of the image. Therefore, in the alignment between the boundary lines, the range in which both the boundary line L1 of the reference data and the boundary line L1' of the alignment target are successfully detected may be divided into areas to perform the alignment.

Figure 23C:
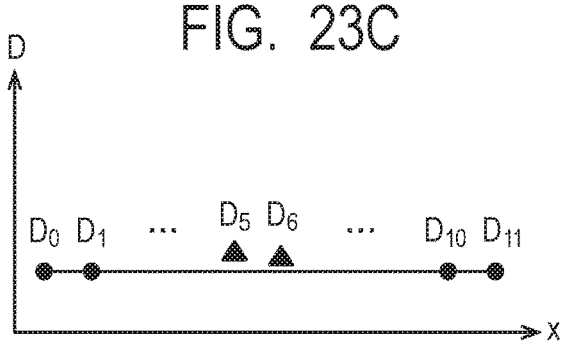

In FIG. 23B, $D_0$ to $D_{11}$ are the averages of Difference 1 in the respective areas. That is, the average of the ILM differences in each area is regarded as the representative difference value in that area. Then, the representative values $D_0$ to $D_{11}$ obtained in the respective areas are sorted in increasing order. Eight of the sorted representative values are used sequentially from the smallest value to calculate the average and the variance. Although eight values are selected in this embodiment, the number of selected values is not limited to eight. Any number of values, below the number of divided areas, may be selected. The average and the variance are calculated while the eight sorted representative values are shifted by one. Since the representative values of eight divided areas out of the 12 divided areas are used for the calculation in this embodiment, five pairs of averages and variances are obtained in total. Then, the eight representative difference values providing the smallest variance among the calculated five variances are used to determine the shift value and tilt in the depth direction. This will be described with reference to FIG. 23C and Expression (11). FIG. 23C is a graph in which the abscissa indicates the x-coordinate of the center of each divided area and the ordinate indicates the representative difference values. In FIG. 23C, the black circles indicate an example of the combination of representative difference values providing the smallest variance, and the black triangles indicate an example of unselected representative difference values. Expression (11) is calculated using the combination of representative difference values providing the smallest variance (the black circles in FIG. 23C).

$$D = ax + b \tag{11}$$

$$a = \frac{n\sum_{i=1}^{n} x_i D_i - \sum_{i=1}^{n} x_i \sum_{i=1}^{n} D_i}{n\sum_{i=1}^{n} x_i^2 - \left(\sum_{i=1}^{n} x_i\right)^2} \tag{12}$$

$$b = \frac{\sum_{i=1}^{n} x_i^2 \sum_{i=1}^{n} D_i - \sum_{i=1}^{n} x_i D_i \sum_{i=1}^{n} x_i}{n\sum_{i=1}^{n} x_i^2 - \left(\sum_{i=1}^{n} x_i\right)^2} \tag{13}$$

In Expression (11), D denotes the shift value in the depth direction, and x denotes an x coordinate, i.e., the position of an A scan. Expression (12) and Expression (13) show a and b in Expression (11). In Expression (12) and Expression (13), x denotes the x coordinate of the center of a selected divided area, $D_i$ denotes a selected representative difference value, and n denotes the number of selected representative values, which is eight in this embodiment. From Expression (11), the shift value in the depth direction of each A scan is determined.

As illustrated here, in the boundary line alignment, the images are divided into areas, and the combination of difference values in the divided areas providing the narrowest variation is used. In this manner, even if some areas contain an erroneously detected boundary line, values in those areas will not be used. This allows stable calculation of the shift value in the depth direction. Although the average is used as the depth-direction representative value in each area, the median or any representative value may be used instead. Further, although the variance is used as the value representing the variation, the standard deviation or any index capable of evaluating the variation of values may be used.

In this processing, all data sets are aligned while the reference data and the target data are changed. Specifically, the initial reference data is the boundary line data in the center of the three-dimensional data, and the initial target data is the boundary line data adjacent to the reference data. After this initial alignment, the target data is now used as the reference data to perform alignment with its adjacent data as the target data. When the processing is finished up to one end of the image, the boundary line data in the center is again used as the reference data to perform alignment with the adjacent boundary line data on the side opposite to the initially aligned side. The processing is performed up to the end of the images on the opposite side as well. If the layers fail to be detected in any data set, the alignment parameters for the previous data set are used to perform correction and the process proceeds to the next data set.

Figure 24A:
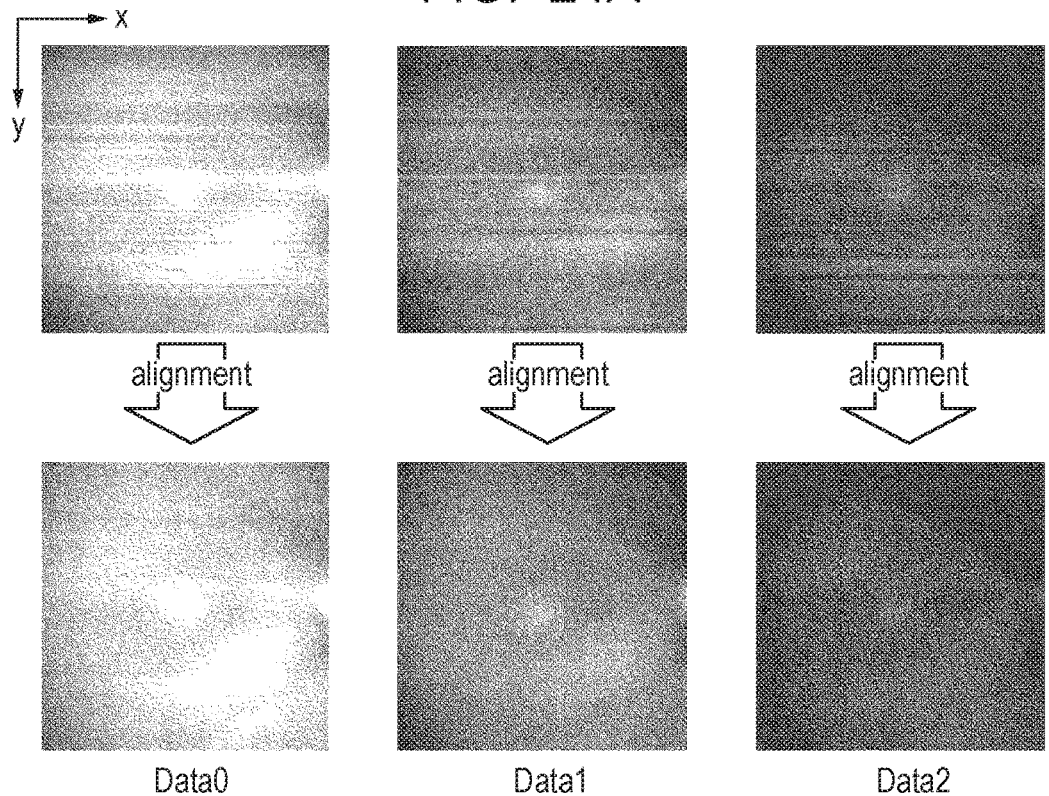
FIG. 24A and FIG. 24B describe the result of the third alignment.
Figure 24B:
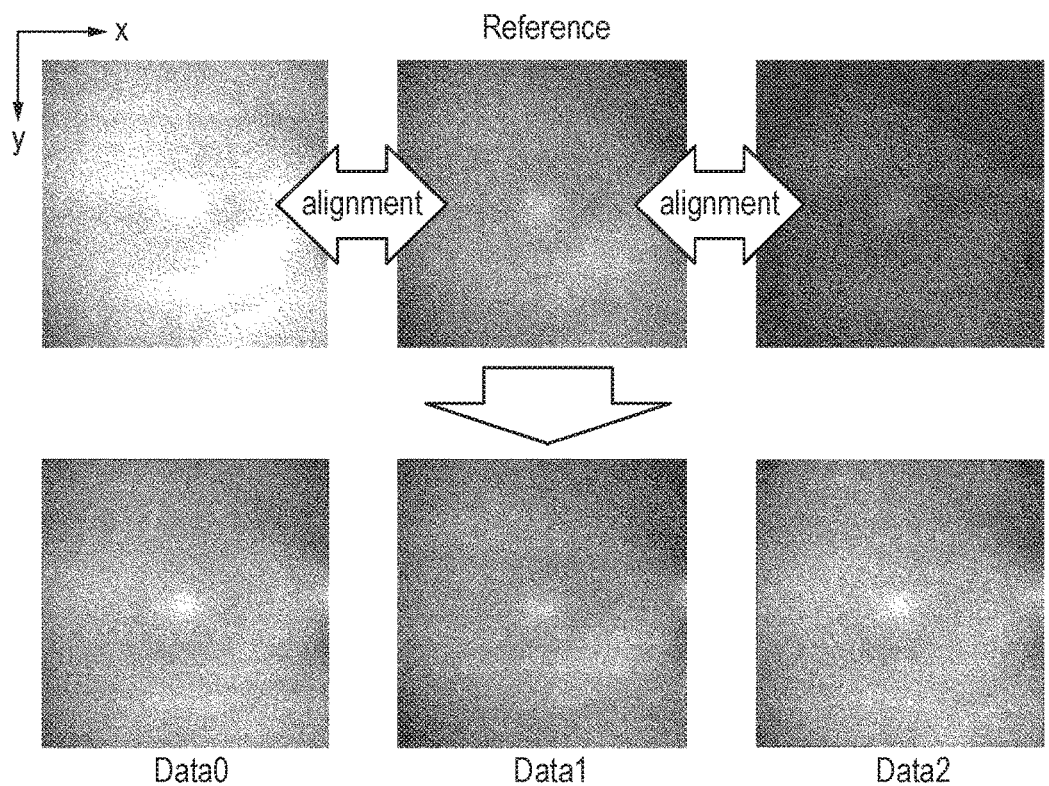

FIG. 24A illustrates an example of applying this processing. FIGS. 24A and 24B show depth maps in which the Z coordinates of the boundary line L1 are represented as luminance values. Thus, a brighter depth map indicates that the Z coordinate values are larger, and a darker depth map indicates that the Z coordinate values are smaller. FIGS. 24A and 24B show Data 0 to Data 2, in which the upper items are depth maps before the alignment and the lower items are depth maps after the alignment. All Data items of the depth maps before the alignment are unevenly colored in the horizontal direction, which suggests that the retina was moving in the Z direction during the imaging. In contrast, the depth maps after the alignment have no color unevenness, which indicates that positions are aligned in the Z direction between the adjacent data items. Although the above example of the depth-direction alignment involves the alignment of one side of the data and then the opposite side of the data, this is not limitation. Rather, both sides may be processed in parallel with the same initial reference data.

The third alignment unit 13337 stores the amount of shift in the depth direction of each A scan of the reference data (Data 1 in this embodiment).

<Step S15564>

At step S15564, the third alignment unit 13337 aligns the position and tilt in the depth direction between the multiple three-dimensional data sets. Here, the alignment between the three-dimensional data sets is performed using the data subjected to the depth-direction alignment within each three-dimensional data set at step S15563. Again, the boundary line L1 is used for the alignment as in the above case. Calculation is similar to the calculation at step S15563 but is performed between the data sets rather than within each data set. Therefore, the alignment is performed between the reference data and the target data. This will be described with reference to FIG. 24B. It is assumed in this embodiment that the reference data is Data 1, and the alignment target data is Data 0 and Data 2. The parameters obtained in the first and second alignment are applied to the depth maps to deform each of the depth maps of Data 0 and Data 2. For Data 1, along with Data 0 and Data 2, depth-direction alignment of the boundary line L1 corresponding to each B scan is performed. The calculation is performed in a manner similar to Expression (11).

FIG. 24B shows Data 0 to Data 2, in which the upper items are depth maps after the alignment within each data set, while the lower items are depth maps after the alignment between the data sets. The depth maps after the alignment within each data set vary in brightness due to the differences in Z position of the retina in Data 0 to Data 2. In contrast, the depth maps after the alignment between the data sets present the same brightness due to the aligned Z positions of the retina in Data 0 to Data 2.

Thus, the global alignment in the Z direction is completed with the above processing.

<Step S15565>

In step S15565, the third alignment unit 13337 applies the deformation parameters concerning the X, Y, Rotation, and Z calculated in the first alignment, the second alignment, and the third alignment and deforms the three-dimensional data. As the three-dimensional data, both of the tomographic image data and the motion contrast data are deformed. Note that, in step S15534, when the image is enlarged in the xy plane and the alignment is performed, the deformation parameters are reset to the deformation parameters equivalent to the original size when the three-dimensional data deformation is performed. That is, when a numerical value of an alignment parameter in the xy plane in an image enlarged to a double size is 1, the numerical value is reset to 0.5. The shape deformation of the three-dimensional data is performed in the original size.

In the conversion of the three-dimensional data, when the deformation parameters concerning X, Y, Rotation, and Z is a movement amount in one of a sub-pixel and a sub-voxel, the three-dimensional data is deformed by interpolation processing. The movement amount is in one of the sub-pixel and the sub-voxel, for example, when the movement amount is a real number value such as 0.5 or when the Rotation parameters are not 0 and data is rotated. A Bicubic or Lanczos(n) method or the like is used for the interpolation of the shape data.

Figure 25:
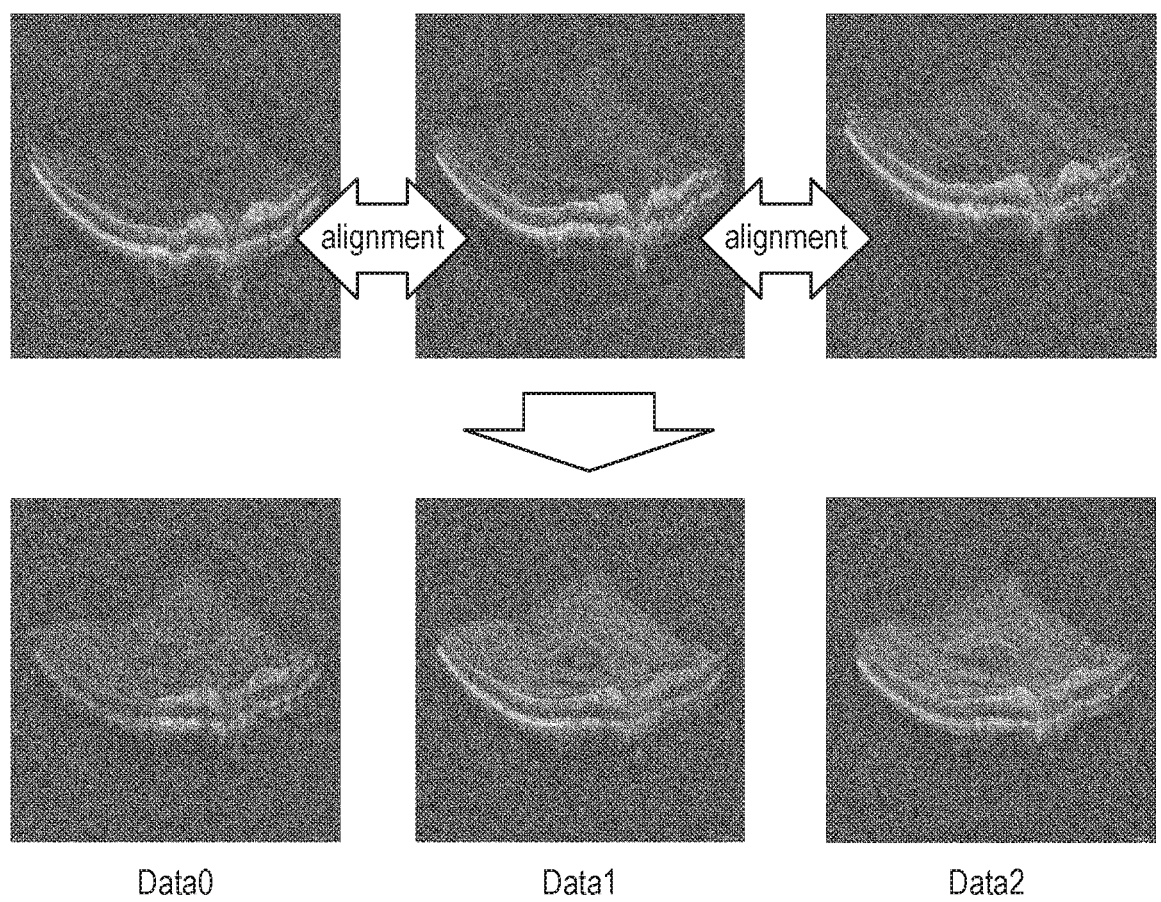
FIG. 25 describes the result of three-dimensional deformation of data.

FIG. 25 illustrates three-dimensional tomographic images of the Data 0 to the Data 2. The three-dimensional tomographic images on the upper side are three-dimensional tomographic images before the alignment is performed. The three-dimensional tomographic images on the lower side are three-dimensional tomographic image deformed after the first alignment, the second alignment, and the third alignment are performed. As illustrated in FIG. 25, the three-dimensional tomographic images after the alignment in the data and among the data indicate that the alignment concerning XYZ of the retina is performed in the Data 0 to the Data 2.

<Step S15566>

In step S15566, the third alignment unit 13337 performs detection of a difference between the reference data and the target data in the DepthMap in which the Z alignment among the data is performed. In a place (x, y) where the absolute value of the difference is equal to or larger than a threshold, the third alignment unit 13337 determines that accuracy of the alignment is low and does not use the target data in superimposition. Therefore, the third alignment unit 13337 sets 0 as an invalid region in a Mask image of the target data.

<Step S1557>

In step S1557, the fourth alignment unit 13338 sets a plurality of regions for alignment in characteristic portions inside the tomographic images between the reference data and the target data and performs alignment in the lateral direction (the x axis) and the depth direction (the z axis) of the retina in a unit of the regions. Note that the alignment is described as local alignment in the Z direction. The local alignment performed by the fourth alignment unit 13338 is described with reference to a flowchart of FIG. 18.

<Step S15571>

In step S15571, the fourth alignment unit 13338 acquires the boundary line information detected in step S1551. Note that boundary lines used in the depth direction alignment in this embodiment are the boundary line L1 and the boundary line L3.

<Step S15572>

In step S15572, the fourth alignment unit 13338 sets a region for alignment to include a characteristic region of the target image. This is described with reference to FIG. 26.

Figure 26:
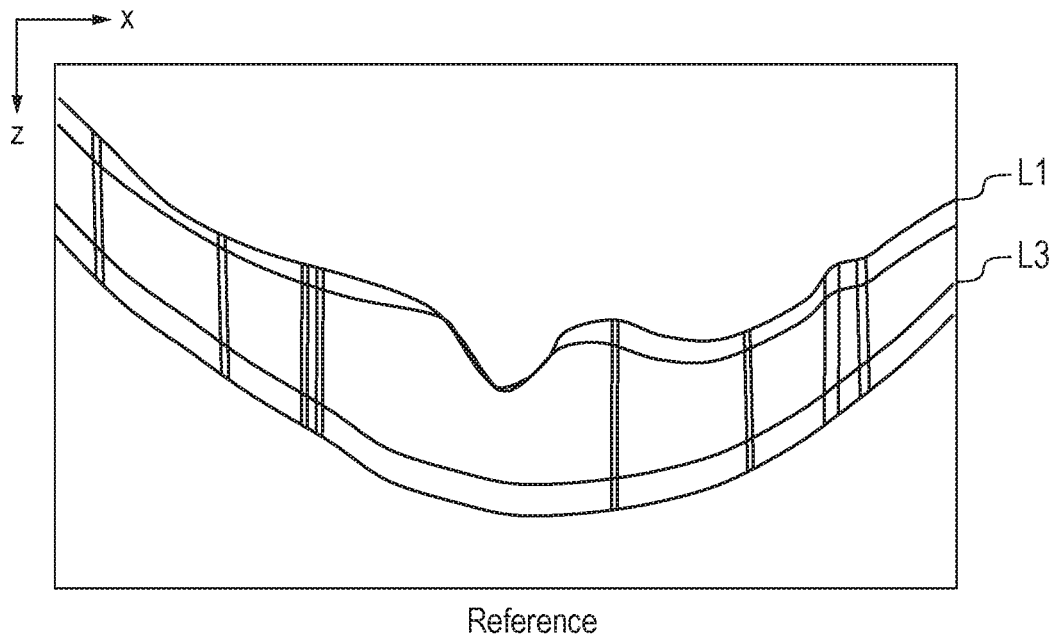
FIG. 26 describes fourth alignment.
Figure 26:
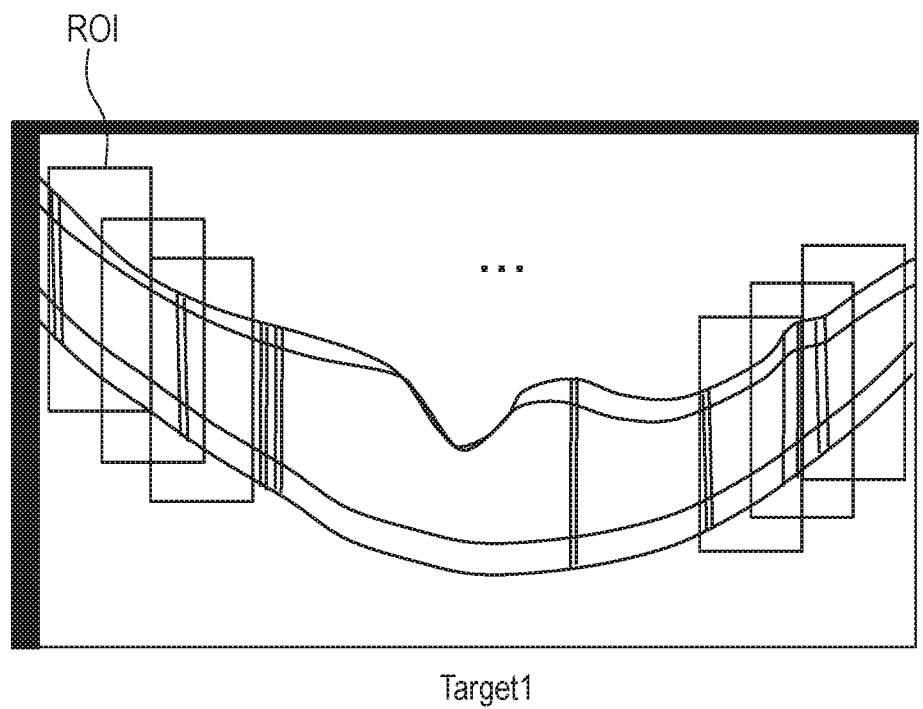

In FIG. 26, a tomographic image in the three-dimensional tomographic image of the reference data and a tomographic image in the three-dimensional tomographic image set as the alignment target are illustrated. In a target image 1 set as the alignment target, an example of a plurality of regions for alignment (ROIs: Regions of Interesting) set based on the boundary line information L1 and L3 of the reference tomographic image is illustrated. A depth direction size of the ROIs is set wider in the upward direction and the downward direction respectively by approximately several ten pixels than L1 and L3 based on L1 and L3. Note that, when parameters are set by approximately several ten pixels in the up-down direction, the parameters are sometimes corrected using a result of the general alignment. This is because an invalid region is sometimes present at the upper end portion of an image when the entire image is shifted in the downward direction in the general alignment as illustrated in the target image 1 in FIG. 26. In this case, an initial ROI size needs to be corrected such that a range in which the ROIs are set and a search region of the ROIs do not include the invalid region. A lateral direction size of the ROIs is set from a size of divided images. The number of divisions is set according to imaging parameters such as a size (the number of A scan lines) of the image and an imaging size (3 mm) of the image. For example, in this embodiment, when the number of A scan lines is set to 300 and the imaging size is set to 3 mm, the number of divisions is set to 10. Note that the size in the lateral direction and a setting value of the ROIs are also corrected using the result of the general alignment. Since an invalid region is sometimes present in the lateral direction as in the parameters in the up-down direction, a range in which the ROIs are set and a search region of the ROIs need to be set not to include the invalid region.

The ROIs for local alignment are set to be superimposed one top of another. This is because, when the size of the ROIs is reduced without superimposing the ROIs, a place not including characteristic parts is sometimes present in the ROIs. For example, when the retina is imaged at a narrow viewing angle, a flat tissue is imaged in a wide range in an image. On the other hand, this is because, when the range of the ROIs is set wide to include characteristics without superimposing the ROIs, a sampling number for local alignment decreases and rough alignment is performed. Therefore, in order to solve these problems, a size in the X direction of the ROIs is increased and the ROIs are set to be superimposed one on top of another. Note that, in FIG. 26, the ROIs are not drawn in the center of the image. However, actually, the ROIs are set on the retina from the left end to the right end of the image. Further, an interval of the setting of the ROIs can be set considering a search range during ROI alignment. Specifically, when a lateral-direction search range during the ROI alignment is represented as XR, an interval between center coordinates of ROIs adjacent to each other is set to be 2XR or more. This is because, when the interval between the center coordinates is set to less than 2XR, the center positions of the ROIs adjacent to each other are likely to be interchanged.

<Step S15573>

In step S15573, the fourth alignment unit 13338 performs region alignment using the ROIs. The region alignment is performed in a tomographic image. Therefore, the fourth alignment unit 13338 performs alignment corresponding to image similarity using Expression (1) as in the OCTA image alignment illustrated in step S15534. However, not only this, but an evaluation value of similarity may be an SSD (Sum of Squared Difference), an SAD (Sum of Absolute Difference), or the like. Alternatively, the alignment may be performed by a method such as a POC (Phase Only Correlation).

The image alignment searches where the ROIs set in the target image are present in the reference tomographic image. In this case, since the deformation of the three-dimensional tomographic image data is performed by the first alignment to the third alignment, approximate positions of the reference image and the target image are aligned. Therefore, as the search range of alignment in the reference image, several to several ten pixels in upward, downward, left, and right directions from initial positions of the ROIs only have to be searched. Most similar places are adopted as an alignment result. Note that a search region may be fixed or may be changed according to an imaging viewing angle, an imaging part, and a place (an end or a center) in an image. When the imaging viewing angle is narrow and scan speed is high, a movement among of the eye during imaging of one image is small. However, when the imaging viewing angle is wide, the movement amount of the eye is large. Therefore, the search range may be increased when the imaging viewing angle is large. The movement amount is larger in a peripheral portion than a center portion of rotation of the eye. Therefore, the search range may be set wide in the peripheral portion.

<Step S15574>

Figure 27A:
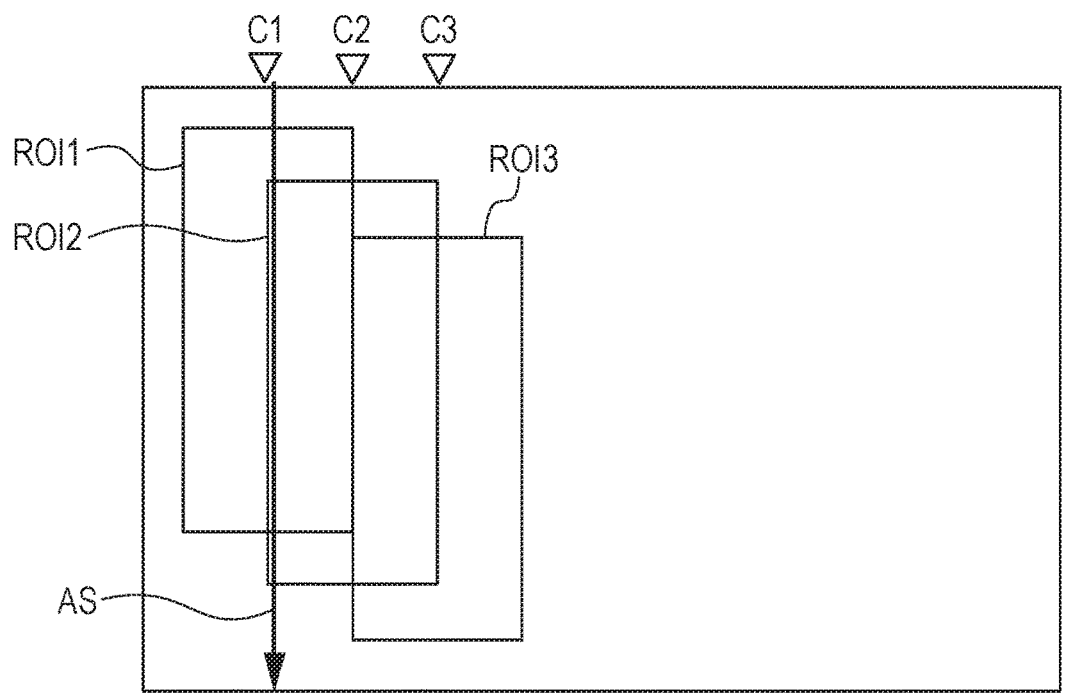
FIG. 27A and FIG. 27B describe the fourth alignment.
Figure 27B:
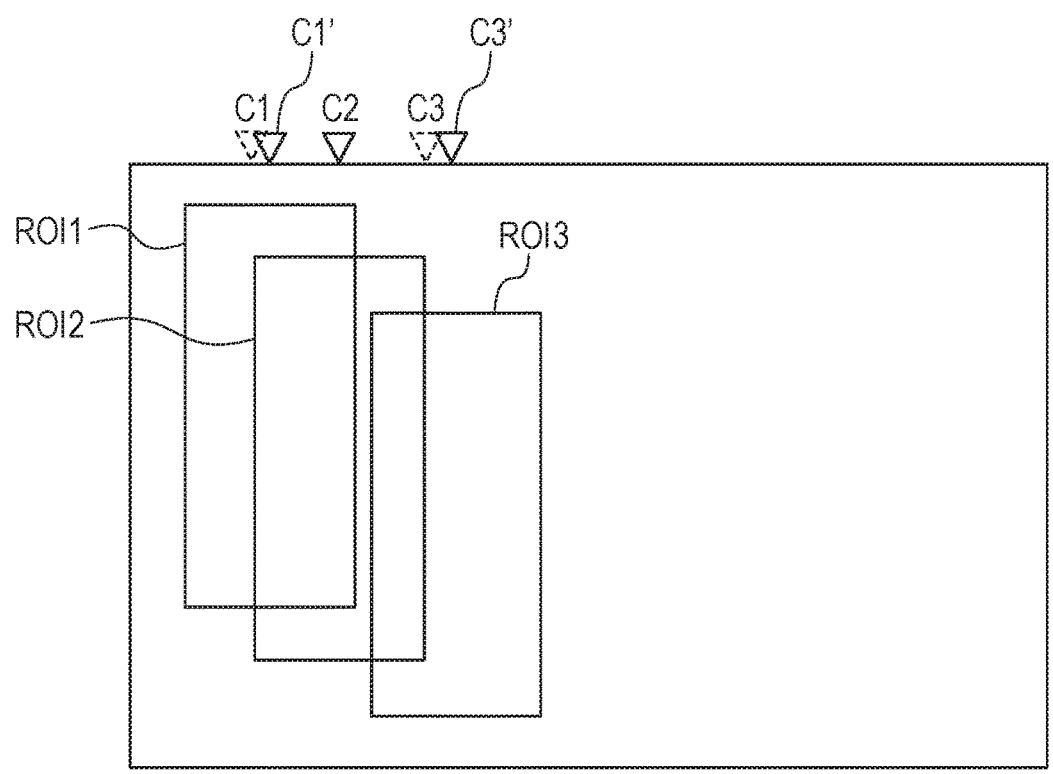

In step S15574, the fourth alignment unit 13338 interpolates the alignment parameters calculated in step S15573 to calculate movement amounts of the A scans. This is described with reference to FIGS. 27A and 27B. FIG. 27A illustrates an ROI 1 to an ROI 3 in an initially set region. Downward triangles C1 to C3 represent center positions of the ROI 1 to ROI 3. FIG. 27B illustrates a movement example of the ROIs after the alignment in step S3573. In FIG. 27B, an example is illustrated in which the ROI 1 and the ROI 3 respectively move to the right side and the ROI 2 does not move. Therefore, the centers C1 and C3 of the ROIs respectively move to C1' and C3'. In order to calculate movement amounts of the A scans from movement amounts of the ROIs, the movement amount of the A scans are calculated based on movement amounts of center positions of the ROIs adjacent to each other. For example, the center position of the ROI 1 moves from C1 to C1' and the center position of the ROI 2 remains in C2. Expressions for calculating X-direction movement amounts of the A scans present between C1 and C2 before deformation are illustrated in Expressions (14) to (16).

$$W = 1.0 - \frac{(A\_before - X1)}{(X2 - X1)} \quad (14)$$

$$TransX = \Delta X1 * W + \Delta X2 * (1.0 - W) \quad (15)$$

$$A\_after = A\_before - TransX \quad (16)$$

In Expressions (14) to (16), X1 and X2 indicate initial center coordinates of the ROIs, ΔX1 and ΔX2 indicate X-direction movement amounts of center coordinates of the ROIs, A_before indicates a value of an A scan index before deformation, and A_after indicates a value of the A scan index before deformation, which is to be referred to by A_before. For example, when A_before is set to 55 and A_after is set to 56 as a result of calculation, A scan data of the A scan index 56 is put in the A scan index 55. Note that, movement amounts in the Z direction can also be calculated from the movement amounts of the center positions of the ROIs based on the same idea as Expressions (14) to (16). Several pixel data are moved in the up-down direction. Note that a value of A_after may be either a real number or an integer. In the case of the real number, new A scan data is created by an interpolation method (Bilinear, Bicubic, etc.) from a plurality of A scan data. In the case of the integer, data of corresponding S scan index is referred to as it is. Note that an example is described above in which the local alignment is performed in both of the X direction and the Z direction. However, not only this, but, for example, local deformation may be performed only in one of the X direction and the Z direction. Note that, since the alignment is performed in the X direction by tracking during imaging, the local alignment may be performed only in the Z direction in order to reduce a processing load.

<Step S15575>

In step S15575, the fourth alignment unit 13338 moves each of the A scans in the X direction and the Z direction based on the A scan movement amount calculated in step S15574. Consequently, it is possible to generate a tomographic image deformed in a unit of the A scan. Note that, as the three-dimensional data to be deformed, both of the tomographic image data and the motion contrast data are deformed.

<Step S15576>

In step S15576, the fourth alignment unit 13338 determines whether the local alignment of all data set as targets of the alignment is performed for all tomographic images of the reference three-dimensional data. When not all of the data is processed, the fourth alignment unit 13338 return to step S15571. When the local alignment of all the data is performed, the processing of the local alignment ends.

The local alignment is performed by these kinds of processing. Description is made referring back to the processing flow of FIG. 15B.

<Step S1558>

In step S1558, the image combining unit 13339 performs averaging of the reference three-dimensional motion contrast data selected by the selection unit 13335 and the plurality of three-dimensional motion contrast data. In the averaging processing, a total value SUM_A of values obtained by multiplying values of the plurality of motion contrast data and a Mask image and a total amount SUM_B of values of a plurality of Mask images are respectively retained for each voxel. In the Mask image, an invalid region removed as an artifact and an invalid region where data is absent because of alignment are saved as 0. Therefore, a different value is retained in the total value SUM_B of the Mask images for each voxel. Usually, movement of several ten voxels is assumed for each of X, Y and Z in the alignment. Therefore, when the number of data used for superimposition is N, a voxel value of SUM_B near an image center is N. A voxel value of SUM_B at an image end is a value smaller than N. In the averaging processing, it is possible to calculate motion contrast data obtained by calculating a weighted average by dividing SUM_A by SUM_B.

Figure 28A:
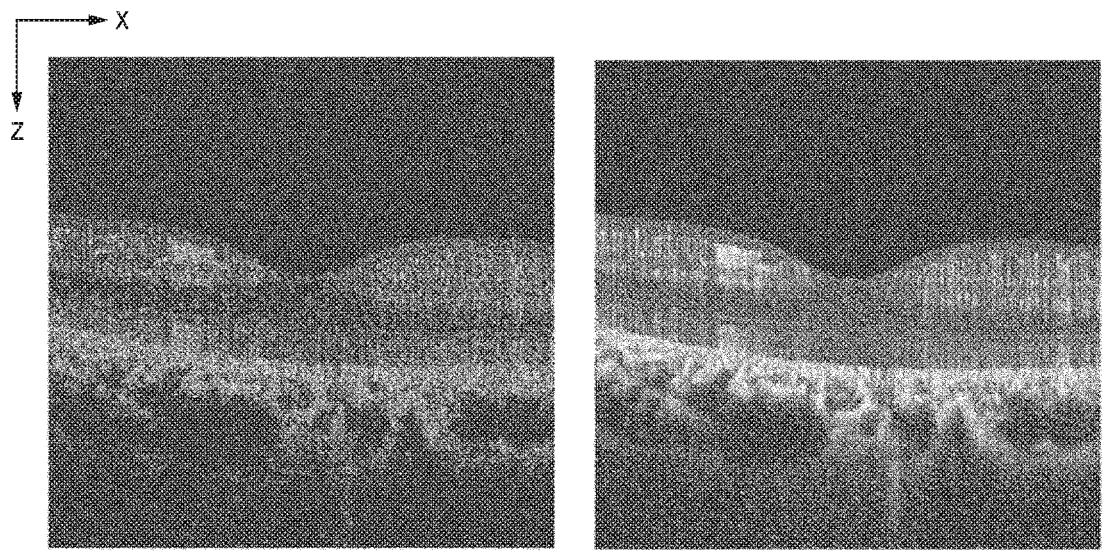
FIG. 28A and FIG. 28B describe before and after arithmetic averaging of motion contrast data and tomographic images.
Figure 28B:
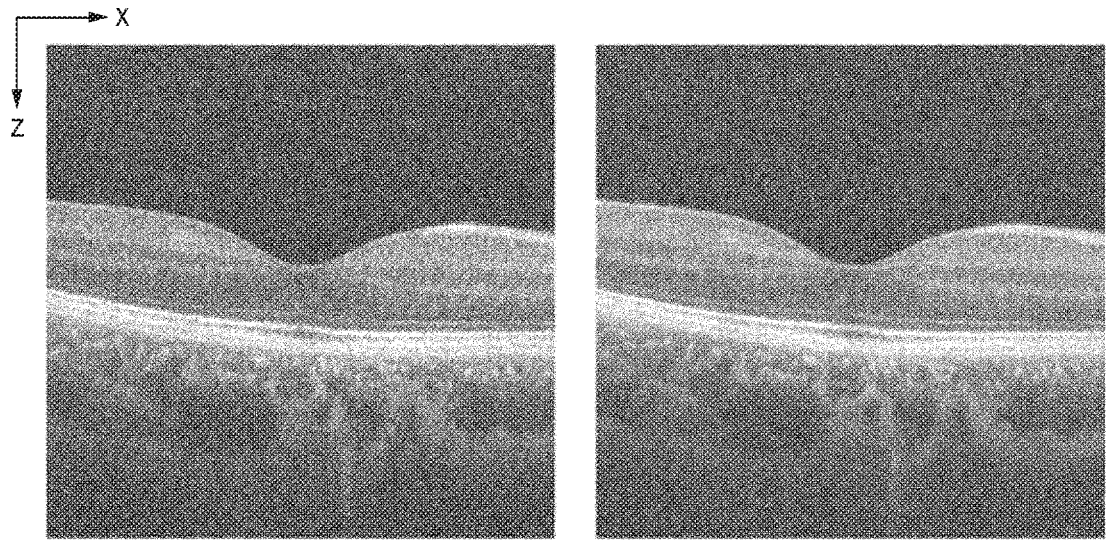
Figure 29A:
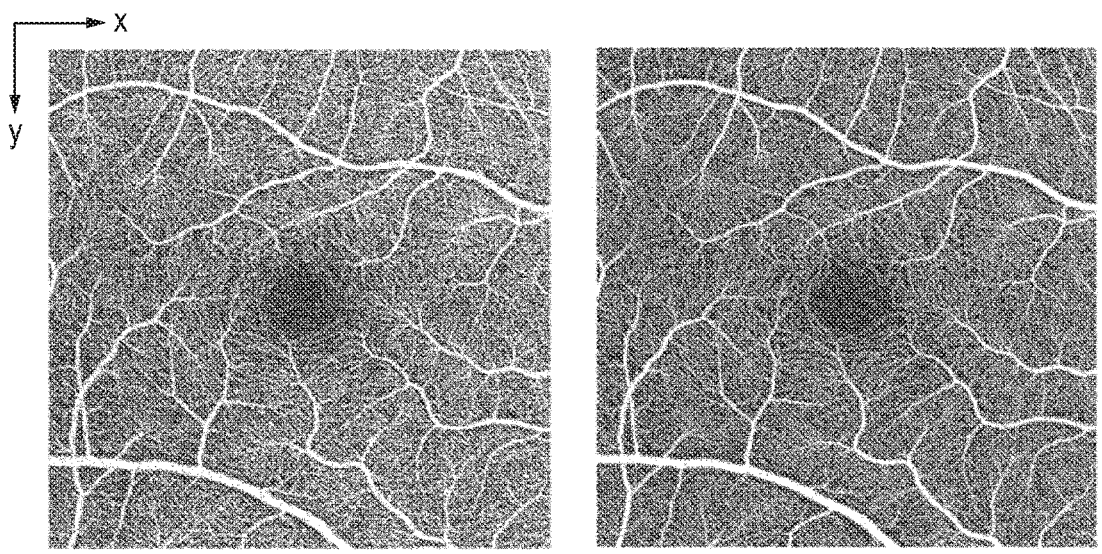
FIG. 29A and FIG. 29B describe before and after arithmetic averaging of motion contrast data and tomographic images.
Figure 29B:
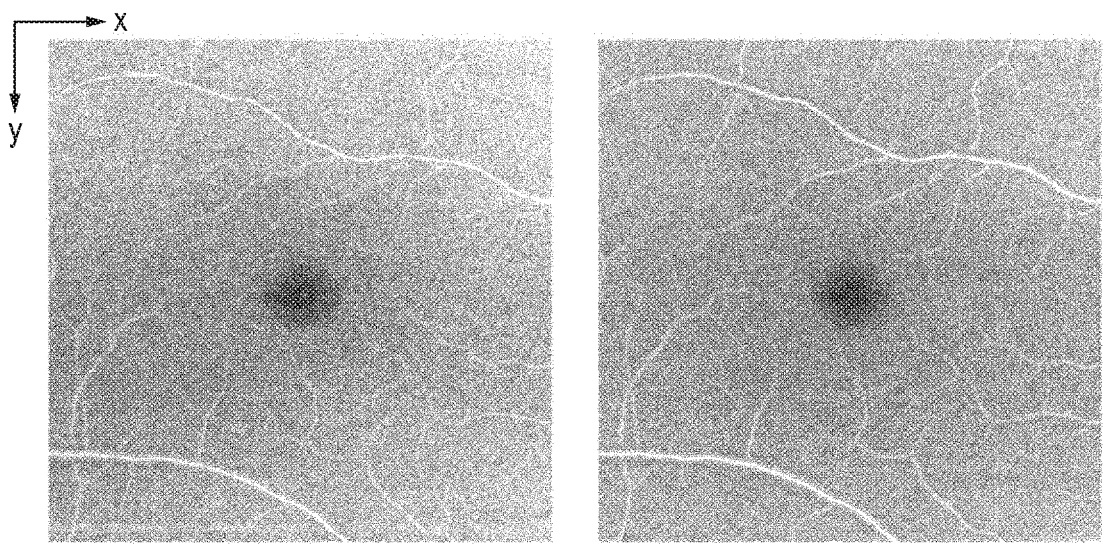
Figure 30A:
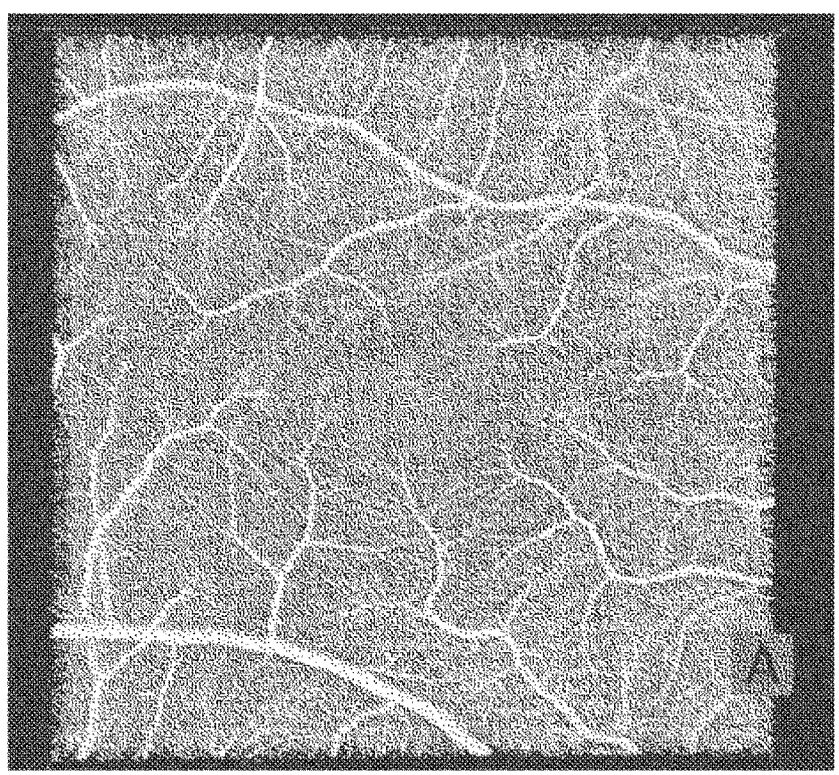
FIG. 30A and FIG. 30B describe before and after arithmetic averaging of motion contrast data.
Figure 30B:
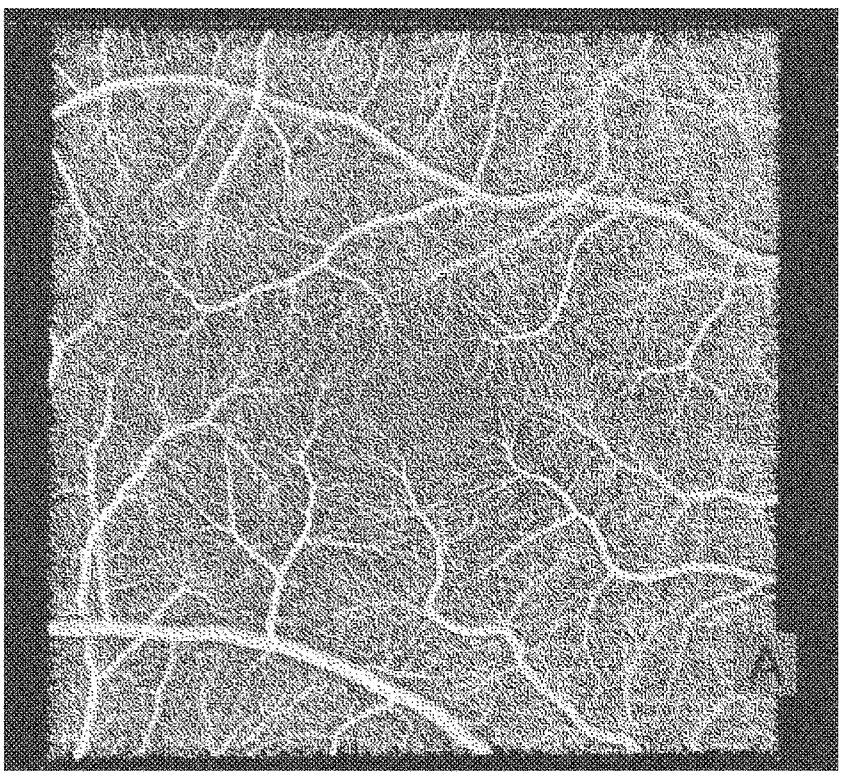

The motion contrast data before and after the averaging processing is performed are illustrated in FIG. 28A to FIG. 30B. FIGS. 28A and 28B illustrate an XZ plane, FIGS. 29A and 29B illustrate an XY plane, and FIGS. 30A and 30B illustrate an example in which the three-dimensional motion contrast data is subjected to volume rendering and displayed.

The left side of FIG. 28A illustrates one cross section of the three-dimensional motion contrast data before the averaging. The right side of FIG. 28A illustrates one cross section of the three-dimensional motion contrast data after the averaging. The left side of FIG. 29A illustrates an OCTA image of a retina surface layer generated from the three-dimensional motion contrast data before the averaging. The right side of FIG. 29A illustrates an OCTA image of the retina surface layer generated from the three-dimensional motion contrast data after the averaging. FIG. 30A illustrates an example of volume rendering data of the three-dimensional motion contrast data before the averaging. FIG. 30B illustrates an example of volume rendering data of the three-dimensional motion contrast data after the averaging. As illustrated in FIG. 28A to FIG. 30B, the three-dimensional motion contrast data with improved contrast can be obtained by the averaging processing. When the volume rendering of the motion contrast data is performed as illustrated in FIGS. 30A and 30B, it is easy to grasp a vertical positional relation in the depth direction of a blood vessel hardly recognized in a two-dimensional OCTA image.

In the same manner as for the three-dimensional motion contrast data, the averaging processing is performed concerning a plurality of three-dimensional tomographic image data. Note that cross sections of a three-dimensional tomographic image before and after the averaging processing in the same manner as for the motion contrast data are illustrated in FIG. 28B. The left side of FIG. 28B illustrates one cross section of the three-dimensional tomographic image before the averaging. The right side of FIG. 28B illustrates one cross section of the three-dimensional tomographic image after the averaging. As illustrated in FIG. 28B, the image before the averaging includes a lot of noise. A difference between a blood vessel and the noise and a boundary between layers are unclear. However, the image after the averaging includes less noise. The structures of the blood vessel and a retina layer can be recognized. In FIG. 29B, front images generated from the three-dimensional tomographic image are illustrated. The left side of FIG. 29B illustrates a front image generated from the three-dimensional tomographic image before the averaging. The right side of FIG. 29B illustrates a front image generated from the three-dimensional tomographic image after the averaging.

<Step S1559>

In step S1559, the third alignment unit 13337 resets, based on the three-dimensional motion contrast data and the three-dimensional tomographic image data of the input stored in step S15561 and the depth direction movement amounts of the A scans stored in step S15563, the retinal position of the reference data (in this embodiment, the Data 1) to the state of the depth position during the input of the retinal position. Specifically, the third alignment unit 13337 resets the three-dimensional motion contrast data and the three-dimensional tomographic image data after the averaging in step S1558 to the original states using the depth direction movement amounts of the A scans stored in step S15563. For example, when certain A scan is moved by five in the downward direction, the A scan is moved by five in the upward direction. When the A scan is further moved by five in the upward direction, an invalid region occurs in a data lower part. Therefore, data of the same coordinate position in the three-dimensional motion contrast data and the three-dimensional tomographic image data of the input stored in step S15561 are respectively copied to the invalid region.

Note that the example is described above in which the data of the input is copied to the invalid region of the data after the averaging. However, not only this, but data in a range corresponding to an original coordinate position may be cut out from the three-dimensional data after the averaging and copied to the three-dimensional data of the input stored by the third alignment unit 13337. Consequently, whereas the processing in the two steps of copying the data to the invalid region after the data movement is performed above, since only one step of the copying is performed, it is possible to reduce a processing load. Note that, in this case, since the data is copied to the three-dimensional data of the input stored in the third alignment unit 13337, final output data is the data stored in the third alignment unit 13337.

After these kinds of processing are performed, the processing returns to the flowchart of FIG. 15A.

<Step S1506>

In step S1506, high-quality three-dimensional motion contrast data and a high-quality three-dimensional tomographic image created by performing the averaging are displayed in an adaptable state.

Figure 31:
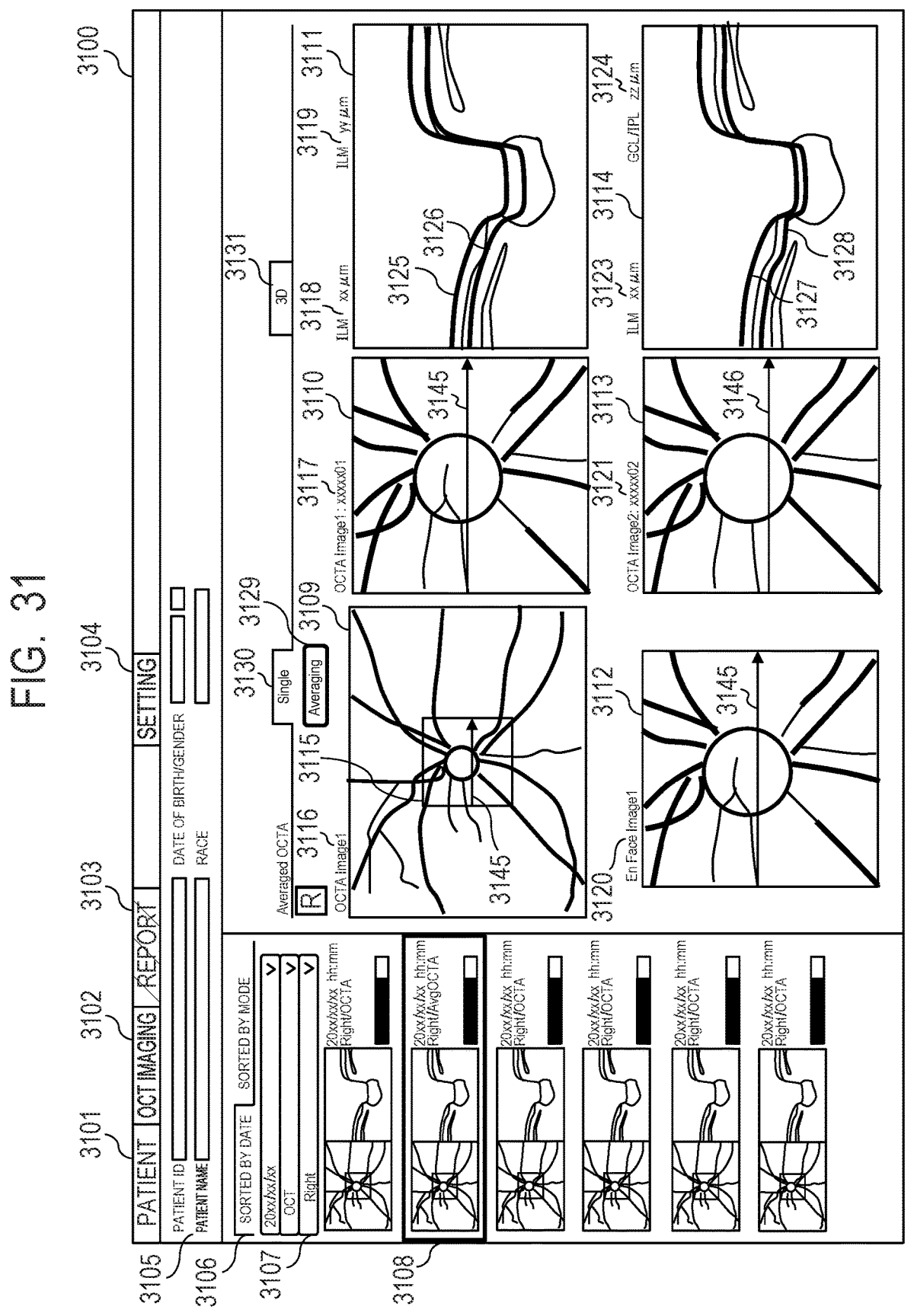

An example of a screen displayed on the display unit 1360 is illustrated in FIG. 31. In FIG. 31, an entire screen 3100, a patient tab 3101, an imaging tab 3102, a report tab 3103, and a setting tab 3104 are illustrated. Slant lines in the report tab 1303 represent an active state of a report screen. In this embodiment, an example is described in which the report screen is displayed. In FIG. 31, a patient-information display portion 3105, an examination sort tab 3106, and an examination list 3107 are illustrated. A black frame 3108 represents selection of the examination list. Selected examination data is displayed on the screen. Thumbnails of an SLO and a tomographic image are displayed in the examination list 3107 illustrated in FIG. 31. However, in the case of OCTA imaging, although not illustrated in the figure, a thumbnail of an OCTA may be displayed. As an example of the thumbnail display, the thumbnails of the SLO and the OCTA, only the thumbnail of the OCTA, and the thumbnails of the tomographic image and the OCTA may be displayed. In this embodiment, examination data acquired by imaging and examination data generated by image quality improving processing are displayed in the examination list 3107 as a list. In the examination data generated by the image quality improving processing, an image generated from data subjected to the image quality improving processing may be displayed as an image displayed as a thumbnail.

FIG. 31 further illustrates tabs 3130 and 3131 of a view mode. In the tab 3130, a two-dimensional OCTA image generated from the three-dimensional motion contrast data is displayed. In the tab 3131, the three-dimensional motion contrast data illustrated in FIG. 30B is displayed.

A button 3129 for executing high-quality generation of a motion contrast is illustrated. Note that, in this embodiment, the operator presses the button 3129 for executing the high-quality generation to execute the high-quality data generation processing illustrated in step S1505. The operator presses this button in order to display data candidates used for image quality improvement. Note that, when data repeatedly imaged under the same imaging conditions as the selected data is automatically selected, the high-quality data generation may be executed without displaying data candidates. It is possible to select the generated high-quality data as report display by displaying the generated high-quality data in the examination list 3107. Note that, in this embodiment, the image quality improving processing has already been completed. In FIG. 31, the data subjected to the image quality improving processing is selected and displayed. Therefore, in the following description, the data subjected to the image quality improving processing (the averaging) is described. Note that, in FIG. 31, an example is illustrated in which imaging of an optic disc and data of the optic disc is displayed. The example in the optic disc is described in this embodiment. However, not only this, but a part to be imaged may be a yellow spot or a viewing angle in the imaging may be a wide viewing angle rather than a narrow viewing angle.

FIG. 31 further illustrates an SLO image 3109, a first OCTA image 3110, a first tomographic image 3111, a front image 3112 (an en face image) generated from a three-dimensional tomographic image, a second OCTA image 3113, and a second tomographic image 3114. FIG. 31 illustrates a tab 3120 for switching a type of the image 3112. The en face image 3112 shows an en face created from the same depth range as the first OCTA. However, the en face image 3112 can also be switched to, by the tab 3120, an en face created from the same depth range as the second OCTA. Note that, in this embodiment, as the images 3110 to 3114, images subjected to the averaging processing are displayed as illustrated in FIG. 28A to FIG. 29B. FIG. 31 further illustrates an image 3115 superimposed on the SLO image 3109 and a tab 3116 for switching a type of the image 3115. FIG. 31 illustrates a tab 3117 for switching a type of an OCTA image displayed as the first OCTA image and a tab 3121 for switching a type of an OCTA image displayed as the second OCTA image. Types of the OCTA include OCTA images created in a shallow layer, a deep layer, a choroid, and the like and in any range. Note that, concerning an upper end (3118 and 3125) and a lower end (3119 and 3126), which are creation ranges of the first OCTA image 3110, display 3118 represents a type of a boundary line at the upper end, which is an example of a reference line, and an offset value of the boundary line. The boundary line 3125 at the upper end is superimposed and displayed on a tomographic image. Display 3119 represents a type of a boundary line at the lower end, which is an example of a reference line, and an offset value of the boundary line. A boundary line 3126 at the lower end is superimposed and displayed on the first tomographic image. In the second OCTA image, as in the first OCTA image, an upper end (3123 and 3127) and a lower end (3124 and 3128) are superimposed and displayed on the second tomographic image. Note that the first OCTA image 3110 and the en face image 3112 are examples of an image created from a depth range of a radial peripapillary capillaris (RPC). The second OCTA image 3113 is an example of an image created from a depth range of the shallow layer of the retina. For example, one reference line may be set rather than the two boundary lines. In this case, two offset values on the upper side and the lower side may be set with respect to one reference line. At least one of the reference line and the offset value with respect to the reference line may be set.

An arrow 3145 indicates a position in the XY plane of the first tomographic image. An arrow 3146 indicates a position in the XY plane of the second tomographic image. It is possible to switch the positions in the XY plane of the first tomographic image 3111 and the second tomographic image 3114 by operating the arrows 3145 and 3146 with mouse drag or the like.

Figure 32A:
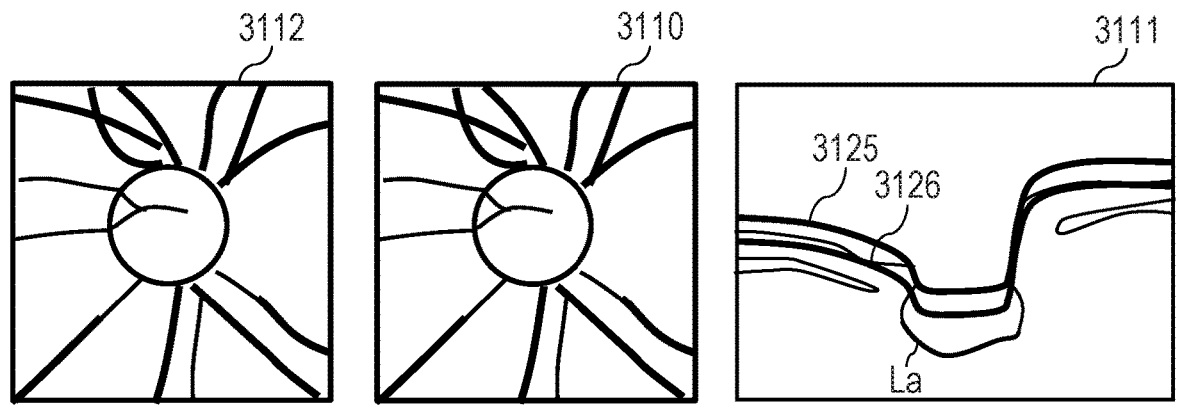
FIG. 32A and FIG. 32B describe two-dimensional front images.
Figure 32B:
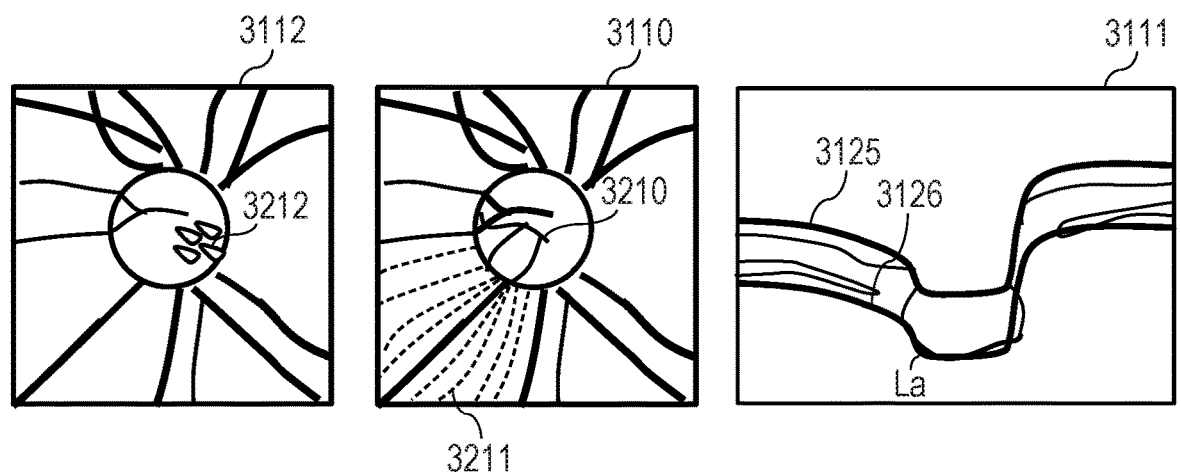

Generating one two-dimensional front image (en face image or OCTA image) using three-dimensional data in different depth ranges set with respect to a plurality of regions in a direction crossing the depth direction of an eye to be inspected in this embodiment is described with reference to FIG. 32A to FIG. 34. FIG. 32A illustrates an upper boundary line 3125 and a lower boundary line 3126, which are creation ranges of the en face image 3112, the first OCTA image 3110, the first tomographic image 3111, and the first OCTA image 3110 in FIG. 31. FIG. 32A illustrates an example of an OCTA image created in the depth range of the radial peripapillary capillaris. For example, the upper boundary line 3125 is set to an inner boundary membrane (ILM) and the lower boundary line 3126 is set to the inner boundary membrane (ILM)+an offset value (several ten micrometers). FIG. 32B illustrates an example in the case in which the entire boundary line 3126 is moved in the depth direction to include an entire lamina cribrosa. The boundary line 3126 is set to the inner boundary membrane (ILM)+an offset value (several hundred micrometers). As illustrated in FIG. 32B, in the en face image 3112, a lamina pore 3212 is observed. In the OCTA image 3110, the optic disc inside and a blood vessel 3210 inside the lamina cribrosa are observed. Since a depth region for observing the radial peripapillary capillaris is changed to a depth region including the entire lamina cribrosa in this way, it is easy to observe the blood vessel and the lamina pore on the optic disc inside. On the other hand, in the optic disc periphery, since a range from a nerve fiber layer to the RPE and the choroid is included, contrast of the entire en face image 3112 decreases. A blood vessel of a deep layer section, which is not a shallow layer section, is observed in the OCTA image as an artifact (a broken line 3211 in FIG. 32B).

Figure 33A:
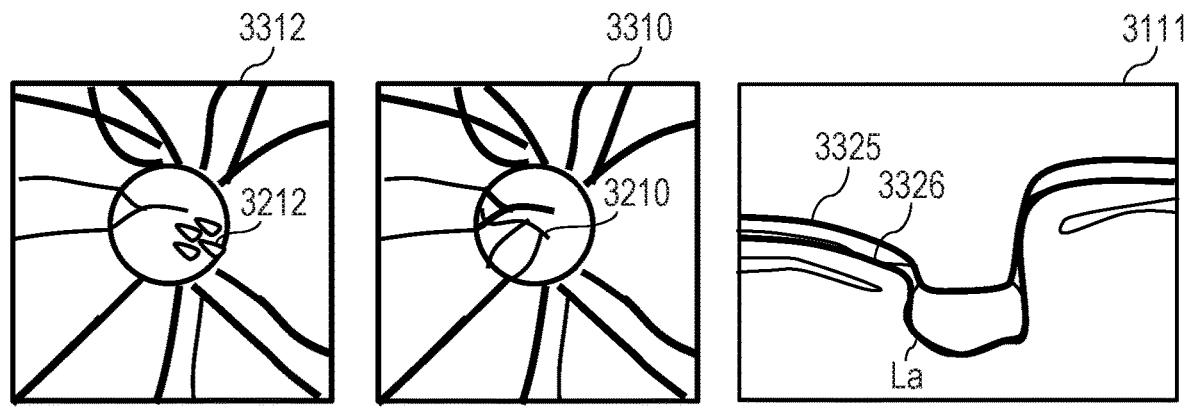
FIG. 33A and FIG. 33B describe two-dimensional front images generated from different depth ranges set in a plurality of regions in a direction that intersects the depth direction.

Therefore, in this embodiment, as illustrated in FIG. 33A, an en face image 3312 and an OCTA image 3310 in different depth ranges set with respect to a plurality of regions in the direction crossing the depth direction are created. The setting of the different depth ranges means, for example, setting a boundary line 3326 to be a depth range of the radial peripapillary capillaris in the optic disc periphery and setting the boundary line 3326 to be a depth range including the lamina cribrosa on the optic disc inside. That is, when the two-dimensional front image (the en face or OCTA image) is generated, an image is generated based on not only one reference (one of the boundary line and the offset value) but also different references (the boundary line and the offset value). By generating such an image, even if an image includes regions respectively having different depth ranges of attention, it is possible to generate a two-dimensional front image created in an appropriate range. Consequently, in the en face image 3312, the lamina pore 3212 is observed and, at the same time, contrast of the entire image is kept. In the OCTA image 3310, the blood vessel on the optic disc inside can be observed and, at the same time, the radial peripapillary capillaris can be observed in the optic disc periphery.

Figure 33B:
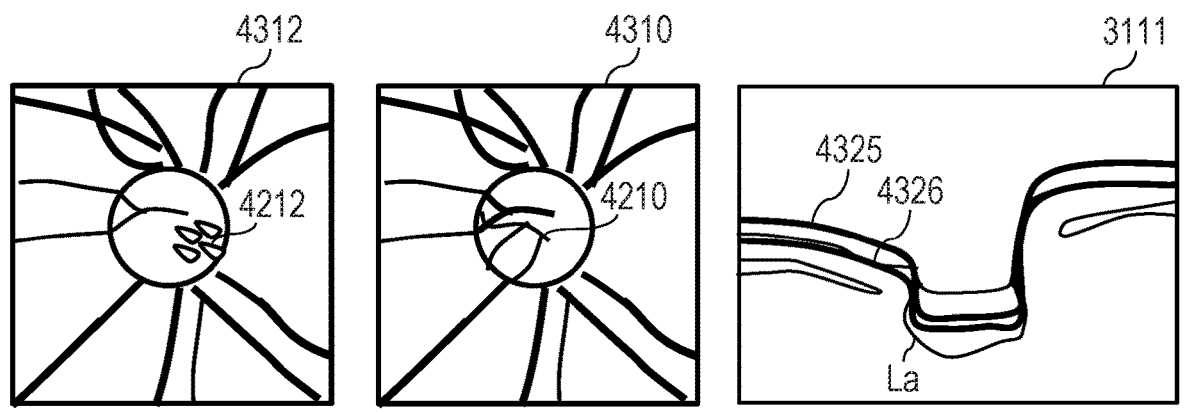
Figure 34:
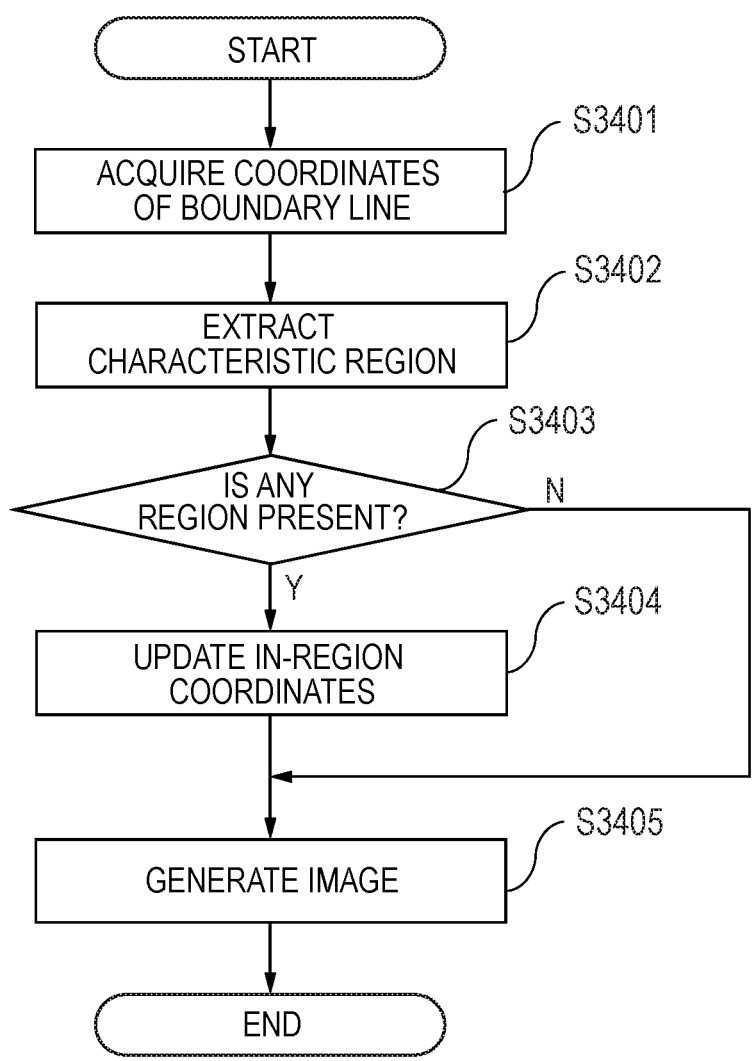
FIG. 34 is a flowchart illustrating the flow of two-dimensional front image generation.

Note that setting of the depth range is not limited to the setting illustrated in FIG. 33A. As illustrated in FIG. 33B, a boundary line 4325 and a boundary line 4326 may respectively cut out the vicinity of the center of the lamina cribrosa. Consequently, a lamina pore 4212 located at specific depth in an en face image 4312 can be observed. In an OCTA image 4310, the structure of a blood vessel 4210 located at specific depth of the optic disc inside can be observed. The depth range in the optic disc periphery may be set to a depth range of the retina shallow layer rather than the depth range of the radial peripapillary capillaris.

The settings of the layer ranges illustrated in FIGS. 32A and 32B can be switched and displayed. For example, the settings of the layer ranges can be switched and displayed by tabs 3117 and 3121 for switching a type of an image displayed as the OCTA image displayed on the screen illustrated in FIG. 31. In the en face image, similarly, display can be switched by a tab 3120 for switching a type of an image. Images may be displayed side by side on the screen illustrated in FIG. 31 rather than only being switched and displayed.

In order to represent the different depth ranges described above in one two-dimensional front image, it is necessary to extract a target region. Therefore, a generation method for a two-dimensional front image (an OCTA image or an en face image) in this embodiment is described with reference to a flowchart of FIG. 34.

<Step S3401>

In step S3401, the image generation unit 13332, which is an example of a depth range setting unit, acquires upper and lower boundary lines and an offset value in order to generate an OCTA image and an en face image. The coordinate data detected in step S1551 is used as the boundary lines. Alternatively, the boundary lines may be detected by the same method as the method illustrated in step S1551 in the three-dimensional tomographic image after the image quality improving processing is performed. An initial value in the depth direction is set for each type of a two-dimensional front image to be generated. The initial value is used as the offset value. For example, when a two-dimensional front image in the range of the RPC is generated, the upper boundary line is set to the ILM boundary line and the lower boundary line is set to the ILM boundary line+the offset value.

<Step S3402>

In step S3402, the region extraction unit 13340 extracts (specifies or detects) at least one region (partial region) for setting a depth range different from depth ranges of the other regions among a plurality of regions in the direction crossing the depth range of the eye to be inspected. In this embodiment, an example is described in which the optic disc and the lamina cribrosa region are detected. First, the region extraction unit 13340 detects a BMO (Bruch's membrane opening), which is an example of a characteristic part concerning the optic disc in the tomographic images illustrated in FIG. 33A or FIG. 33B. In the detection of the BMO, the optic disc is specified using, for example, results of the ILM and the RPE detected in step S1551. Note that types of boundary lines are not limited to the ILM and the RPE and may be an NFL/GCL boundary and an IS/OS. In this case, in particular, it is possible to specify a recessed part of the optic disc. In this embodiment, the vicinity of the center of the recessed part of the optic disc is specified. As characteristics of the recessed part of the optic disc, the RPE is absent and the shape of the ILM has a large gradient in the depth direction (the Z direction in FIGS. 33A and 33B). Therefore, a local region including A-scans and peripheral A-scans of the A-scans is set. A presence state of the RPE and a gradient of the shape in the depth direction of the ILM in the local region are calculated to specify a point near the center of the recessed part of the optic disc. Subsequently, points of RPEs close to the vicinity of the center of the recessed part of the optic disc in the tomographic images are connected in all the tomographic images to set an RPE region having an elliptical shape when viewed in a C-scan direction. The RPE region is set as an initial position. A proper dynamic contour model (e.g., Snakes) is applied to specify BMOs in the tomographic images. Subsequently, edge components are traced toward the center of the recessed part of the optic disc from the end portions specified earlier, that is, BMO ends to specify accurate positions of the BMO ends. In this embodiment, first, coordinate values and edge components are checked concerning the BMO ends. Subsequently, edges are traced toward the center of the recessed part of the optic disc starting from the positions of the BMO ends. In the tracing, with reference to the edge components in the position of the BMO ends, a search point is updated to a position where an edge component present in the vicinity on the inner side is the closest. The edge components to be referred to are also updated. Accurate BMO ends are specified by repeating this processing. The region extraction unit 13340, which is an example of a region setting unit, specifies, based on the detected BMOs, the recessed part of the optic disc. Consequently, for example, the region setting unit can set a partial region using information concerning the detected optic disc (e.g., a coordinate value in the X direction and a coordinate value in the Y direction).

Lamina cribrosa detection is described. A luminance gradient is detected in the depth direction based on an ILM. The rear surface of the lamina cribrosa changes from a bright region to a dark region toward the depth in a tomographic image. Therefore, a characteristic of a change in luminance is extracted to detect the lamina cribrosa rear surface. Note that, when the lamina cribrosa rear surface is detected, since the thickness of the lamina cribrosa is approximately several hundred micrometers, a range to be detected may be specified using knowledge concerning the thickness. Consequently, for example, a depth range setting unit can specify a depth range of the partial region using information concerning the detected lamina cribrosa region (e.g., a coordinate value in the Z direction).

Note that the detection of the optic disc and the lamina cribrosa is not limited to the example described above. For the detection of the optic disc, a region may be detected using a two-dimensional image viewed in the C-scan direction such as an SLO image or an en face rather than the tomographic image. The optic disc viewed in the C-scan direction has an elliptical shape. Therefore, for example, an elliptical region in an image can be specified by performing noise removal and edge detection on the two-dimensional image and performing Huff transform on an edge image. Further, a rough position of the optic disc may be specified using information concerning a fixation lamp during imaging. Further, a publicly-known image detecting method may be used. The methods described above can also be used in combination.

<Step S3403>

In step S3403, the flow is changed according to whether the region extraction unit 13340 extracts a region. When a region is extracted in step S3403, the processing is advanced to step S3404. When a region is not extracted, the processing is advanced to step S3405.

<Step S3404>

In step S3404, the image generation unit 13332, which is an example of a depth-range setting unit, updates the boundary line coordinate acquired in step S3401 using information concerning the region extracted by the region extraction unit 13340. For example, the Z coordinate of the lower boundary line is the ILM boundary line+the offset value. However, in the recessed part of the optic disc, the Z coordinate is updated to a Z coordinate of the lamina cribrosa rear surface. That is, a setting unit for depth ranges can change a set depth range of at least one region from an initial value set in a state in which depth ranges of the other regions are fixed. Consequently, for example, the operator such as the doctor can easily perform the change of the depth ranges of the regions. Note that the setting unit for depth ranges may set the set depth range of the at least one region and the depth ranges of the other regions independently from each other.

<Step S3405>

In step S3405, an OCTA image and an en face image are generated based on the Z coordinates of the upper and lower boundary lines. The OCTA image is generated from three-dimensional motion contrast data. The en face image is generated from three-dimensional tomographic image data. An image generating method sets, in Ascans, as a representative value of the Ascans, a statistical value such as an average, a maximum, or a median of data in a Z coordinate range of the upper and lower boundary lines or a maximum of averages in a plurality of divided regions in the Z coordinate range. The calculated representative value of the Ascans is equivalent to a pixel value of a two-dimensional front image.

Note that this embodiment is described with reference to the example of the optic disc. Therefore, the two-dimensional front image is generated from the depth ranges described above. However, not only this, but the two-dimensional front image may be generated from any range if the two-dimensional front image is created in depth ranges different from each other in the partial region and the other regions. Further, the partial region is not always limited to one. A plurality of partial regions may be extracted.

<Step S1507>

In step S1507, a not-illustrated instruction acquisition unit acquires, from the outside, an instruction concerning whether to end the imaging or the analysis of the tomographic image by the image processing system 1300. The instruction is input by the operator using the input unit 1370. When acquiring an instruction to end the processing, the image processing system 1300 ends the processing. On the other hand, when continuing the imaging or the analysis without ending the processing, the image processing system 1300 returns the processing to step S1502 and continues the processing. The processing of the image processing system 1300 is performed as described above.

With the configuration described above, in this embodiment, by generating the two-dimensional front image using the three-dimensional data in the different depth ranges, it is possible to generate one two-dimensional front image generated from a plurality of different desired ranges. Consequently, it is possible to simultaneously confirm, in the one two-dimensional front image, the radial peripapillary capillaris, the blood vessel in the optic disc, and the lamina cribrosa.

Fifth Embodiment: Set Different Depth Ranges for an OCTA Image and an en Face Image In the fourth embodiment, the example is described in which the OCTA image and the en face image are generated using the three-dimensional data in the different depth ranges set for the plurality of regions in the direction crossing the depth direction of the eye to be inspected. In the example, the depth ranges set for the OCTA image and the en face image are common to each other. In a fifth embodiment, an example is described in which different depth ranges are set for the OCTA image and the en face image. Note that description is omitted concerning units having the same function as the functions in the first embodiment. Generation of the OCTA image and the en face image in this embodiment is described with reference to FIG. 35.

Figure 35:
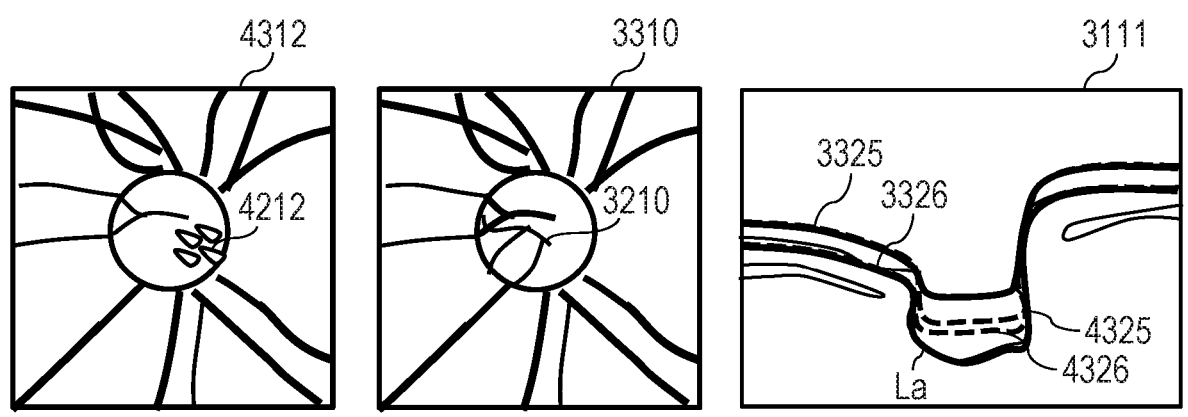
FIG. 35 describes two-dimensional front images generated from different depth ranges set in a plurality of regions in a direction that intersects the depth direction.

In FIG. 35, the OCTA image 3310 is created from a depth range of the radial peripapillary capillaris in the optic disc periphery and from ranges of boundary lines 3325 and 3326 (in FIG. 35, thick solid lines), which are depth ranges including the lamina cribrosa on the optic disc inside. On the other hand, the en face image 4312 is created from the depth range of the radial peripapillary capillaris in the optic disc periphery and from ranges of boundary lines 4325 and 4326 (in FIG. 35, thick broken lines) for cutting out the vicinity of the center of the lamina cribrosa on the optic disc inside. With these different depth ranges, it is possible to fully display a blood vessel in the OCTA image 3310. It is possible to display the lamina cribrosa at high contrast in the en face image 4312. In FIG. 35, the boundary lines 3325 and 3326 superimposed and displayed on the tomographic image 3111 are illustrated as the solid lines and the boundary lines 4325 and 4326 are illustrated as the broken lines. However, not only this, but the boundary lines 3325 and 3326 and the boundary lines 4325 and 4326 may be displayed by changing colors and transparency of the lines rather than the types of the lines. On and Off of a function for superimposing and displaying boundary lines on a tomographic image may be switched using a not-illustrated checkbox.

Note that the setting of the depth ranges is not limited to the setting described above. Other depth ranges may be set. The en face image may be generated from the range of the boundary lines 3325 and 3326 described above. The OCTA image may be generated from the range of the boundary lines 4325 and 4326.

With the configuration described above, in this embodiment, different depth ranges of two-dimensional front image of different types (e.g., a motion contrast front image and a luminance front image) can be set. Consequently, for example, by observing one two-dimensional front image for one type, it is possible to simultaneously confirm the radial peripapillary capillaris, the bool vessel in the optic disc, and the lamina cribrosa. Note that the setting unit that sets depth ranges can include at least one function of a function of setting a common depth range for two-dimensional front images of different types (e.g., a motion contrast front image and a luminance front image) and a function of setting different depth ranges. When the setting unit includes both the functions, the setting unit can be configured to be capable of selecting one of both the functions. Consequently, the operator can easily select one of the functions according to a purpose.

Sixth Embodiment: At Least One Region in the Direction Crossing the Depth Region is Set and Changed According to an Instruction of the Operator In the fourth and fifth embodiments, the example is described in which the two-dimensional front image is generated from the different depth ranges respectively on the inside and the outside of the partial region (at least one region in the direction crossing the depth direction) automatically extracted by the region extraction unit 13340. In a sixth embodiment, an example is described in which a partial region extracted by the region extraction unit 13340 is corrected (changed) according to an instruction of the operator or the region extraction unit 13340 does not extract a partial region and a partial region is added anew according to an instruction of the operator.

Figure 36A:
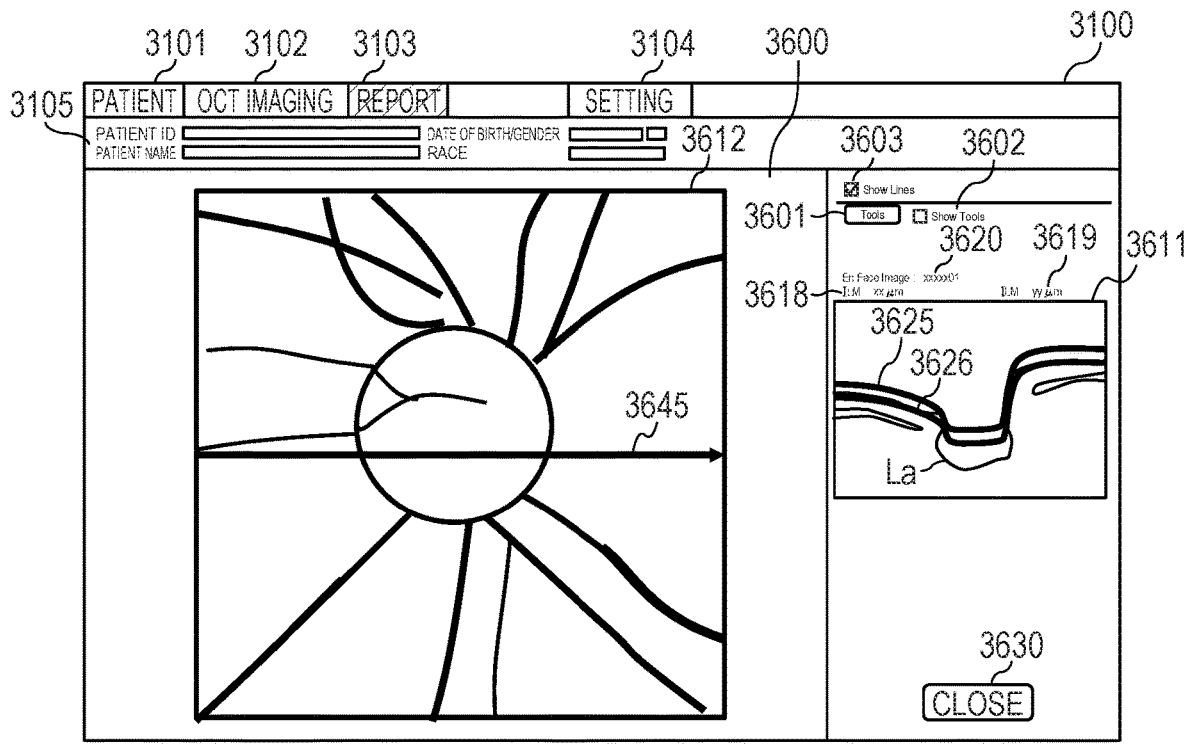
FIG. 36A and FIG. 36B describe an editing screen.

Description is omitted concerning units having the same function as the functions in the first and second embodiments. A method of correcting a partial region in this embodiment is described with reference to FIGS. 36A and 36B. FIG. 36A illustrates an example of an editing screen 3600 for an en face image 3612 displayed by double clicking of an en face image on the screen illustrated in FIG. 31. The operator displays a Tools dialog 3604 by clicking a Tools button 3601 on the editing screen 3600. An editing function using the Tools dialog 3604 is described below with reference to FIG. 36B. With a Show Tools checkbox 3602, On/Off of function display set by the editing function of the Tools dialog 3604 can be switched. With a Show Lines checkbox 3603, On/Off of display of an arrow 3645 indicating a position on the XY plane of a tomographic image 3611 is switched. In the tomographic image 3611, a type of an upper boundary line, which is a creation range of an en face image, and an offset value 3618 of the upper boundary line and a type of a lower boundary line and an offset value 3619 of the lower boundary line are illustrated. An upper boundary line 3625 and a lower boundary line 3626 are superimposed and displayed. A name of a depth range in which the en face image 3612 is generated is displayed in 3620. For example, RPC, Custom, or the like is displayed in the name 3620.

Figure 36B:
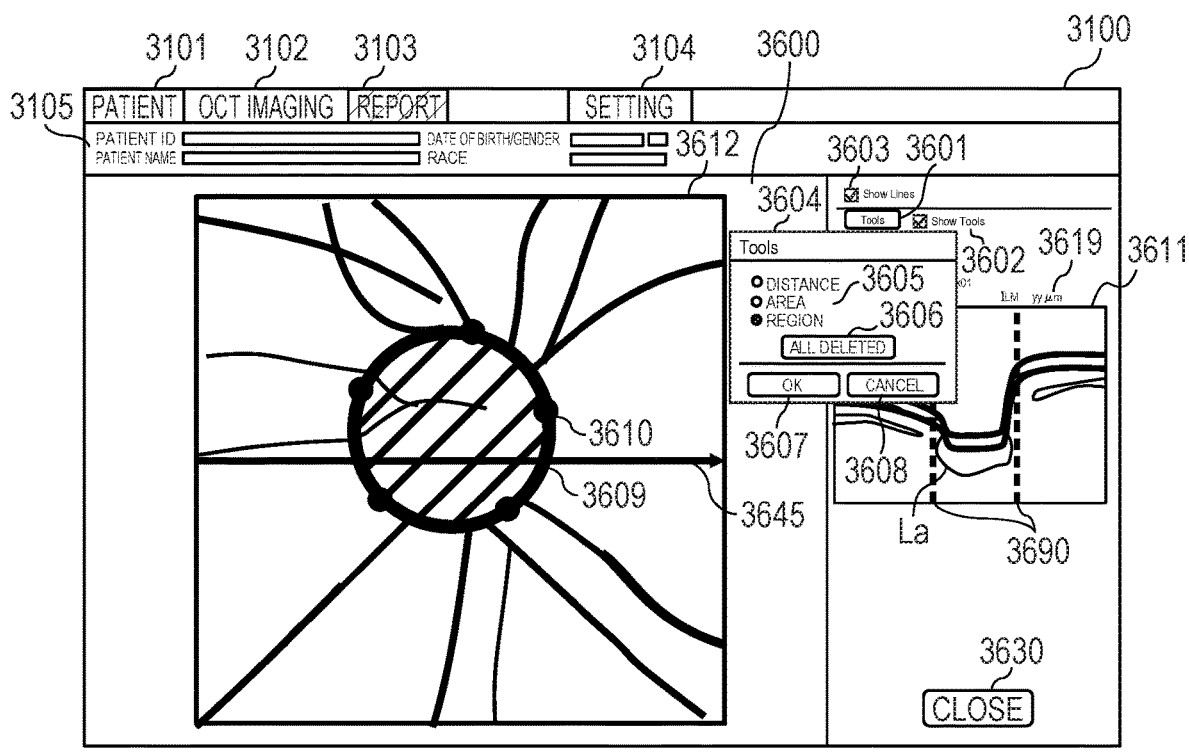

An editing method for a partial region performed on the en face image 3612 is described with reference to FIG. 36B. A type 3605 of a function for performing editing is displayed in the Tools dialog 3604. A distance, an area, and a partial region are illustrated as examples of the editing function. However, in the following description in this embodiment, the partial region is edited. Note that it is assumed that the region extraction unit 13340 has already extracted the partial region. When the partial region is edited, a partial region 3609 (in FIG. 36B, a circular hatched portion) and a control point 3610 for editing are superimposed and displayed on the en face image 3612. That is, the display control unit 1335 can cause the display unit 1360 to display information indicating the partial region (e.g., a line indicating the outer edge of the partial region and a color superimposed in the partial region) in a state in which the information is superimposed on a two-dimensional front image generated using an initial value, a value changed from the initial value, or the like as a depth range. Consequently, for example, the operator such as the doctor can easily confirm the partial region in the two-dimensional front image. On the tomographic image 3611, a part equivalent to a crossing part of the arrow 3645 and the partial region 3609 is displayed as a dotted line 3690. With the dotted line 3690, it is possible to grasp which part of the tomographic image 3611 the partial region 3609 is equivalent. That is, the display control unit 1335 can cause the display unit 1360 to display the information indicating the partial region (e.g., the line indicating the outer edge of the partial region or the color superimposed in the partial region) in a state in which the information is superimposed on the tomographic image 3611 of the eye to be inspected. Consequently, for example, the operator such as the doctor can easily confirm the partial region in the tomographic image. Note that the dotted line 3690 may be hidden when one of the Show Tools checkbox 3602 and the Show Lines checkbox 3603 is unchecked.

When editing the partial region 3609, the operator can edit the partial region 3609 by dragging the control point 3610. That is, the display control unit 1335 can cause the display unit 1360 to display information indicating the partial region in a state in which a position of the information in an image is updated according to an instruction of the operator. Consequently, for example, the operator such as the doctor can easily change the position of the partial region. Note that the shape of the partial region 3609 changes on the XY plane according to the drag of the control point. However, the position of the crossing part with the arrow 3645 also changes according to the change of the shape. Therefore, the position of the dotted line 3690 also moves in the X direction according to the change of the position of the crossing part. When the editing of the partial region 3609 is completed, the operator clicks an OK button 3607 to close the Tools dialog 3604. When the OK button 3607 is clicked, editing information is stored in the storage unit 1332. On the other hand, when a cancel button 3608 is clicked to close the Tools dialog 3604, the editing information is not stored.

When an all-delete button 3606 is clicked, it is possible to delete the partial region 3609 and continue the editing function. Therefore, the partial region 3609 is deleted when the OK button 3607 is clicked in that state. When the cancel button 3608 is clicked, the deletion of the region 3609 is cancelled and the partial region 3609 is retained.

The example in which the partial region 3609 already extracted by the region extraction unit 13340 is edited is described. However, not only this, but, for example, any partial region may be added anew or a plurality of regions may be added other than the partial region 3609. Concerning the editing method of the partial region 3609, the example in which the partial region 3609 is edited by the control point 3610 is described. However, not only this, but, for example, the dotted line 3690 superimposed and displayed on a tomographic image may be operated to deform the shape of the partial region 3609. Consequently, since the partial region 3609 can be edited in a unit of a Y cross section, finer editing of the partial region can be performed.

When the editing is completed, the operator clicks a close button 3630 and returns to the display of the report screen (e.g., FIG. 31).

With the configuration described above, in this embodiment, the operator can perform editing and addition of a partial region for generating a two-dimensional front image using the three-dimensional data in the different depth ranges. Consequently, it is possible to perform accurate setting of a partial region and perform setting of any partial region.

Seventh Embodiment: A Depth Range is Changed According to an Instruction of the Operator for Each Region in the Direction Crossing the Depth Direction In the fourth to sixth embodiments, the example is described in which the two-dimensional front image is generated using the three-dimensional data in the different depth ranges set for the plurality of regions in the direction crossing the depth direction of the eye to be inspected. In a seventh embodiment, an example is described in which a depth range of a generated two-dimensional front image is changed (corrected) for each portion.

Description is omitted concerning sections having the same functions as the functions in the first to third embodiments. A method of changing a depth range for each portion in this embodiment is described with reference to FIGS. 37A to 37C.

Figure 37A:
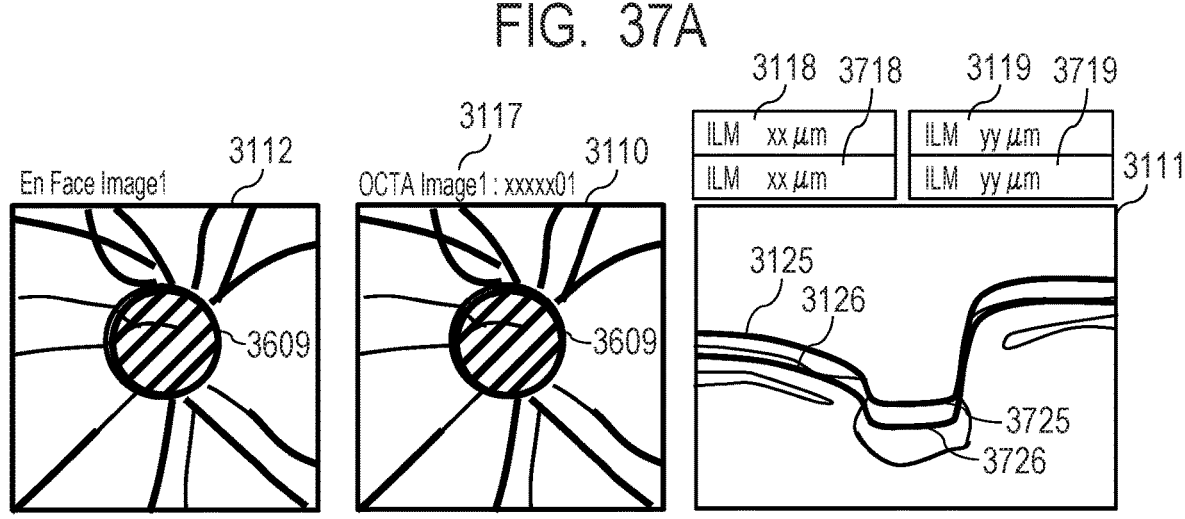
FIG. 37A, FIG. 37B, and FIG. 37C describe two-dimensional front images generated from different depth ranges set in a plurality of regions in a direction that intersects the depth direction.

FIG. 37A illustrates the en face image 3112, the first OCTA image 3110, and the first tomographic image 3111 and the boundary line between the upper end (3118 and 3125) and the lower end (3119 and 3126), which are the creation ranges of the first OCTA image 3110, in FIG. 31. The partial region 3609 is illustrated on the en face image 3112 and the OCTA image 3110 as a partial region. As a boundary line for the partial region, the boundary line between the upper end (3178 and 3725) and the lower end (3719 and 3726) is illustrated. Note that, in FIG. 37A, an example is illustrated in which Z positions of upper and lower boundary lines for entire and partial regions are the same.

Figure 37B:
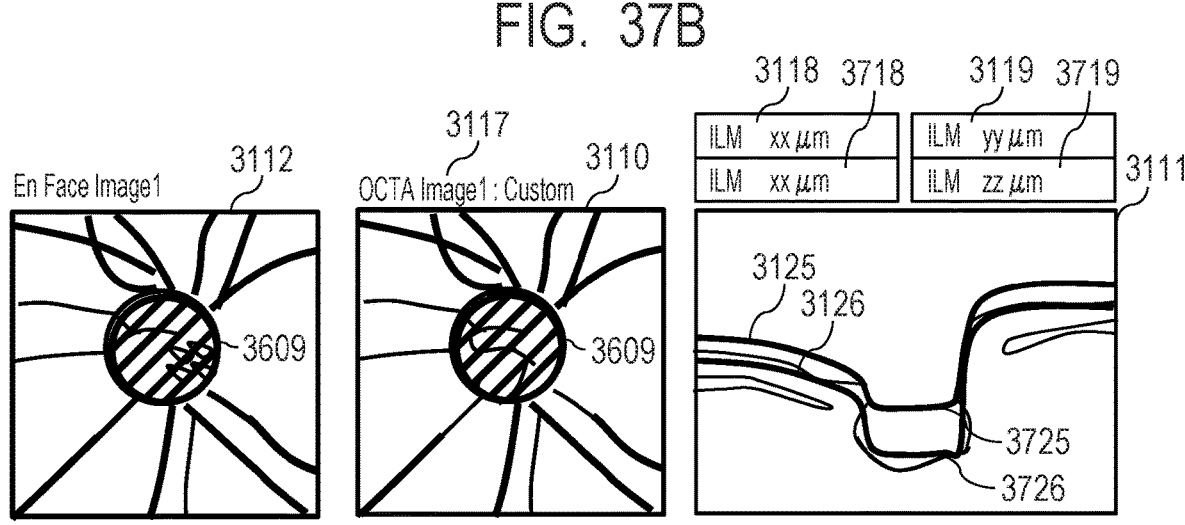
Figure 37C:
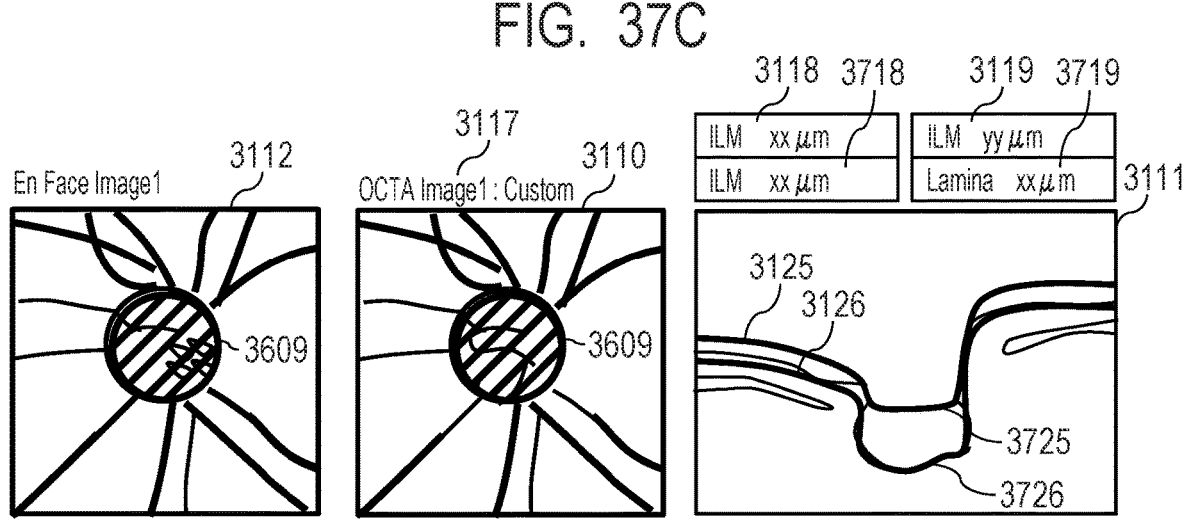

Subsequently, an example in which the position of the boundary line of the partial region is changed is described with reference to FIGS. 37B and 37C. In FIG. 37B, a type of the lower boundary line is the same and only an offset value is changed. When a numerical value of offset is changed from several ten micrometers to several hundred micrometers, a Z position of the boundary line in the partial region moves in the depth direction. In FIG. 37C, an example is illustrated in which the type of the lower boundary line is changed. The boundary line in the partial region is changed from ILM to Lamina. Consequently, the shape of the boundary line in the partial region changes. As illustrated in FIGS. 37B and 37C, in a depth range in the partial region, the offset value in the boundary line+the offset value may be changed or the type of the boundary line may be changed. The operator can change the offset value and the type of the boundary line. The operator can change not only the offset value and the type of the boundary line for the partial region but also an offset value and a type of a boundary line for the entire range. The tomographic image 3111 illustrated in FIGS. 37A to 37C represents one tomographic image of three-dimensional data. However, when the offset value and the boundary line are changed, a common change is performed on the three-dimensional data. That is, in the three-dimensional data, these changes are performed on a tomographic image different from the tomographic image on which these changes are performed. As the change concerning the partial region, a common change is applied to the partial region of the tomographic image in which the partial region is present. Note that, in FIGS. 37A to 37C, a part equivalent to the crossing part of the region 3609 and the tomographic image 3111 indicated by the dotted line 3690 in FIG. 36B is not displayed. However, the dotted line 3690 may be superimposed and displayed on the tomographic image 3111 as in FIG. 36B.

Note that, in FIGS. 37A to 37C, the example is described in which the types of the upper and lower boundary line and the offset values (3118 and 3119 and 3718 and 3719) for the entire range and the partial region are displayed side by side. However, not only this, but, for example, a place of display may be the same on the screen and the types of the upper and lower boundary lines and the offset values may be respectively switched and displayed in combinations of the types of the upper and lower boundary lines and the offset values for the entire range and for the partial region.

With the configuration described above, in this embodiment, the operator can set and change the depth range in order to generate the two-dimensional front image using the three-dimensional data in the different height ranges. Consequently, it is possible to generate a two-dimensional image in a depth range desired by the operator.

Eighth Embodiment: Generate One Two-dimensional Front Image Using Regions Different From One Another in a Plurality of Two-Dimensional Front Images Generated Using Three-Dimensional Data in Different Depth Ranges In the fourth to seventh embodiments, the example is described in which, when the two-dimensional front image is generated using the three-dimensional data in the different depth ranges, the two-dimensional front image is generated by updating the boundary line coordinate in the partial region to the boundary line coordinate different from the boundary line coordinates of the other regions. In an eighth embodiment, an example is described in which one two-dimensional front image is formed by partially combining two-dimensional front images generated separately from one another. Note that, after a plurality of two-dimensional front images is generated, a plurality of regions in the direction crossing the depth direction may be set. In this case, a part of the generated plurality of two-dimensional front images can be extracted to be associated with the set plurality of regions. Consequently, one two-dimensional front image can be generated by combining the extracted plurality of partial images. After the plurality of regions in the direction crossing the depth direction are set, a plurality of two-dimensional front images corresponding to the plurality of regions may be generated. In this case, one two-dimensional front image can be generated by generating a plurality of two-dimensional front images corresponding to the set plurality of regions and combining the generated plurality of two-dimensional front images. Note that, in both the cases, a part of the plurality of images to be combined can be partially superimposed. Consequently, for example, it is possible to easily perform alignment and the like of the plurality of images using the partially overlapping regions. Processing for combining the plurality of images may be processing for sticking together the plurality of images corresponding to the plurality of regions, may be processing for referring to a plurality of partial data corresponding to the plurality of regions from a plurality of image data to thereby combine the plurality of partial data as data, or may be processing for superimposing a part of the other image on a part of a region of one image.

Description is omitted concerning units having the same function as the functions in the fourth to seventh embodiments. An example in which two-dimensional front images generated separately from one another are partially combined in this embodiment is described with reference to FIGS. 38A to 38C.

Figure 38A:
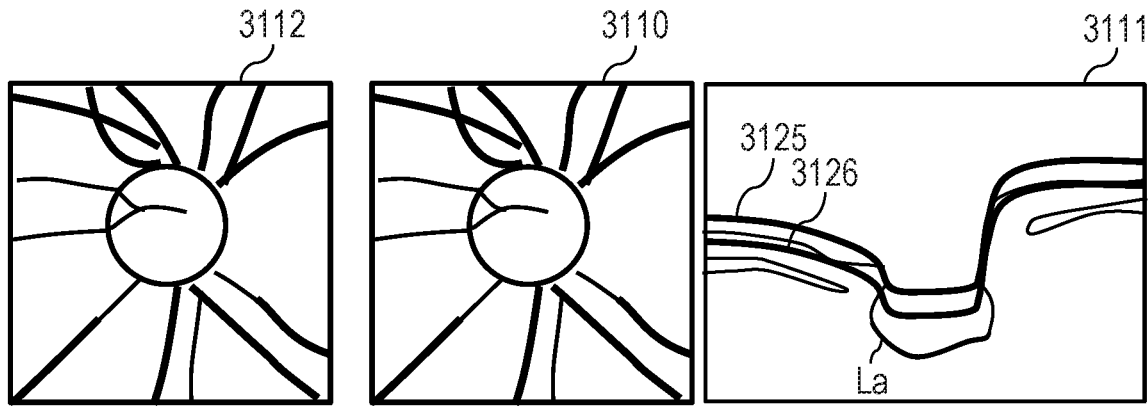
FIG. 38A, FIG. 38B, and FIG. 38C describe two-dimensional front images generated from different depth ranges set in a plurality of regions in a direction that intersects the depth direction.
Figure 38B:
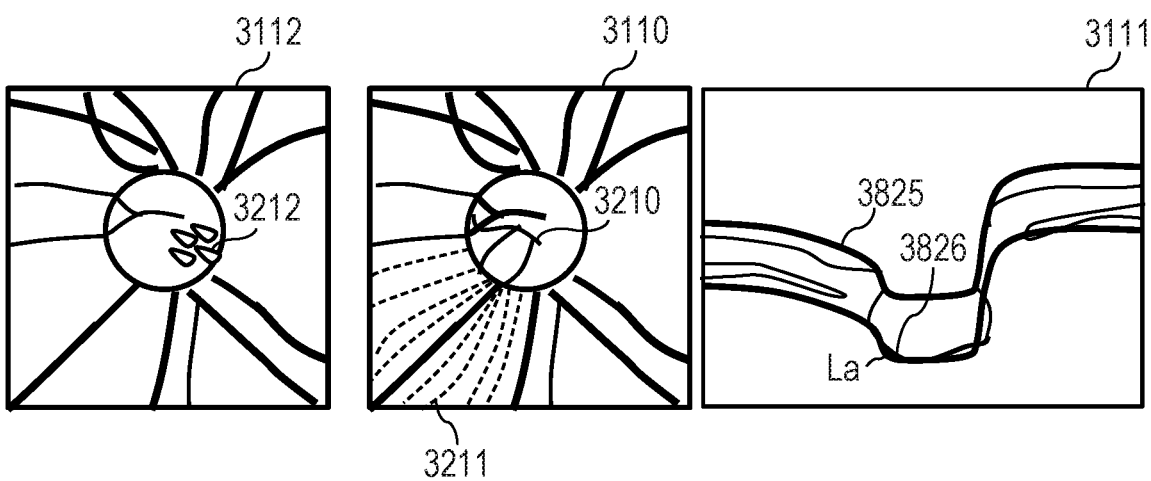

FIG. 38A illustrates the en face image 3112, the first OCTA image 3110, and the first tomographic image 3111 and the upper boundary line 3125 and the lower boundary line 3126, which are the creation ranges of the first OCTA image 3110, in FIG. 31 are illustrated. FIG. 38A illustrates an example of an OCTA image created in a depth range of the radial peripapillary capillaris. FIG. 38B illustrates an example in which the entire lower boundary line 3826 is moved in the depth direction to include the entire lamina cribrosa. The boundary line 3826 is set to an inner boundary membrane (ILM)+an offset value (several hundred micrometers). The upper boundary line 3825 is not moved. As illustrated in FIG. 38B, in the en face image 3112, the lamina pore 3212 is observed. In the OCTA image 3110, the optic disc inside and the blood vessel 3210 inside the lamina cribrosa are observed. On the other hand, in the optic disc periphery, since a range from a nerve fiber layer to the RPE and the choroid is included, contrast of the entire en face image 3112 decreases. A blood vessel of a deep layer section, which is not a shallow layer section, is observed in the OCTA image as an artifact (a broken line 3211 in FIG. 38B).

Figure 38C:
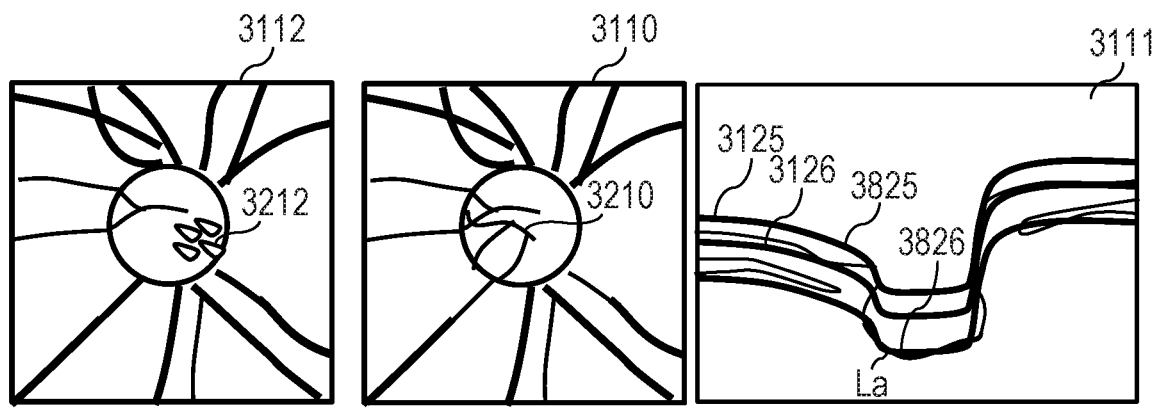

In FIG. 38C, as illustrated in FIG. 38A and FIG. 38B, an image obtained when two-dimensional front images separately generated from different depth ranges are combined as one image is illustrated. Although not illustrated in FIG. 38C, as described in the embodiments above, it is assumed that the region extraction unit 13340 extracts a region of the optic disc. In a two-dimensional front image illustrated in FIG. 38C, the optic disc periphery is generated from a two-dimensional front image illustrated in FIG. 38A and the optic disc inside is generated from a two-dimensional front image illustrated in FIG. 38B.

With the configuration described above, in this embodiment, one two-dimensional front image can be generated by partially combining two-dimensional front images generated separately from one another. Consequently, it is possible to generate a two-dimensional image in a depth range desired by the operator without changing a coordinate position of the boundary line.

Modification 1

In the fourth to eighth embodiments, the example is explained in which the two-dimensional front image is generated with respect to the data subjected to the image quality improving processing (the averaging). However, not only this, but, for example, the present invention is also applicable to three-dimensional data obtained by performing imaging once and not subjected to the image quality improving processing (step S305). Further, the present invention is also applicable to three-dimensional data applied with image quality improving processing other than the averaging. The fourth to eighth embodiments are embodiments concerning a reference in generating a two-dimensional front image. Therefore, the quality of the three-dimensional data may be any quality and a generation method for the three-dimensional data may be any method.

Modification 2

In the fourth to eighth embodiments, the generation method for the two-dimensional front image is described in step S1506. However, not only the image generation but also measurement may be performed using the generated two-dimensional front image. For example, area density, skeleton density, and the like are measured for the OCTA image. In an image in which the optic disc is imaged, the radial peripapillary capillaris and capillaries in the optic disc periphery can be simultaneously measured with one image. If the en face image is used, the density, the area, the volume, and the like of the lamina cribrosa and the layer thickness of the optic disc periphery can be simultaneously measured. It is also possible to display measurement results of the density, the area, the volume, and the like of the lamina cribrosa and the layer thickness of the optic disc periphery on the display unit 1360. For example, the measurement results can be displayed on the report screen illustrated in FIG. 31.

Modification 3

In the seventh embodiment, for example, as the method of moving the boundary line of the partial region in the depth direction, the example is described in which the boundary line is moved by inputting the offset values (3718 and 3719). However, not only this, but, for example, the boundary line may be moved by dragging. Alternatively, a slider may be displayed beside the tomographic image. The slider may be moved to move the range setting for the two-dimensional image generation in association with the movement of the slider. Naturally, these methods can also be applied to a method of moving a boundary line in a region other than the partial region in the depth direction.

Modification 4

In the fourth to eighth embodiments, the example is described in which the OCTA image is generated from the motion contrast data in step S1506. However, an image subjected to projection artifact removal may be displayed as the OCTA image. The projection artifact means that a shadow of a blood vessel in an upper layer is reflected on a lower layer. The projection artifact is a phenomenon in which the shadow changes according to a change due to a flow of blood, whereby an artifact occurs in a place that is not a blood vessel. Such an artifact is sometimes present in the motion contrast data. Therefore, even when a range in which the UI is operated to generate the OCTA image is optionally set, an image from which the artifact is removed may be generated and displayed.

Modification 5

In the fourth to eighth embodiments, the processing from the imaging to the display is described as a series of flow. However, not only this, but, for example, the high-quality image generation processing may be performed using already imaged data. In that case, step S1502 of the processing concerning the imaging is skipped. Instead, an imaged plurality of three-dimensional motion contrast data and an imaged plurality of three-dimensional tomographic images are acquired. The high-quality image generation processing is performed in step S1505. Consequently, concerning data imaged a plurality of times, even if processing is not performed during the imaging, it is possible to execute the image quality improving processing when necessary. Therefore, during the imaging, it is possible to concentrate on only the imaging.

Modification 6

As one of modifications of the fourth to eighth embodiments, one of the image processing apparatuses according to the fourth to eighth embodiments can include a storing unit that stores set different depth ranges in association with an in-plane direction in a generated two-dimensional front image. Consequently, for example, the operator such as the doctor can easily confirm depth ranges of regions in the in-plane direction together with two-dimensional front images in the past by reading the depth ranges of the regions in the in-plane direction from the storing unit.

Modification 7

As one of the modifications of the fourth to eighth embodiments, one of the image processing apparatuses according to the fourth to eighth embodiments can be configured to be capable of selectively executing, according to an instruction of the operator, one of a function of displaying a motion contrast front image and a luminance front image side by side and a function of switching and displaying the motion contrast front image and the luminance front image. Consequently, for example, the operator such as the doctor can easily select a display method for images according to a diagnosis purpose and the like.

Modification 8

As one of the modifications of the fourth to eighth embodiments, one of the image processing apparatuses according to the fourth to eighth embodiments can include a function of follow-up (follow-up observation) of the eye to be inspected. For example, the display control unit 1335 can cause the display unit 1360 to display, side by side, a plurality of two-dimensional front images corresponding to a plurality of examinations performed in different days. For example, at least one of a depth range and a partial region applied to generation of a two-dimensional front image corresponding to a reference examination selected according to an instruction of the operator can be applied to two-dimensional front images corresponding to other examinations. When setting concerning the reference examination is changed according to an instruction of the operator, setting concerning the other examinations can be simultaneously changed. Consequently, for example, the operator such as the doctor can efficiently perform the follow-up (the follow-up observation) of the eye to be inspected.

Modification 9

As one of the modifications of the fourth to eighth embodiments, one of the image processing apparatuses according to the fourth to eighth embodiments may switch, according to a part of the eye to be inspected, which is one of an acquisition target of three-dimensional data and a generation target of a two-dimensional front image of the eye to be inspected, whether a function of setting of different depth ranges with respect to a plurality of regions in the direction crossing the depth direction is applied or not applied. Consequently, for example, when one of the optic disc and the lamina cribrosa region of the eye to be inspected is a target part, the function can be applied. When the yellow spot of the eye to be inspected is the target part, the function can be not applied. That is, when a shallow part and a deep part of the eye to be inspected are mixed as the target part, by applying the function, it is possible to facilitate distinction of the shallow part and the deep part in observation of one two-dimensional front image. On the other hand, for example, when only the shallow part of the eye to be inspected is the target part, since the setting of the depth direction in the past only has to be performed, the function only has to be not applied.

According to one of the disclosed techniques, it is possible to facilitate distinction of a part of attention in one two-dimensional front image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-040032, filed Mar. 6, 2018, and Japanese Patent Application No. 2018-040031, filed Mar. 6, 2018, which are hereby incorporated by reference herein in their entirety.

What is claimed is:

1. An image processing apparatus comprising:
at least one of (a) one or more processors and (b) circuitry, configured to function as a plurality of units comprising:
(1) an identification unit configured to identify a lamina cribrosa region of an eye to be inspected in three-dimensional tomographic image data of the eye to be inspected, the three-dimensional tomographic image data of the eye to be inspected having been obtained by using an OCT optical system, by analyzing the three-dimensional tomographic image data of the eye to be inspected;
(2) a generation unit configured to generate a luminance en face image and a motion contrast en face image of the eye to be inspected by using at least part of the three-dimensional tomographic image data; and
(3) a display control unit configured to cause a display unit to display at least one of the luminance en face image and the motion contrast en face image with information on a position of the identified lamina cribrosa region in a direction intersecting a depth direction of the eye to be inspected, wherein the information is superimposed on the displayed image.

2. The image processing apparatus according to claim 1, wherein the generation unit is configured to use a part of the three-dimensional tomographic image data to generate the luminance en face image and the motion contrast en face image, the part of the three-dimensional tomographic image data having been obtained by using at least one of information on a position of the identified lamina cribrosa region in the depth direction of the eye to be inspected and the information on the position of the identified lamina cribrosa region in the direction intersecting the depth direction.

3. The image processing apparatus according to claim 2, wherein the identification unit is configured to change at least one of the information on the position of the identified lamina cribrosa region in the depth direction of the eye to be inspected and the information on the position of the identified lamina cribrosa region in the direction intersecting the depth direction in accordance with an operator's instruction.

4. The image processing apparatus according to claim 3, wherein the display control unit is configured to cause the display unit to display two-dimensional tomographic images representing the depth direction of the eye to be inspected or the luminance en face image, and
wherein the identification unit is configured to perform the change in accordance with the operator's instruction performed on the displayed image.

5. The image processing apparatus according to claim 1, wherein the information on the position of the identified lamina cribrosa region in the direction intersecting the depth direction of the eye to be inspected includes information representing a position of the identified lamina cribrosa region in an in-plane direction of the luminance en face image and the motion contrast en face image.

6. The image processing apparatus according to claim 1, wherein the three-dimensional tomographic image data includes a plurality of two-dimensional tomographic image data sets of different positions in the eye to be inspected obtained by using the OCT optical system, and
wherein the display control unit is configured to cause the display unit to display information representing a result of analysis of the identified lamina cribrosa region, which is obtained by using at least one of the plurality of two-dimensional tomographic image data sets.

7. The image processing apparatus according to claim 6, wherein the information representing the result of the analysis includes at least one of a position of a perfusion area, a position of a non-perfusion area, a shape of the non-perfusion area, an area of the perfusion area, an area of the non-perfusion area, a length of a blood vessel, curvature of the blood vessel, and density of the blood vessel obtained by using the plurality of two-dimensional tomographic image data sets.

8. The image processing apparatus according to claim 6, wherein the information representing the result of the analysis includes at least one of a position of the lamina cribrosa region, a position of a lamina pore region, a thickness of the lamina cribrosa region, and an area of the lamina pore region obtained by using at least one of the plurality of two-dimensional tomographic image data sets.

9. The image processing apparatus according to claim 1, wherein the display control unit is configured to selectively perform one of a function of displaying the motion contrast en face image or a result of analysis of the motion contrast en face image and the luminance en face image or a result of analysis of the luminance en face image side by side and a function of displaying the images or the results superimposed on each other in accordance with an operator's instruction.

10. The image processing apparatus according to claim 1, wherein the display control unit is configured to cause the display unit to progressively display at least one of a plurality of luminance en face images, a plurality of motion contrast en face images, a plurality of results of analysis of the plurality of luminance en face images, and a plurality of results of analysis of the plurality of motion contrast en face images corresponding to a plurality of examinations performed on different dates.

11. The image processing apparatus according to claim 1, wherein the plurality of units further comprise an acquisition unit configured to acquire a plurality of three-dimensional tomographic image data sets obtained based on measurement light so controlled as to scan a same position on the eye to be inspected, and
wherein the generation unit is configured to generate the luminance en face image by using at least one of the plurality of three-dimensional tomographic image data sets and to generate the motion contrast en face image by using the plurality of three-dimensional tomographic image data sets.

12. An image processing apparatus comprising:
at least one of (a) one or more processors and (b) circuitry, configured to function as a plurality of units comprising:
(1) an identification unit configured to identify a layer boundary of a fundus and a lamina cribrosa region of an eye to be inspected in at least one two-dimensional tomographic image data of a plurality of two-dimensional tomographic image data of different positions in the eye to be inspected, the plurality of two-dimensional tomographic image data of different positions in the eye to be inspected being included in three-dimensional tomographic image data of the eye to be inspected obtained by using an OCT optical system, by analyzing the at least one two-dimensional tomographic image data; and
(2) a display control unit configured to cause a display unit to display a two-dimensional tomographic image representing a depth direction of the eye to be inspected with information on a position of the lamina cribrosa region superimposed on the two-dimensional tomographic image, to display information obtained by analysis of the lamina cribrosa region in a portion inside an optic papilla region in the at least one two-dimensional tomographic image data, and to display information obtained based on the layer boundary of the fundus in a portion outside the optical papilla region in the at least one two-dimensional tomographic image data.

13. The image processing apparatus according to claim 12, wherein the information representing the result of the analysis of the lamina cribrosa region includes at least one of a position of a lamina pore region, a thickness of the lamina cribrosa region, and an area of the lamina pore region obtained by using the at least one two-dimensional tomographic image data.

14. The image processing apparatus according to claim 12, wherein the information representing the result of the analysis of the lamina cribrosa region includes at least one of a position of a perfusion area, a position of a non-perfusion area, a shape of the non-perfusion area, an area of the perfusion area, an area of the non-perfusion area, a length of a blood vessel, curvature of the blood vessel, and density of the blood vessel obtained by using the three-dimensional tomographic image data.

15. The image processing apparatus according to claim 12, wherein the information obtained based on the layer boundary of the fundus includes information obtained based on a thickness of at least one of a nerve fiber layer, a ganglion cell layer, and a ganglion cell complex.

16. The image processing apparatus according to claim 12, wherein the information obtained based on the layer boundary of the fundus includes at least one of a position of a blood vessel contained in at least one of a nerve fiber layer, a ganglion cell layer, an inner plexiform layer, and an inner nuclear layer, a position of a non-perfusion area, a shape of the non-perfusion area, an area of a perfusion area, an area of the non-perfusion area, a length of a blood vessel, curvature of the blood vessel, and density of the blood vessel.

17. An image processing method comprising:
identifying a lamina cribrosa region of an eye to be inspected in three-dimensional tomographic image data of the eye to be inspected, the three-dimensional tomographic image data of the eye to be inspected having been obtained by using an OCT optical system, by analyzing the three-dimensional tomographic image data of the eye to be inspected;
generating a luminance en face image and a motion contrast en face image of the eye to be inspected by using at least part of the three-dimensional tomographic image data; and
causing a display unit to display at least one of the luminance en face image and the motion contrast en face image with the information on a position of the identified lamina cribrosa region in a direction intersecting a depth direction of the eye to be inspected, wherein the information is superimposed on the displayed image.

18. A non-transitory computer-readable medium that stores a program that causes, when executed by a computer, the computer to carry out the image processing method according to claim 17.

* * * * *